United States Patent
Zhang et al.

(10) Patent No.: US 7,247,625 B2
(45) Date of Patent: Jul. 24, 2007

(54) 6-AMINO-1,4-DIHYDRO-BENZO[D][1,3] OXAZIN-2-ONES AND ANALOGS USEFUL AS PROGESTERONE RECEPTOR MODULATORS

(75) Inventors: Puwen Zhang, Audubon, PA (US); Jeffrey Kern, Gilbertsville, PA (US)

(73) Assignee: Wyeth, Madison, NJ (US)

( * ) Notice: Subject to any disclaimer, the term of this patent is extended or adjusted under 35 U.S.C. 154(b) by 396 days.

(21) Appl. No.: 10/946,476

(22) Filed: Sep. 21, 2004

(65) Prior Publication Data

US 2005/0085470 A1  Apr. 21, 2005

Related U.S. Application Data

(60) Provisional application No. 60/509,930, filed on Oct. 9, 2003.

(51) Int. Cl.
C07D 265/18 (2006.01)
A61K 31/537 (2006.01)
A61K 31/536 (2006.01)

(52) U.S. Cl. .................. 514/230.5; 544/71; 544/92
(58) Field of Classification Search .................. 544/71, 544/92; 514/230.5
See application file for complete search history.

(56) References Cited

U.S. PATENT DOCUMENTS

| | | | |
|---|---|---|---|
| 5,719,136 A | 2/1998 | Chwalisz et al. | |
| 5,874,430 A | 2/1999 | Christ et al. | |
| 6,306,851 B1 | 10/2001 | Santilli et al. | |
| 6,339,098 B1 | 1/2002 | Collins et al. | |
| 6,355,648 B1 | 3/2002 | Fensome et al. | |
| 6,358,948 B1 | 3/2002 | Zhang et al. | |
| 6,369,056 B1 | 4/2002 | Zhang et al. | |
| 6,380,235 B1 | 4/2002 | Zhang et al. | |
| 6,391,907 B1 | 5/2002 | Fensome et al. | |
| 6,407,101 B1 | 6/2002 | Collins et al. | |
| 6,417,214 B1 | 7/2002 | Ullrich et al. | |
| 6,436,929 B1 | 8/2002 | Zhang et al. | |
| 6,441,019 B2 | 8/2002 | Santilli et al. | |
| 6,509,334 B1 | 1/2003 | Zhang et al. | |
| 6,521,657 B2 | 2/2003 | Fensome et al. | |
| 6,583,145 B1 | 6/2003 | Fensome et al. | |
| 6,608,068 B2 | 8/2003 | Fensome et al. | |
| 6,693,103 B2 | 2/2004 | Zhang et al. | |
| 2002/0169198 A1 | 11/2002 | Fensome et al. | |
| 2003/0092711 A1 | 5/2003 | Zhang et al. | |
| 2003/0225109 A1 | 12/2003 | Fensome et al. | |

FOREIGN PATENT DOCUMENTS

| | | |
|---|---|---|
| WO | WO00/66555 | 11/2000 |
| WO | WO00/66556 A1 | 11/2000 |
| WO | WO00/66560 | 11/2000 |
| WO | WO00/66564 A1 | 11/2000 |
| WO | WO00/66570 | 11/2000 |
| WO | WO00/66591 | 11/2000 |
| WO | WO00/66592 A1 | 11/2000 |
| WO | WO016108 A3 | 3/2001 |

OTHER PUBLICATIONS

Wolff Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
John Wiebe, Endocrine-Related Cancer (2006) 13, 717-738.*
Hamann et al, Synthesis and Biological Activity of Novel Nonsteroidal Progesterone Receptor Antagonists, Annals New York Academy of Sciences, 761, pp. 382-387, (1995).
Kurihara et al, Synthesis of (±)-PF1092A, B, C; New Nonsteroidal Progesterone Receptor Ligands, The Journal of Antibiotics, vol. 50, No. 4, pp. 360-362, (Apr. 1997).
Perlman et al, 20-Oxopregnacalciferols: Vitamin D Compounds that bind the Progesterone Receptor, Tetrahedron Letters, vol. 35, No. 15, pp. 2295-2298, (1994).
Combs et al, Nonsteroidal Progesterone Receptor Ligands. 2. High-Affinity Ligands with Selectivity for Bone cell Progesterone Receptors, Journal of Medicinal Chemistry, vol. 38, No. 25, (1995).
Tegley et al, 5-Benzylidene 1,2-Dihydrochromeno[3,4-f]Quinolines, A Novel Class of nonsteroidal Human Progesterone Receptor Agonists, J. Med. Chem., 41, pp. 4354-4359, (1998).
Zhi et al, Nonsteroidal Progesterone Receptor Antagonists based on 6-Thiophenehydroquinolines, Bioorg. Med. Chem. Lett. 10, pp. 415-418, (2000).

(Continued)

Primary Examiner—Kahsay Habte
(74) Attorney, Agent, or Firm—Arnold S. Milowsky; Howson & Howson LLP

(57) ABSTRACT

Compounds having the structure of formula I are provided. In formula I, $R_1$ is H, OH, substituted or unsubstituted $C_1$ to $C_3$ alkyl, $C_1$ to $C_3$ perfluoroalkyl, or $COR_6$; $R_6$ is H, substituted or unsubstituted $C_1$ to $C_4$ alkyl, aryl, substituted or unsubstituted $C_1$ to $C_4$ alkoxy, substituted or unsubstituted $C_1$ to $C_3$ aminoalkyl; $R_2$ and $R_3$ are H, substituted or unsubstituted $C_1$ to $C_6$ alkyl, $C_1$ to $C_6$ perfluoroalkyl, substituted or unsubstituted $C_2$ to $C_6$ alkenyl, substituted or unsubstituted $C_2$ to $C_6$ alkynyl, substituted or unsubstituted $C_3$ to $C_6$ cycloalkyl, substituted or unsubstituted aryl, or substituted or unsubstituted heterocyclic; or $R_2$ and $R_3$ are fused to form spirocyclic rings; $R_4$ is $NHR_7$, $OR_7$, $NHSO_2R_7$, or $OSO_2R_7$; Q is O, S, $NR_8$, or $CR_9R_{10}$; or a pharmaceutically acceptable salt, ester, or prodrug thereof. Such compounds are useful as progesterone receptor modulators and for treating progesterone receptor related conditions.

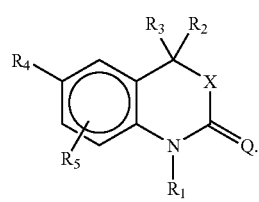

I

15 Claims, No Drawings

OTHER PUBLICATIONS

Michna et al, Differentiation Therapy with Progesterone Antagonists, Ann. N.Y. Acad. Sci. 761, 224, (1995).

Kettel et al, Endocrine Responses to Long-Term Administration of the Antiprogesterone RU486 in Patients with Pelvic Endometriosis, Fertility and Sterility, vol. 56, No. 3, (Sep. 1991).

Murphy et al, Regression of Uterine Leiomyomata in Response to the Antiprogesterone RU 486, Journal of Clinical Endocrinology and Metabolism, vol. 76, No. 2, pp. 513-517, (1993).

Horowitz et al, Progestins, Progesterone Receptors, and Breast Cancer, SciFinder, pp. 1-2, Abstract, (Mar. 10, 1998).

Kekkonen et al, Sequential Regimen of the Antiprogesterone RU486 and Synthetic Progestin for Contraception, Fertility and Sterility, vol. 60, 610, No. 4, (Oct. 1993).

Ulmann et al, Clinical Uses of Mifepristone (MFP), Ann. N.Y. Acad. Sci., 261, 248, (1995).

Mangelsdorf et al, The Nuclear Receptor Superfamily: The Second Decade, Cell, vol. 83, pp. 835-839, (Dec. 15, 1995).

Zhi et al, 5-Aryl-1,2-dihydrochromeno[3,4-f]Quinolines: A Novel Class of Nonsteroidal Human Progesterone Receptor Agonists, J. Med. Chem.. 41(3):291-302, (Jan. 29, 1998).

* cited by examiner

6-AMINO-1,4-DIHYDRO-BENZO[D][1,3] OXAZIN-2-ONES AND ANALOGS USEFUL AS PROGESTERONE RECEPTOR MODULATORS

CROSS-REFERENCE TO RELATED APPLICATIONS

This application claims the benefit of the priority of U.S. Provisional Patent Application No. 60/509,930, filed Oct. 9, 2003.

BACKGROUND OF THE INVENTION

The present invention relates to compounds that are useful as modulators of the progesterone receptor, their preparation and use thereof.

Intracellular receptors (IR) form a class of structurally related gene regulators known as "ligand dependent transcription factors". The steroid receptor family is a subset of the IR family, including progesterone receptor (PR), estrogen receptor (ER), androgen receptor (AR), glucocorticoid receptor (GR), and mineralocorticoid receptor (MR).

The natural hormone, or ligand, for the PR is the steroid progesterone, but synthetic compounds, such as medroxyprogesterone acetate or levonorgestrel, have been made which also serve as PR ligands. Once a ligand is present in the fluid surrounding a cell, it passes through the membrane via passive diffusion, and binds to the IR to create a receptor/ligand complex. This complex binds to specific gene promoters present in the cell's DNA. Once bound to the DNA the complex modulates the production of mRNA and the protein encoded by that gene.

A compound that binds to an IR and mimics the action of the natural hormone is termed an agonist. Conversely, a compound which inhibits the effect of the hormone is an antagonist.

PR agonists (natural and synthetic) are known to play an important role in the health of women. PR agonists are used in birth control formulations, either along or in the presence of an ER agonist. ER agonists are used to treat the symptoms of menopause, but have been associated with a proliferative effect on the uterus which can lead to an increased risk of uterine cancers. Co-administration of a PR agonist reduces/ablates that risk.

PR antagonists can also be used in contraception. In this context they can be administered alone, in combination with a PR agonist, or in combination with a partial ER antagonist such as tamoxifen.

PR antagonists can also be useful for the treatment of hormone dependent breast cancers as well as uterine and ovarian cancers. PR antagonists can also be useful for the treatment of non-malignant chronic conditions such as uterine fibroids and endometriosis.

PR antagonists can also be useful in hormone replacement therapy for post menopausal patients in combination with a partial ER antagonist such as tamoxifen.

PR antagonists, such as mifepristone and onapristone, have been shown to be effective in a model of hormone dependent prostate cancer, which can indicate their utility in the treatment of this condition in men.

What are needed are other compounds which function as PR modulators, including PR agonists or antagonists.

SUMMARY OF THE INVENTION

In one aspect, compounds of formula I, pharmaceutically acceptable salts, tautomers, and prodrugs thereof, are provided.

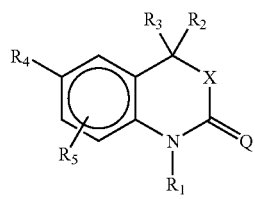

Compounds of formula I bind to the progesterone receptor and function as progesterone receptor modulators.

In a further aspect, compounds of formula I can be used for contraception; in the treatment of uterine fibroids, endometriosis, dysmenorrhea, breast cancer, uterine caner, ovarian cancer, prostate cancer, and meningioma; hormone replacement therapy, including perimenopausal, menopausal, and post-menopausal hormone replacement therapy; and in the treatment of skin disorders, including acne and hirsutism.

In yet another aspect, pharmaceutical compositions containing a compound of formula I and a physiologically compatible carrier are provided.

In a further aspect, methods for preparing compounds of formula I are provided.

In another aspect, kits containing one or more compounds of formula I and a physiologically compatible carrier are provided.

Other aspects and advantages of the present invention are described further in the following detailed description of the preferred embodiments thereof.

DETAILED DESCRIPTION OF THE INVENTION

The term "tautomer" is meant to describe a compound which can exist in more than one isomeric state.

The term "skin" is meant to describe the outer covering of a mammalian form including, without limitation, the epidermis, dermis, and subcutaneous tissues. Typically, the skin can include other components such as hair follicles and sweat glands.

The term "acne" is meant to include any skin disorder where a skin pore becomes blocked and/or thereby becomes inflamed. The term acne includes, without limitation, superficial acne, including comedones, inflamed papules, superficial cysts, pustules, and deep acne, including deep inflamed modules and pus-filled cysts. Specific acne conditions can include, but are not limited to, acne vulgaris, acne comedo, papular acne, premenstrual acne, preadolescent acne, acne venenata, acne cosmetica, pomade acne, acne detergicans, acne excoriee, gram negative acne, acne rosacea, pseudofolliculitis barbae, folliculitis, perioral dermatitis, and hiddradenitis suppurativa.

The term "hirsutism" is meant to describe a skin disorder where an overgrowth of hair is observed in areas of the body which are not normally subject to excessive hair growth.

A number of skin disorders can be treated according to the methods of the present invention and include skin disorders of the hair follicles and sebaceous glands. Preferably, skin disorders such as acne and hirsutism, among others, can be treated according to the present invention.

Other skin disorders can include dry/chapped skin, seboria, psoriasis, or alopecia. The invention is also useful for treating the skin against the effects of environmental conditions.

As used herein, the terms "anti-progestational agents", "anti-progestins" and "progesterone receptor antagonists" are understood to be synonymous. Similarly, "progestins", "progestational agents" and "progesterone receptor agonists" are understood to refer to compounds of the same activity.

The term "room temperature" is meant to describe a temperature of about 23 to about 25° C. However, one of skill in the art would readily understand that the specific room temperature can vary depending upon the experimental conditions.

I. Compounds of the Invention

The present invention provides compounds of formula I having the structure:

wherein:

$R_1$ is H, OH, $C_1$ to $C_3$ alkyl, substituted $C_1$ to $C_3$ alkyl, $C_1$ to $C_3$ perfluoroalkyl, or $COR_6$;

$R_6$ is H, $C_1$ to $C_4$ alkyl, substituted $C_1$ to $C_4$ alkyl, aryl, substituted aryl, $C_1$ to $C_4$ alkoxy, substituted $C_1$ to $C_4$ alkoxy, $C_1$ to $C_3$ aminoalkyl, or substituted $C_1$ to $C_3$ aminoalkyl;

$R_2$ and $R_3$ are independently selected from among H, $C_1$ to $C_6$ alkyl substituted $C_1$ to $C_6$ alkyl, $C_1$ to $C_6$ perfluoroalkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_6$ cycloalkyl, substituted $C_3$ to $C_6$ cycloalkyl, aryl, substituted aryl, heterocyclic, and substituted heterocyclic;

or $R_2$ and $R_3$ are fused to form:

(i) an optionally substituted 3 to 8 membered saturated spirocyclic ring;

(ii) an optionally substituted 3 to 8 membered spirocyclic ring having in its backbone one or more carbon-carbon double bonds; or (iii) an optionally substituted 3 to 8 membered saturated spirocyclic ring having in its backbone one to three heteroatoms selected from the group consisting of O, S, and N;

$R_4$ is $NHR_7$, $OR_7$, $NHSO_2R_7$, $OSO_2R_7$, $NCH_3R_7$ or $NCH_3SO_2R_7$;

$R_7$ is selected from among (a) and (b):

(a) an aryl ring which is optionally substituted with one to three independent substituents selected from among H, halogen, OH, CN, $C_1$ to $C_3$ alkyl, substituted $C_1$ to $C_3$ alkyl, $C_2$ to $C_3$ alkenyl, substituted $C_2$ to $C_3$ alkenyl, $C_2$ to $C_3$ alkynyl, substituted $C_2$ to $C_3$ alkynyl, $C_1$ to $C_3$ alkoxy, substituted $C_1$ to $C_3$ alkoxy, $C_5$ to $C_8$ aryloxy, substituted $C_5$ to $C_8$ aryloxy, $C_1$ to $C_3$ thioalkoxy, substituted $C_1$ to $C_3$ thioalkoxy, amino, $C_1$ to $C_3$ aminoalkyl, substituted $C_1$ to $C_3$ aminoalkyl, $NO_2$, $C_1$ to $C_3$ perfluoroalkyl, $COR_B$, $CR_B$=$NOR_C$, $OCOR_B$, $NR_CCOR_B$, 5 or 6 membered heterocyclic ring containing in its backbone 1 to 3 heteroatoms selected from among N, O, and S; and (b) a 5 or 6 membered heterocyclic ring containing in its backbone 1 to 3 heteroatoms selected from among O, S, SO, $SO_2$ and N and optionally substituted with one to three independent substituents selected from among H, halogen, OH, CN, $C_1$ to $C_3$ alkyl, substituted $C_1$ to $C_3$ alkyl, $C_2$ to $C_3$ alkenyl, substituted $C_2$ to $C_3$ alkenyl, $C_2$ to $C_3$ alkynyl, substituted $C_2$ to $C_3$ alkynyl, $C_1$ to $C_3$ alkoxy, substituted $C_1$ to $C_3$ alkoxy, $C_1$ to $C_3$ thioalkoxy, substituted $C_1$ to $C_3$ thioalkoxy, amino, $C_1$ to $C_3$ aminoalkyl, substituted $C_1$ to $C_3$ aminoalkyl, $NO_2$, $C_1$ to $C_3$ perfluoroalkyl, $COR_B$, $CR_B$=$NOR_C$, $OCOR_B$, $NR_CCOR_B$, and 5 or 6 membered heterocyclic ring having in its backbone 1 to 3 heteroatoms selected from among N, O, and S;

$R_B$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R_C$ is H, $C_1$ to $C_3$ alkyl, or substituted $C_1$ to $C_3$ alkyl;

$R_5$ is H, OH, halogen, CN, $NO_2$, $C_1$ to $C_6$ alkyl, substituted $C_1$ to $C_6$ alkyl, $C_2$ to $C_6$ alkynyl, substituted $C_2$ to $C_6$ alkynyl, $C_1$ to $C_6$ alkoxy, substituted $C_1$ to $C_6$ alkoxy, amino, $C_1$ to $C_6$ aminoalkyl, or substituted $C_1$ to $C_6$ aminoalkyl;

Q is O, S, $NR_8$, or $CR_9R_{10}$;

$R_8$ is selected from among CN, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $SO_2CF_3$, $OR_{11}$, and $NR_{11}R_{12}$;

$R_9$ and $R_{10}$ are independent substituents selected from among H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $NO_2$, CN, and $CO_2R_{11}$;

or $CR_9R_{10}$ comprise a six membered ring as shown by the structure below:

$R_{11}$ and $R_{12}$ are independently selected from among H, $C_1$ to $C_6$ alkyl, substituted $C_1$ to $C_6$ alkyl, aryl, substituted aryl, heterocyclic, substituted heterocyclic, acyl, and sulfonyl;

X is O, S, $NR^E$, or $CR^ER^F$ $R^E$ and $R^F$ are independently H, $C_1$ to $C_4$ lower alkyl, or $C_1$ to $C_4$ perfluoroalkyl;

or a pharmaceutically acceptable salt, tautomer, or prodrug thereof.

$R^5$ may be present at the 5-, 7-, or 8-position of the compound. The invention further provides for compounds of formula including 6-[(3-chlorophenyl)amino]-4,4-diethyl-1-methyl-1,4-dihydro-2H-3,1-benzoxazin-2-one; 4-(4-chlorophenyl)-6-[(3-chlorophenyl)amino]-1,4-dimethyl-1,4-dihydro-2H-3,1-benzoxazin-2-one; 6-[(3,4-dichlorophenyl)amino]-4,4-diethyl-1-methyl-1,4-dihydro-2H-3,1-benzoxazin-2-one; 6-[(3,5-dichlorophenyl)amino]-4,4-diethyl-1-methyl-1,4-dihydro-2H-3,1-benzoxazin-2-one; 4,4-diethyl-6-[(3-fluoro-5-nitrophenyl)amino]-1-methyl-1,4-dihydro-2H-3,1-benzoxazin-2-one; 3-[(4,4-diethyl-1-methyl-2-oxo-1,4-dihydro-2H-3,1-benzoxazin-6-yl)amino]-5-fluorobenzonitrile; 6-[(2,3-dichlorophenyl)amino]-4,4-diethyl-1-methyl-1,4-dihydro-2H-3,1-benzoxazin-2-one; 6-[(2,5-dichlorophenyl)amino]-4,4-diethyl-1-methyl-1,4-dihydro-2H-3,1-benzoxazin-2-one; 6-[(3,4-difluorophenyl)amino]-4,4-diethyl-1-methyl-1,4-dihydro-2H-3,1-benzoxazin-2-one; 6-[(3,5-difluorophenyl)amino]-4,4-diethyl-1-methyl-1,4-dihydro-2H-3,1-benzoxazin-2-one; 6-[(3-chloro-4-fluorophenyl)amino]-4,4-diethyl-1-methyl-1,4-dihydro-2H-3,1-benzoxazin-2-one; 6-[(3-acetylphenyl)amino]-4,4-diethyl-1-methyl-1,4-dihydro-2H-3,1-benzoxazin-2-one; 5-[(4,4-diethyl-1-methyl-2-oxo-1,4-dihydro-2H-3,1-benzoxazin-6-yl)amino]-2-fluorobenzonitrile; 6-[(3-acetyl-4-fluorophenyl)amino]-4,4-diethyl-1-methyl-1,4-dihydro-2H-3,1-benzoxazin-2-one; 6-[(4-bromophenyl)amino]-4,4-diethyl-1-methyl-1,4-dihydro-2H-3,1-benzoxazin-2-one; 4-[(4,4-diethyl-1-methyl-2-oxo-1,4-dihydro-2H-3,1-benzoxazin-6-yl)amino]-2-fluorobenzonitrile; 6-[(2,3-dichlorophenyl)amino]-4,4-dimethyl-1,4-dihydro-2H-3,1-benzoxazin-2-one; 6-[(2,3-dichlorophenyl)amino]-1,4,4-trimethyl-1,4-dihydro-2H-3,1-benzoxazin-2-one; 6-[(4-bromophenyl)amino]-1,4,4-trimethyl-1,4-dihydro-2H-3,1-benzoxazin-2-one; 1,4,4-trimethyl-6-[(4-nitrophenyl)amino]-1,4-dihydro-2H-3,1-benzoxazin-2-one; 6-[(3-chloro-4-fluorophenyl)amino]-4,4-diethyl-5-fluoro-1-methyl-1,4-dihydro-2H-3,1-benzoxazin-2-one; 6-[(3-chlorophenyl)amino]-4-ethyl-4-thien-2-yl-1,4-dihydro-2H-3,1-benzoxazin-2-one; 6-[(3-chlorophenyl)amino]-4-ethyl-1-methyl-4-thien-2-yl-1,4-dihydro-2H-3,1-benzoxazin-2-one; 6-[(3-chloro-4-fluorophenyl)amino]-4-ethyl-4-thien-2-yl-1,4-dihydro-2H-3,1-benzoxazin-2-one; 6-[(3-chloro-4-fluorophenyl)amino]-4-ethyl-1-methyl-4-thien-2-yl-1,4-dihydro-2H-3,1-benzoxazin-2-one; 5-fluoro-3-[(1-methyl-2-oxo-1,2-dihydrospiro[3,1-benzoxazine-4,1'-cyclopentan]-6-yl)amino]benzonitrile; 6-[(4-bromophenyl)amino]-4-(4-chlorophenyl)-1,4-dimethyl-1,4-dihydro-2H-3,1-benzoxazin-2-one; 6-[(4-bromophenyl)amino]-4-ethyl-1-methyl-4-thien-2-yl-1,4-dihydro-2H-3,1-benzoxazin-2-one; 4-[(1,4,4-trimethyl-2-oxo-1,4-dihydro-2H-3,1-benzoxazin-6-yl)amino]benzonitrile; 4-[(1,4,4-trimethyl-2-oxo-1,4-dihydro-2H-3,1-benzoxazin-6-yl)amino]benzonitrile; 6-[(2,4-dichlorophenyl)amino]-1,4,4-trimethyl-1,4-dihydro-2H-3,1-benzoxazin-2-one; 1,4,4-trimethyl-6-(1-naphthylamino)-1,4-dihydro-2H-3,1-benzoxazin-2-one; 6-[(4-bromophenyl)amino]-1,4-dimethyl-4-thien-2-yl-1,4-dihydro-2H-3,1-benzoxazin-2-one; 6-[(3,4-dichlorophenyl)amino]-1,4,4-trimethyl-1,4-dihydro-2H-3,1-benzoxazin-2-one; 6-[(2-chloro-4-nitrophenyl)amino]-1,4,4-trimethyl-1,4-dihydro-2H-3,1-benzoxazin-2-one; 6-[(2-methoxyphenyl)amino]-1,4,4-trimethyl-1,4-dihydro-2H-3,1-benzoxazin-2-one; 1,4,4-trimethyl-6-[(2-methylphenyl)amino]-1,4-dihydro-2H-3,1-benzoxazin-2-one; 6-[(2-bromophenyl)amino]-1,4,4-trimethyl-1,4-dihydro-2H-3,1-benzoxazin-2-one; 4-(4-chlorophenyl)-6-[(4-chlorophenyl)amino]-1,4-dimethyl-1,4-dihydro-2H-3,1-benzoxazin-2-one; 6-[(4-bromo-2-chlorophenyl)amino]-1,4,4-trimethyl-1,4-dihydro-2H-3,1-benzoxazin-2-one; 6-[(4-ethoxyphenyl)amino]-1,4,4-trimethyl-1,4-dihydro-2H-3,1-benzoxazin-2-one; 6-[(4-bromophenyl)amino]-1-ethyl-4,4-dimethyl-1,4-dihydro-2H-3,1-benzoxazin-2-one; 6-[(2-ethylphenyl)amino]-1,4,4-trimethyl-1,4-dihydro-2H-3,1-benzoxazin-2-one; 1,4,4-Trimethyl-6-(4-phenoxy-phenylamino)-1,4-dihydro-benzo[d][1,3]oxazin-2-one; 6-(4-hydroxy-phenylamino)-1,4,4-trimethyl-1,4-dihydro-benzo[d][1,3]oxazin-2-one; 6-[(4-bromophenyl)amino]-4,4-bis(4-chlorophenyl)-1-methyl-1,4-dihydro-2H-3,1-benzoxazin-2-one; 4,4-bis(4-chlorophenyl)-6-[(3-chlorophenyl)amino]-1-methyl-1,4-dihydro-2H-3,1-benzoxazin-2-one; 4-benzyl-6-[(4-bromophenyl)amino]-1,4-dimethyl-1,4-dihydro-2H-3,1-benzoxazin-2-one; 4-benzyl-6-[(2-chlorophenyl)amino]-1,4-dimethyl-1,4-dihydro-2H-3,1-benzoxazin-2-one; 4-benzyl-6-[(3-chlorophenyl)amino]-1,4-dimethyl-1,4-dihydro-2H-3,1-benzoxazin-2-one; 6-[(4-bromophenyl)amino]-1-isopropyl-4,4-dimethyl-1,4-dihydro-2H-3,1-benzoxazin-2-one; 6-[(4-chlorophenyl)amino]-8-methoxy-1,4,4-trimethyl-1,4-dihydro-2H-3,1-benzoxazin-2-one; 4-(4-chlorophenyl)-6-[(3-chlorophenyl)amino]-4-ethyl-1,4-dihydro-2H-3,1-benzoxazin-2-one; 4-(4-chlorophenyl)-6-[(3-chlorophenyl)amino]-4-ethyl-1-methyl-1,4-dihydro-2H-3,1-benzoxazin-2-one; 4-(4-chlorophenyl)-6-[(3-chlorophenyl)amino]-1,4,8-trimethyl-1,4-dihydro-2H-3,1-benzoxazin-2-one; 6-[(3-chlorophenyl)amino]-4-ethyl-4-phenyl-1,4-dihydro-2H-3,1-benzoxazin-2-one; 6-[(3-chlorophenyl)amino]-4-ethyl-1-methyl-4-phenyl-1,4-dihydro-2H-3,1-benzoxazin-2-one; 4-(4-chlorophenyl)-6-[(3-chlorophenyl)amino]-8-methoxy-1,4-dimethyl-1,4-dihydro-2H-3,1-benzoxazin-2-one; 6-(3-Chloro-phenylamino)-1,4,4-trimethyl-1,4-dihydro-benzo[d][1,3]oxazin-2-one; 6-(4-Fluoro-phenylamino)-1,4,4-trimethyl-1,4-dihydro-benzo[d][1,3]oxazin-2-one; 6-(4-Methoxy-phenylamino)-1,4,4-trimethyl-1,4-dihydro-benzo[d][1,3]oxazin-2-one; 1,4,4-Trimethyl-6-p-tolylamino-1,4-dihydro-benzo[d][1,3]oxazin-2-one; 6-(4-Bromo-phenylamino)-1,4,4-trimethyl-1,4-dihydro-benzo[d][1,3]oxazin-2-one; 6-(3,4-Difluoro-phenylamino)-1,4,4-trimethyl-1,4-dihydro-benzo[d][1,3]oxazin-2-one; 6-(3,5-Difluoro-phenylamino)-1,4,4-trimethyl-1,4-dihydro-benzo[d][1,3]oxazin-2-one; 6-(2-Fluoro-3-methoxy-phenylamino)-1,4,4-trimethyl-1,4-dihydro-benzo[d][1,3]oxazin-2-one; (4,4-dimethyl-2-oxo-1,4-dihydro-2H-3,1-benzoxazin-6-yl)-2,3-dichlorobenzenesulfonate; (1,4,4-trimethyl-2-oxo-1,4-dihydro-2H-3,1-benzoxazin-6-yl)-2,3-dichlorobenzenesulfonate; 2,3-dichloro-N-(4,4-dimethyl-2-oxo-1,4-dihydro-2H-3,1-benzoxazin-6-yl)benzenesulfonamide; 2,3-dichloro-N-(1,4,4-trimethyl-2-oxo-1,4-dihydro-2H-3,1-benzoxazin-6-yl)benzenesulfonamide; 6-{[4-(dimethylamino)phenyl]amino}-1,4,4-trimethyl-1,4-dihydro-2H-3,1-benzoxazin-2-one; 6-[(4-chlorophenyl)amino]-1,4,4-trimethyl-1,4-dihydro-2H-3,1-benzoxazin-2-one; and 6-[(2-chlorophenyl)amino]-1,4,4-trimethyl-1,4-dihydro-2H-3,1-benzoxazin-2-one; or a pharmaceutically acceptable salt, tautomer, or prodrug thereof.

The invention also provides compounds of formula I including 6-[(3,4-difluorophenyl)amino]-4,4-diethyl-1-methyl-1,4-dihydro-2H-3,1-benzoxazine-2-thione; and 6-[(4-bromophenyl)amino]-1,4,4-trimethyl-1,4-dihydro-2H-3,1-benzoxazine-2-thione; or a pharmaceutically acceptable salt, tautomer, or prodrug thereof.

The invention further provides compounds of formula I including 6-(3-chloro-4-fluorophenoxy)-4,4-diethyl-1-methyl-1,4-dihydro-benzo[d][1,3]oxazin-2-one and 3-(4,4-diethyl-1-methyl-2-oxo-1,4-dihydro-2H-benzo[d][1,3]oxazin-6-yloxy)-5-fluoro-benzonitrile; or a pharmaceutically acceptable salt, tautomer, or prodrug thereof.

The compounds of this invention can contain an asymmetric carbon atom and/or one or more asymmetric centers and can thus give rise to optical isomers and diastereomers. While shown without respect to stereochemistry in Formula I, the present invention includes such optical isomers and diastereomers; as well as the racemic and resolved, enantiomerically pure R and S stereoisomers; as well as other mixtures of the R and S stereoisomers and pharmaceutically acceptable salts, tautomers, or prodrugs thereof.

The term "alkyl" is used herein to refer to both straight- and branched-chain saturated aliphatic hydrocarbon groups having 1 to about 10 carbon atoms, and desirably about 1 to about 8 carbon atoms. The term "alkenyl" is used herein to refer to both straight- and branched-chain alkyl groups having one or more carbon-carbon double bonds and containing about 2 to about 10 carbon atoms. Desirably, the term alkenyl refers to an alkyl group having 1 or 2 carbon-carbon double bonds and having 2 to about 6 carbon atoms. The term "alkynyl" group is used herein to refer to both straight- and branched-chain alkyl groups having one or more carbon-carbon triple bond and having 2 to about 8 carbon atoms. Desirably, the term alkynyl refers to an alkyl group having 1 or 2 carbon-carbon triple bonds and having 2 to about 6 carbon atoms. Typically, the term "lower" is used to describe alkyl and alkenyl groups which have 6 or fewer carbon atoms.

The terms "substituted alkyl", "substituted alkenyl", and "substituted alkynyl" refer to alkyl, alkenyl, and alkynyl groups, respectively, having one or more substituents including, without limitation, halogen, CN, OH, $NO_2$, amino, aryl, heterocyclic, aryl, alkoxy, aryloxy, alkyloxy, alkylcarbonyl, alkylcarboxy, amino, and arylthio which groups can be optionally substituted. These substituents can be attached to any carbon of an alkyl, alkenyl, or alkynyl group provided that the attachment constitutes a stable chemical moiety.

The term "perfluoroalkyl" as used herein refers to a substituted alkyl group as described above substituted by from one to three fluorine groups. Desirably, the perfluoroalkyl group includes $CH_2F$, $CHF_2$, and $CF_3$ groups.

The term "cycloalkyl" as used herein refers to a cyclic alkyl or hydrocarbon group having 3 to about 10 carbon atoms, and desirably 3 to about 8 carbon atoms. The cycloalkyl group may be optionally substituted with one or more substituents including halogen, CN, OH, $NO_2$, amino, aryl, heterocyclic, aryl, alkoxy, aryloxy, alkyloxy, alkylcarbonyl, alkylcarboxy, amino, and arylthio which groups can be optionally substituted. These substituents can be attached to any carbon of the cycloalkyl group provided that the attachment constitutes a stable chemical moiety.

The term "acyl" as used herein refers to a carbonyl substituent, i.e., a C(O)(R) group where R is a straight- or branched-chain hydrocarbon group including, without limitation, alkyl, alkenyl, and alkynyl groups. Desirably, the R groups have 1 to about 8 carbon atoms, and more preferably 1 to about 6 carbon atoms. The term "substituted acyl" refers to an acyl group which is substituted with 1 or more groups. Desirably, an acyl group can be substituted with halogen, CN, OH, and $NO_2$ groups, among others.

The term "aryl" as used herein refers to an aromatic system which can include a single ring or multiple aromatic rings fused or linked together where at least one part of the fused or linked rings forms a conjugated aromatic system. The aryl groups can include, but are not limited to, phenyl, naphthyl, biphenyl, anthryl, tetrahydronaphthyl, phenanthryl, indene, benzonaphthyl, fluorenyl, and carbazolyl.

The term "substituted aryl" refers to an aryl group which is substituted with one or more substituents including halogen, CN, OH, $NO_2$, amino, alkyl, cycloalkyl, alkenyl, alkynyl, alkoxy, aryloxy, alkyloxy, alkylcarbonyl, alkylcarboxy, alkylamino, and arylthio, which groups can be optionally substituted. Desirably, a substituted aryl group is substituted with 1 to about 4 substituents.

The term "heterocyclic" or "heterocycle" as used herein refers to a stable 4- to 7-membered monocyclic or multicyclic heterocyclic ring which is saturated, partially unsaturated, or wholly unsaturated. The heterocyclic ring has in its backbone carbon atoms and one or more heteroatom including nitrogen, oxygen, and sulfur atoms. Preferably, the heterocyclic ring has 1 to about 4 heteroatoms in the backbone of the ring. When the heterocyclic ring contains nitrogen or sulfur atoms in the backbone of the ring, the nitrogen or sulfur atoms can be oxidized. The term "heterocyclic" or "heterocycle" also refers to multicyclic rings in which a heterocyclic ring is fused to an aryl ring. The heterocyclic ring can be attached to the aryl ring through a heteroatom or carbon atom provided the resultant heterocyclic ring structure is chemically stable.

A variety of heterocyclic groups are known in the art and include, without limitation, oxygen-containing rings, nitrogen-containing rings, sulfur-containing rings, mixed heteroatom-containing rings, fused heteroatom containing rings, and combinations thereof. Oxygen-containing rings include, but are not limited to, furyl, tetrahydrofuranyl, pyranyl, pyronyl, and dioxinyl rings. Nitrogen-containing rings include, without limitation, pyrrolyl, pyrazolyl, imidazolyl, triazolyl, pyridyl, piperidinyl, 2-oxopiperidinyl, pyridazinyl, pyrimidinyl, pyrazinyl, piperazinyl, triazinyl, pyrrolidinyl, and azepinyl rings. Sulfur-containing rings include, without limitation, thienyl and dithiolyl rings. Mixed heteroatom containing rings include, but are not limited to, oxathiolyl, oxazolyl, thiazolyl, oxadiazolyl, oxatriazolyl, dioxazolyl, oxathiazolyl, oxathiolyl, oxazinyl, oxathiazinyl, morpholinyl, thiamorpholinyl, thiamorpholinyl sulfoxide, oxepinyl, thiepinyl, and diazepinyl rings. Fused heteroatom-containing rings include, but are not limited to, benzofuranyl, thionapthene, indolyl, benzazolyl, purindinyl, pyranopyrrolyl, isoindazolyl, indoxazinyl, benzoxazolyl, anthranilyl, benzopyranyl, quinolinyl, isoquinolinyl, benzodiazonyl, napthylridinyl, benzothienyl, pyridopyridinyl, benzoxazinyl, xanthenyl, acridinyl, and purinyl rings.

The term "substituted heterocyclic" or "substituted heterocycle" as used herein refers to a heterocyclic group having one or more substituents including halogen, CN, OH, $NO_2$, amino, alkyl, cycloalkyl, alkenyl, alkynyl, alkoxy, aryloxy, alkyloxy, alkylcarbonyl, alkylcarboxy, alkylamino, and arylthio, which groups can be optionally substituted. Preferably, a substituted heterocyclic group has 1 to about 4 substituents.

The term "aroyl" as used herein refers to a carbonyl substituent bound to a phenyl or heterocyclic group. Preferably, the aroyl heterocyclic groups include 2-pyridinyl, 3-pyridinyl, 2-furanyl, 3-furanyl, 3-thiophenyl, 2-pyrimidinyl, and 4-pyrimidinyl groups. The term "substituted aroyl" refers to an aroyl group which is substituted with 1 or more groups including, without limitation, halogen, CN, OH, and $NO_2$.

The term "thioalkoxy" as used herein is used interchangeably with the term "thioalkyl", with both referring to an S(alkyl) group, where the point of attachment is through the sulfur-atom and the alkyl group can be optionally substituted.

The term "arylthio" as used herein refers to the S(aryl) group, where the point of attachment is through the sulfur-atom and the aryl group can be optionally substituted.

The term "alkoxy" as used herein refers to the O(alkyl) group, where the point of attachment is through the oxygen-atom and the alkyl group is optionally substituted.

The term "aryloxy" as used herein refers to the O(aryl) group, where the point of attachment is through the oxygen-atom and the aryl group is optionally substituted.

The term "alkylcarbonyl" as used herein refers to the C(O)(alkyl) group, where the point of attachment is through the carbon-atom of the carbonyl moiety and the alkyl group is optionally substituted.

The term "alkylcarboxy" as used herein refers to the C(O)O(alkyl) group, where the point of attachment is through the carbon-atom of the carboxy moiety and the alkyl group is optionally substituted.

The term "amino" as used herein refers to a $NH_2$ group.

The term "aminoalkyl" as used herein refers to both secondary and tertiary amines where the point of attachment is through the nitrogen-atom and the alkyl groups are optionally substituted. The alkyl groups can be the same or different.

The term "halogen" refers to Cl, Br, F, and I groups.

The term "sulfonyl" as used herein refers to the $S(O)_2R$ group wherein R is any substituent that can form a bond to the sulfur atom group, provided that the bond constitutes a stable chemical moiety. Desirably, the R group is an optionally substituted alkyl group.

The compounds of the present invention can encompass tautomeric forms of the structures provided herein characterized by the bioactivity of the drawn structures. Further, the compounds of the present invention can be used in the form of salts derived from pharmaceutically or physiologically acceptable acids, bases, alkali metals and alkaline earth metals.

Physiologically acceptable acids include those derived from inorganic and organic acids. A number of inorganic acids are known in the art and include hydrochloric, hydrobromic, hydroiodic, sulfuric, nitric, and phosphoric acids, among others. Similarly, a variety of organic acids are known in the art and include, without limitation, lactic, formic, acetic, fumaric, citric, propionic, oxalic, succinic, glycolic, glucuronic, maleic, furoic, glutamic, benzoic, anthranilic, salicylic, tartaric, malonic, mallic, phenylacetic, mandelic, embonic, methanesulfonic, ethanesulfonic, panthenoic, benzenesulfonic, toluenesulfonic, stearic, sulfanilic, alginic, and galacturonic acids, among others.

Physiologically acceptable bases include those derived from inorganic and organic bases. A number of inorganic bases are known in the art and include aluminum, calcium, lithium, magnesium, potassium, sodium, and zinc sulfate or phosphate compounds, among others. A number of organic bases are known in the art and include, without limitation, N,N-dibenzylethylenediamine, chloroprocaine, choline, diethanolamine, ethylenediamine, meglumine, and procaine, among others.

Physiologically acceptable alkali salts and alkaline earth metal salts include, without limitation, sodium, potassium, calcium and magnesium salts in the form of esters, and carbamates.

These salts, as well as other compounds of the invention can be in the form of esters, carbamates and other conventional "pro-drug" forms, which, when administered in such form, convert to the active moiety in vivo. In one embodiment, the prodrugs are esters. See, e.g., B. Testa and J. Caldwell, "Prodrugs Revisited: The "Ad Hoc" Approach as a Complement to Ligand Design", Medicinal Research Reviews, 16(3):233-241, ed., John Wiley & Sons (1996).

As described herein, the compounds of formula I and/or salts, prodrugs or tautomers thereof, are delivered alone and/or in regimens as described herein and can include the delivery of other active agents.

The compounds discussed herein also encompass "metabolites" which are unique products formed by processing the compounds of the invention by the cell or patient. Preferably, metabolites are formed in vivo.

II. Methods of Preparing the Compounds of the Invention

The compounds of this invention can be prepared following the Schemes illustrated below.

As illustrated in Scheme I, compounds 4 and 5 can be prepared by employing coupling reactions. A substituted ortho-amino benzoic acid or a derivative thereof can be treated with an organometallic reagent in a nonprotic solvent to give ortho-amino carbinol 2 under an inert atmosphere such as argon or nitrogen at about −78° C. to about room temperature. A variety of ortho-amino benzoic acids can be utilized and include ethyl esters, among others. Such ortho-amino acids are substituted with a leaving group (X) such as Br, I, Cl, or a latent coupling precursor, such as an alkoxy group, which can be converted into another leaving group, such as an Otriflate (OTf) group. The organometallic reagent utilized in the coupling can be a Grignard reagent, among others. Nonprotic solvents can include ethers such as tetrahydrofuran (THF) or diethyl ether, among others. Typically, the reaction is executed at temperatures less than about room temperature and desirably at a temperature of about −78° C. to about room temperature.

Ring closure of carbinol 2 to yield benzoxazin-2-one 3 can be performed using a condensing agent in a nonprotic solvent. A variety of condensing agents are known in the art and include, without limitation, carbonyldiimidazole (CDI), phosgene, dimethylcarbonate, or diethylcarbonate. Typically, the nonprotic solvent is THF. Desirably, ring closure is performed at about room temperature to about 65° C.

Arylation of benzoxazin-2-one 3 to yield 4 is performed by coupling using a transition metal catalyst. Typically, the transition metal catalyst is a palladium or nickel complex and can contain phosphino ligands. Examples of phosphino ligands that can be used include triphenylphosphine ($Ph_3P$), diphenylphosphinoferrocene (dppf), diphenylphosphinoethane (dppe), dibenzylideneacetone (dba), or 2,2'-Bis(diphenylphosphino)-1,1'-binaphthyl (BINAP), among others. Alternatively, the transition metal catalyst is a palladium salt including palladium acetate. Typically, the coupling is performed by coupling a substituted nucleophilic reagent with the 6-halo-benzoxazinone 3 in a solvent, optionally in the presence of a base, to give the compound 4. The nucleophilic reagent can be an aniline or phenol, among others. Bases that can be used in the coupling include, but are not limited to, sodium t-butoxide, cesium carbonate, potassium phosphate, or cesium fluoride. Solvents can include, without limitation, benzene, dimethylformamide (DMF), isopropanol, ethanol, dimethoxyethane (DME), ether, acetone or a mixtures thereof. The coupling reaction is generally performed under an inert atmosphere such as nitrogen or argon at temperatures from about room temperature to about 120° C.

Alkylation of the 1-position to give compound 5 can be performed using an alkylating reagent, optionally in the presence of a base in a nonprotic solvent. Typically, the alkylating reagent is an alkyl iodide, among others. Suitable bases can include sodium hydride or sodium methoxide, among others, in a nonprotic solvent including, but not limited to, THF, dimethylformamide (DMF), or dimethylsulfoxide (DMSO). Typically, the alkylation is performed at temperatures from about 0° C. to about room temperature under an inert atmosphere of argon or nitrogen.

Scheme I

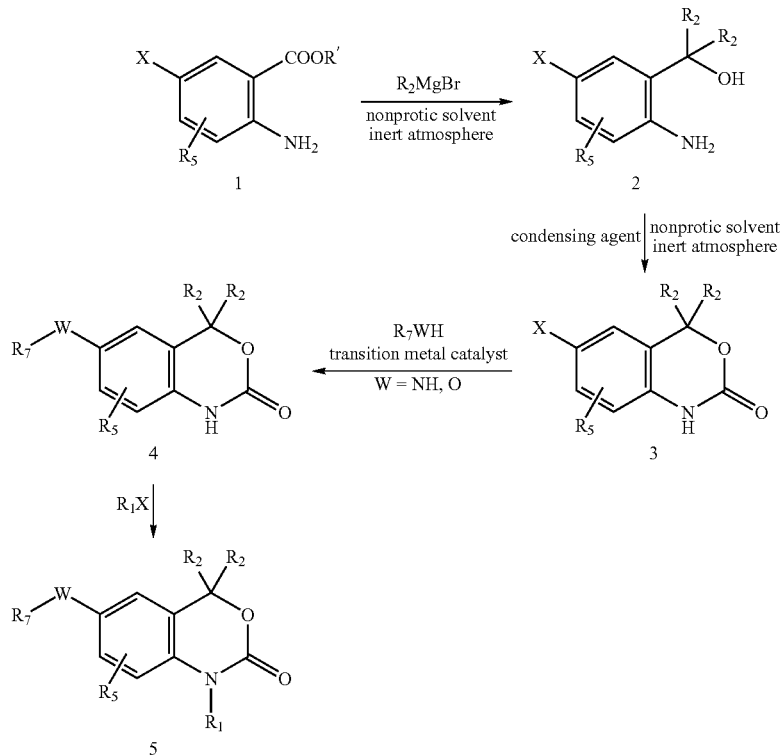

As illustrated in Scheme II, benzoxazinone 3 can also be converted to a nucleophile such as boronic acid 6. Desirably, benzoxazinone 3 can first be combined with an organometallic reagent in a nonprotic solvent, followed by quenching using an electrophile to form 6. A variety of organometallic reagents can be utilized and include n-BuLi, among others. Typically, the nonprotic solvent is THF or diethyl ether, among others. Electrophiles that can be utilized include, without limitation, borates, including, for example, trimethyl borate or triisopropyl borate.

Alkylation of 6 at the 1-position to form boronic acid 7 can be performed using an alkylating reagent. A variety of alkylating reagents can be utilized and include, without limitation, alkyl halides such as an alkyl bromide or alkyl iodide. Alkylation of 6 is typically performed at temperatures of about −78° C. to about room temperature under an inert atmosphere of argon or nitrogen.

Using a copper mediated coupling reaction, a substituted aniline or phenol can be coupled with boronic acid 7 in the presence of a base in a nonprotic solvent at room temperature under an inert atmosphere of argon or nitrogen, to give compound 5. Typically, the base is a trialkyl amine including, without limitation, triethyl amine; the copper reagent is copper acetate, among others; and the nonprotic solvent is methylene chloride, among others.

Scheme II

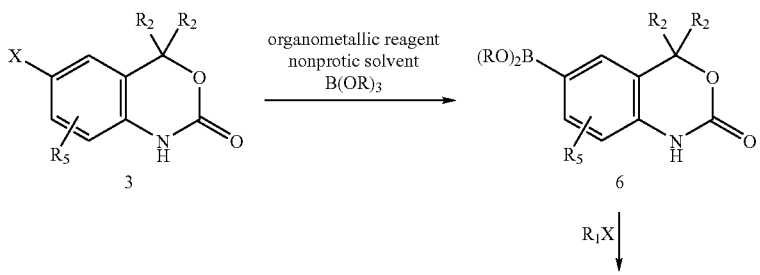

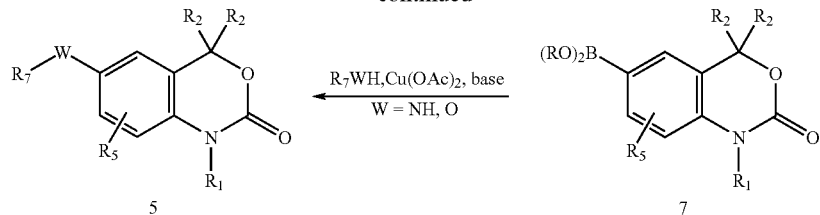

As illustrated in Scheme III, 7 can also be oxidized to give 6-hydroxyl benzoxazinone 8, i.e., the phenolic precursor, at about room temperature. Oxidation is typically performed using an oxidizing reagent including, but not limited to, hydrogen peroxide or 3-chloroperoxybenzoic acid, in a solvent. Typically, the solvent is dichloromethane, among others. The phenolic precursor 8 can then be converted to compound 5 by coupling using either palladium or copper mediated coupling reactions as described above.

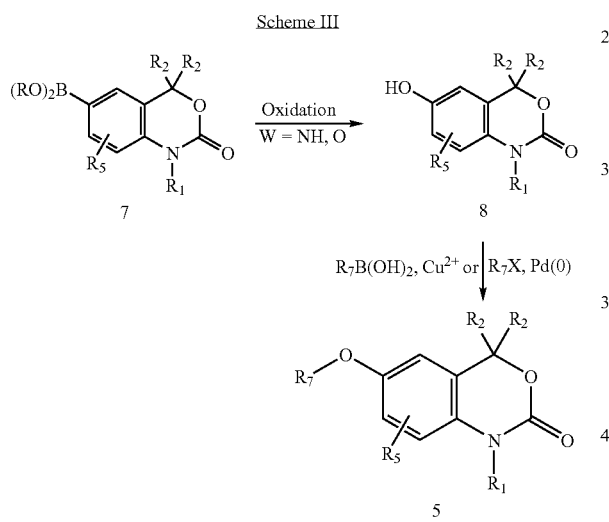

Scheme IV describes an alternative approach to preparing 6-arylamino benzoxazinone 5. In this alternative approach, intermediate benzoxazinone 11 is prepared from compound 9 following a similar procedure as described in Scheme I.

Nitration of 11 at the 6-position then affords 6-nitrobenzoxazinone 12 using a nitrating agent in a solvent. Preferably, the nitrating agent is concentrated nitric acid, among others, and the solvent is a mixture of acetic acid and concentrated sulfuric acid, among others. 6-nitrobenzoxazinone 12 can be alkylated using an alkylating reagent, as previously described, to prepare 13. The 6-nitro group of 13 can then be reduced using a reducing agent in a protic solvent to form 6-aminobenzoxazinone 14. A variety of reducing agents are known in the art and include sodium borohydride or hydrogen in the presence of a catalyst including palladium on carbon, among others. Protic solvents that can be used in the reduction step include alcohols such as methanol, among others.

6-aminobenzoxazinone 14 can then be coupled with an aryl halide or aryl boronic acid to prepare 5 using the palladium or copper mediated coupling procedures as previously described.

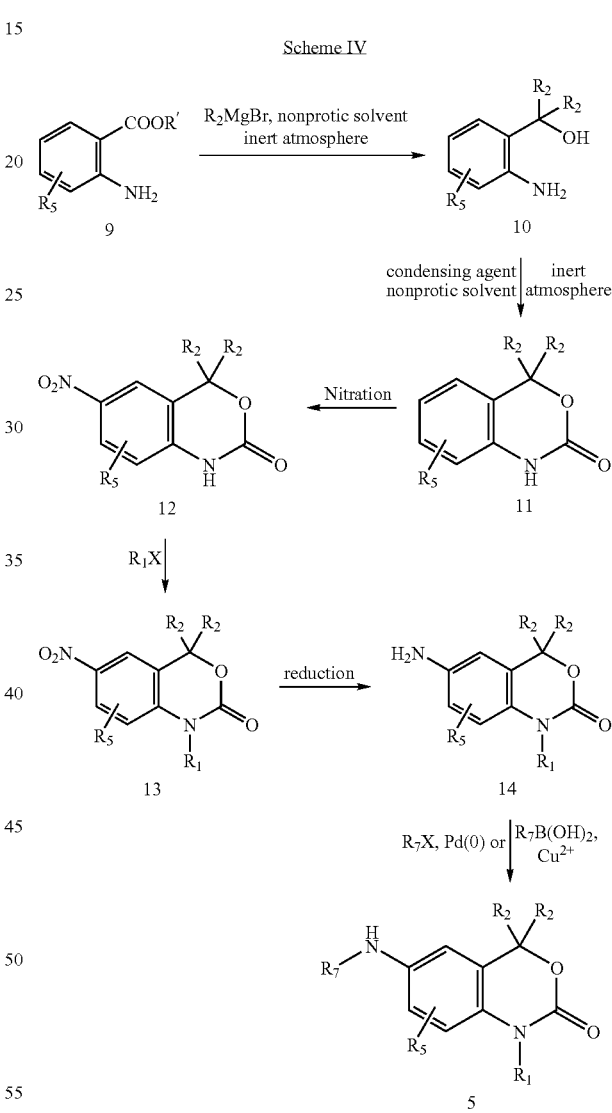

As illustrated in Scheme V, sulfonate 15 can be prepared by combining 6-hydroxyl benzoxazinone 8 with an aryl sulfonyl reagent in the presence of a base. Typically, the aryl sulfonyl reagent is, without limitation, an aryl sulfonyl halide or aryl sulfonyl anhydride and the base is Hünig's base, a trialkyl amine including, but not limited to, triethylamine, pyridine, or potassium hydroxide in a solvent such as methylene chloride, pyridine, water, or THF, among others.

Sulfonamide 16 can be similarly prepared using 6-aminobenzoxazinone 14 and a similar procedure as described for the preparation of sulfonate 15.

Scheme V

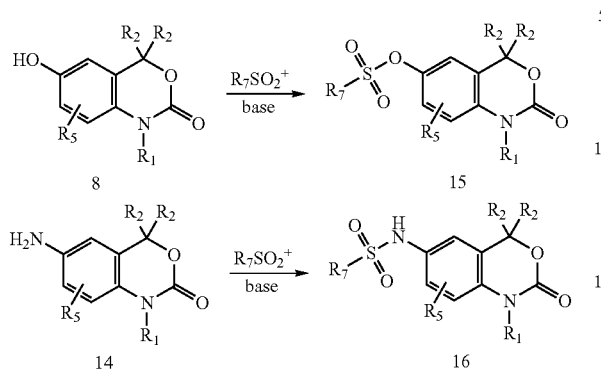

Scheme VI illustrates an alternative approach to prepare benzoxazinone 3. Accordingly, aniline 1 is protected in a solvent, optionally in the presence of a base either as a catalyst or as an acid scavenger. Typically, the protecting group is an alkoxy carbonyl protecting group including, but not limited to, allenoxy carbonyl, t-butoxy carbonyl, benzoxy carbonyl, ethoxy carbonyl, or methoxy carbonyl. Suitable solvents include, without limitation, THF and acetonitrile.

The protected aniline is then treated with an organometallic reagent, such as that utilized in the preparation of 2, to give the carbinol 17. Suitable organometallic reagents include, without limitation, organolithium or Grignard reagents.

Treatment of 17 with a base in a solvent under an inert atmosphere of nitrogen or argon at a temperature of about room temperature to about the boiling point of the solvent affords benzoxazinone 3. Typically, the base is potassium t-butoxide, n-butyl lithium, or potassium hydroxide, among others. The solvent desirably includes toluene, THF, or alcohol, among others.

Scheme VI

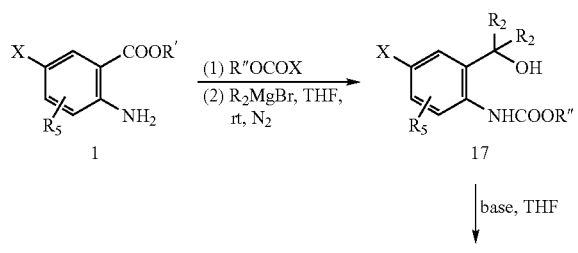

-continued

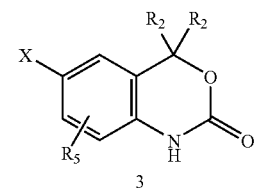

Scheme VII describes one preparation of benzoxazinone 22 having two different substituents at the 4-position. Accordingly, isatoic anhydride 18 can be combined with N-, O-dimethylhydroxyl-amine hydrochloride salt (NHOMe-Me.HCl) in a protic solvent at reflux under an inert atmosphere such as argon or nitrogen to form Weinreb amide 19. The protic solvents can include, without limitation, alcohols such as ethanol or isopropanol.

Treatment of amide 19 with organometallic compounds under an inert atmosphere such as argon or nitrogen at about −78° C. to about room temperature forms amino ketone 20. A variety of organometallic compounds can be utilized to form ketone 20 and include, but are not limited to, alkyllithium, alkynyllithium, and aryllithium reagents, or their Grignard counterpart in nonprotic solvents including ethers such as THF or diethyl ether, among others.

Ketone 20 can be converted into carbinol 21 by combining 20 with an organometallic reagent as described above under an inert atmosphere such as argon or nitrogen at about −78° C. to about room temperature. Alternatively, carbinol 21 can be prepared by reducing 20 using a reducing reagent in a solvent under an inert atmosphere in the temperature ranging from 0° C. to the boiling point of the solvent. A variety of reducing agents is known in the art and includes lithium aluminum hydride or sodium borohydride, among others. The solvent can include, without limitation, THF, ether, or anhydrous alcohol.

Ring closure of carbinol 21 to yield 22 can be accomplished using condensing agents in a nonprotic solvent. A variety of condensing agents is known and includes, without limitation, carbonyldiimidazole, phosgene, dimethylcarbonate, or diethylcarbonate. Temperatures of about room temperature to about 65° C. can be utilized.

Scheme VII

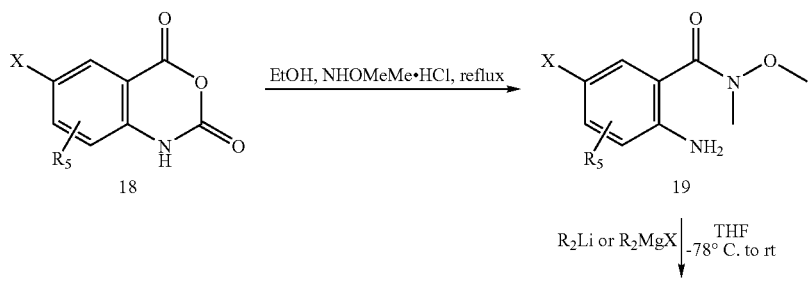

-continued

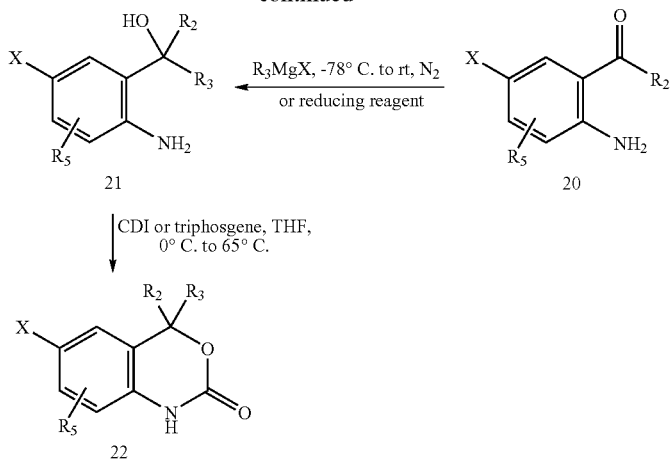

Alternatively, as illustrated in Scheme VIII, amino ketone 20 can be prepared by treatment of benzonitrile 23 in a solvent with an organometallic reagent including, without limitation, organolithium reagents or Grignard reagents under an inert atmosphere such as argon or nitrogen at temperatures ranging from about −78° C. to about room temperature. Solvents that can be used include ethers such as THF or diethyl ether, among others.

Scheme VIII

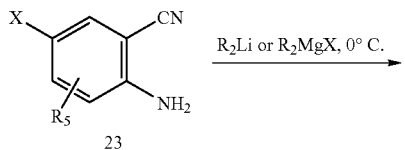

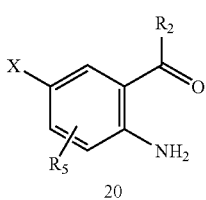

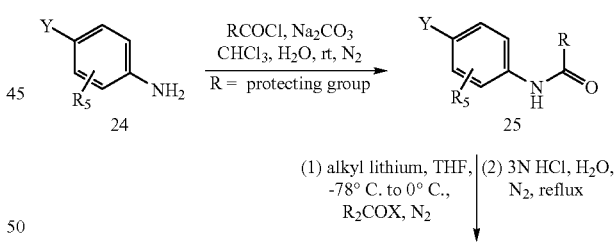

Scheme IX depicts the preparation of ortho-amino ketone 26, where $R_2$ is a low perfluoroalkyl including a trifluoromethyl group. Specifically, substituted aniline 24 can be protected with a protecting group to give protected aniline 25 under an inert atmosphere such as argon or nitrogen at temperatures ranging from about 0° C. to about 70° C. Such protecting groups can include pivaloyl chloride or di-tert-butyl pyrocarbonate, among others. Protection can be performed in a solvent such as acetonitrile, acetone, THF, methylene chloride, chloroform, water, or mixtures thereof, among others. Desirably, the mixture includes methylene chloride and water. A base such as sodium carbonate, sodium bicarbonate, or potassium carbonate, among others, is added when an acid, such as hydrochloride, is produced as a side-product.

Protected aniline 25 can then be treated with an alkyl-lithium reagent, including, without limitation, n-butyl-lithium or s-butyllithium, under an inert atmosphere such as argon or nitrogen at about −78° C. to about room temperature. A low perfluorocarboxy derivative, including, trifluoroacetyl chloride, 1-(trifluoroacetyl)-imidazole, or ethyl trifluoroacetate in a nonprotic solvent such as, but not limited to, ether or THF can then be added to give the protected ortho-amino ketone. Subsequent removal of the protecting group to give 26 can be performed using an acid in a solvent including, without limitation, methylene chloride or water at about 0° C. to about the boiling point of the solvent. Suitable acids that can be used include trifluoroacetic acid (TFA) or an aqueous hydrochloride solution, preferably a 3 N aqueous hydrochloride solution. Converting ketone 26 to the compounds of present invention can be performed using the procedures noted above.

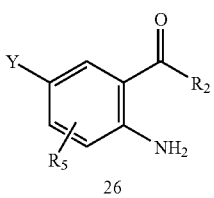

As described in Scheme X, 6-substituted benzoxazin-2-one can be converted to the 6-substituted benzoxazin-2-thione 27. Typically, benzoxazin-2-one is treated with a sulfur reagent in a nonprotic solvent such as, but not limited to, o-xylene, chlorobenzene, or toluene under an inert atmosphere such as argon or nitrogen at reflux. Suitable sulfur reagents can include Lawesson's reagent, among others.

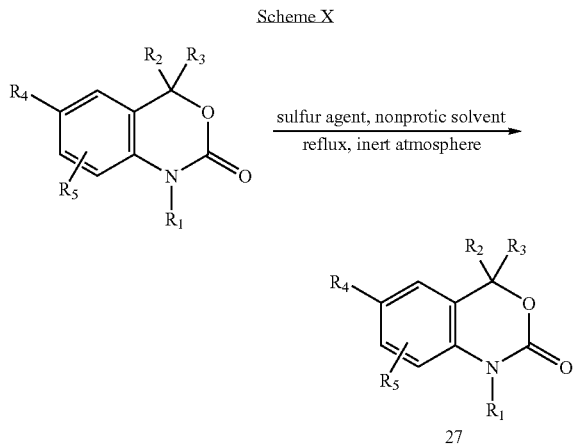

III. Formulations of the Invention

The compounds of formula I as described herein can be formulated in any form suitable for the desired route of delivery using a pharmaceutically effective amount of one or more of the compounds of formula I. For example, the compositions of the invention can be formulated for delivery by oral, dermal, transdermal, intrabronchial, intranasal, intravenous, intramuscular, subcutaneous, parenteral, intraperitoneal, intranasal, vaginal, rectal, sublingual, intracranial, epidural, and intratracheal routes, or by sustained release. Preferably, delivery is oral.

A pharmaceutically effective amount of the compound(s) used according to the present invention can vary depending on the specific compound(s), mode of delivery, and any other active ingredients used in the formulation. The dosing regimen can be adjusted to provide the optimal therapeutic response. Several divided doses can be delivered daily, e.g., in divided doses 2 to 4 times a day, or a single dose can be delivered. The dose can however be proportionally reduced or increased as indicated by the exigencies of the therapeutic situation.

Preferably, the delivery can be on a daily, weekly, or monthly basis, and more preferably on a daily delivery. Daily dosages can be lowered or raised based on the periodic delivery.

The compounds of formula I can be delivered at a daily dosage of from about 0.5 to about 500 mg. Desirably, the compound can be delivered at a daily dosage of from about 1 to about 100 mg, more desirably about 2 to about 80 mg, and even more desirably about 2 to about 50 mg.

The compounds of formula I can be combined with one or more pharmaceutically acceptable carriers or excipients including, without limitation, solid and liquid carriers which are compatible with the compositions of the present invention. Such carriers can include adjuvants, syrups, elixirs, diluents, binders, lubricants, surfactants, granulating agents, disintegrating agents, emollients, and combinations thereof. Typically, the compound is present at about 25 to about 90%, by weight and more desirably between about 5% and 60% by weight of the formulation.

Adjuvants can include, without limitation, flavoring agents, coloring agents, preservatives, and supplemental antioxidants, which can include vitamin E, ascorbic acid, butylated hydroxytoluene (BHT) and butylated hydroxyanisole (BHA).

Elixers and/syrups can be prepared from acceptable sweeteners such as sugar, saccharine or a biological sweetener, a flavoring agent, and/or solvent. In one embodiment, a syrup can contain about 10 to about 50% of a sugar carrier. In another embodiment, the elixir can contain about 20 to about 50% of an ethanol carrier.

Diluents can include materials in which the compound can be dispersed, dissolved, or incorporated. Preferably, the diluents include water, lower monovalent alcohols, non-ionic surfactants, and low molecular weight glycols and polyols, including propylene glycol, diethylene glycol, polyethylene glycol, polypropylene glycol, glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers, oils such as corn, peanut and sesame oils, dimethylsulfoxide (DMSO), dimethylformamide (DMF), and combinations thereof. Preferably, the diluent is water.

Desirably, solutions or suspensions of these compounds of the invention as free bases or pharmacologically acceptable salts can be prepared in water and one or more of a surfactant, including hydroxypropylcellulose, among others.

Binders can include, without limitation, cellulose, methylcellulose, hydroxymethylcellulose, polypropylpyrrolidone, polyvinylpyrrolidone, gelatin, gum arabic, polyethylene glycol, starch, sugars such as sucrose, kaolin, and lactose, among others.

Lubricants can include magnesium stearate, light anhydrous silicic acid, talc and sodium lauryl sulfate, among others.

Granulating agents can include, without limitation, silicon dioxide, microcrystalline cellulose, starch, calcium carbonate, pectin, crospovidone, and polyplasdone, among others.

Disintegrating agents can include starch, carboxymethylcellulose, hydroxypropylstarch, substituted hydroxypropylcellulose, sodium bicarbonate, dicalcium phosphate, and calcium citrate, among others.

Emollients can include, without limitation, stearyl alcohol, mink oil, cetyl alcohol, oleyl alcohol, isopropyl laurate, polyethylene glycol, olive oil, petroleum jelly, palmitic acid, oleic acid, and myristyl myristate.

IV. Therapeutic Regimens

The present invention provides dosing regimens utilizing the compound(s) of formula I with a physiologically acceptable carrier. The compositions of the invention can be delivered by a route such as oral, dermal, transdermal, intrabronchial, intranasal, intravenous, intramuscular, subcutaneous, parenteral, intraperitoneal, intranasal, vaginal, rectal, sublingual, intracranial, epidural, intratracheal, or by sustained release. Preferably, delivery is oral.

In one embodiment, the compounds are delivered orally by tablet, capsule, microcapsules, dispersible powder, granule, suspension, syrup, elixir, and aerosol. Desirably, when the compositions are delivered orally, delivery is by tablets and hard- or liquid-filled capsules.

In another embodiment, the compounds are delivered intravenously, intramuscularly, subcutaneously, parenterally and intraperitoneally in the form of sterile injectable solutions, suspensions, dispersions, and powders which are fluid to the extent that easy syringe ability exits. Such injectable compositions are sterile, stable under conditions of manufacture and storage, and free of the contaminating action of microorganisms such as bacteria and fungi.

Injectable formations can be prepared by combining the compound with a liquid. The liquid can be selected from among water, glycerol, ethanol, propylene glycol and polyethylene glycol, oils, and mixtures thereof, and more preferably the liquid carrier is water. In one embodiment, the oil is vegetable oil. Optionally, the liquid carrier contains a suspending agent. In another embodiment, the liquid carrier is an isotonic medium and contains 0.05 to about 5% suspending agent.

In a further embodiment, the compounds are delivered rectally in the form of a conventional suppository.

Dispersible formulations can be prepared by combining the compounds of the invention with glycerol, liquid, polyethylene glycols and mixtures thereof in oils.

In another embodiment, the compounds are delivered vaginally in the form of a conventional suppository, cream, gel, ring, or coated intrauterine device (IUD).

In yet another embodiment, the compositions are delivered intranasally or intrabronchially in the form of an aerosol.

In a further embodiment, the compounds are delivered transdermally or by sustained release through the use of a transdermal patch containing the composition and an optional carrier that is inert to the compound, is nontoxic to the skin, and allows for delivery of the compound for systemic absorption into the blood stream. Such a carrier can be a cream, ointment, paste, gel, or occlusive device. The creams and ointments can be viscous liquid or semisolid emulsions. Pastes include absorptive powders dispersed in petroleum or hydrophilic petroleum. Further, a variety of occlusive devices can be utilized to release the active reagents into the blood stream and include semi-permeable membranes covering a reservoir contain the active reagents, or a matrix containing the reactive reagents.

The use of sustained delivery devices can be desirable, in order to avoid the necessity for the patient to take medications on a daily basis. The term "sustained delivery" is used herein to refer to delaying the release of an active agent, i.e., a compound of the invention, until after placement in a delivery environment, followed by a sustained release of the agent at a later time. A number of sustained delivery devices are known in the art and include hydrogels (U.S. Pat. Nos. 5,266,325; 4,959,217; 5,292,515), osmotic pumps (U.S. Pat. Nos. 4,295,987 and 5,273,752 and European Patent No. 314,206, among others); hydrophobic membrane materials, such as ethylenemethacrylate (EMA) and ethylenevinylacetate (EVA); bioresorbable polymer systems (International Patent Publication No. WO 98/44964 and U.S. Pat. Nos. 5,756,127 and 5,854,388); and other bioresorbable implant devices composed of, for example, polyesters, polyanhydrides, or lactic acid/glycolic acid copolymers (U.S. Pat. No. 5,817,343). For use in such sustained delivery devices, the compounds of the invention can be formulated as described herein. See, U.S. Pat. Nos. 3,845,770; 3,916,899; 3,536,809; 3,598,123; and 4,008,719.

In yet another embodiment, the compounds are topically delivered using a topical vehicle including creams, pastes, gels, ointments, lotions, liquids, solutions, suspensions, or foams or can be alone delivered prior or subsequent to the topical vehicle. Preferably, the topical vehicles are anti-comedogenic.

Skin conditioning agents can be applied prior to, concurrently with, or subsequent to the compounds of the invention. Such skin conditioning agents typically include reagents that provide a conditioning effect to the skin and/or do not clog the pores of the skin. A number of skin conditioning agents are known in the art and include, without limitation, skin conditioning agents that can be applied to the skin, including water-based lotions, creams, pastes, gels, ointments or foams.

Optionally, other conventional acne-reducing compounds are included in the compositions and/or regimens of the invention. Such acne-reducing compounds can assist in the reduction of redness and/or blemishes. A large number of acne-reducing compounds are known in the art and include carotenoid agents, vitamin B sources, zinc compounds, and combinations thereof. See, U.S. Pat. No. 5,962,517.

Carotenoid agents can be included in the composition of the invention or can be alone delivered prior or subsequent to the compound or composition and include those carotenoids which exhibit antioxidant behavior. Preferably, the carotenoid agent includes beta-carotene, canthaxanthin, zeaxanthin, lycopen, lutein, crocetin, capsanthin, and vitamin A sources. The vitamin A sources can include vitamin A acetate or vitamin A palmitate. More preferably, the carotenoid agent is beta-carotene.

Vitamin B sources can also be included in the composition of the invention or can be alone delivered prior or subsequent to the composition to assist or promote the formation of amino acids and collagen. Preferably, the vitamin B source is a $B_6$ source, which can include, without limitation, pyridoxine, pyridoxal, and pyridoxamine, and more preferably is pyridoxine.

Further, zinc compounds can be included in the composition of the present invention or can be alone delivered prior or subsequent to the composition. The zinc compound can include any zinc compound, preferably a zinc compound which promotes the reduction of inflammation, more preferably zinc ascorbic acid or zinc ascorbate, and most preferably zinc ascorbate.

Penetration enhancers, when used according to the method of the invention in treating hirsutism, can include any reagent that enhances the penetration of a compound through one or more layers of the skin and/or to the site of the skin disorder. A number of penetration enhancers are known in the art and include, but are not limited to, urea, propan-2-ol, polyoxyethylene ethers, terpenes, cis-fatty acids, including oleic acid and palmitoleic acid, acetone, laurocapram dimethyl sulfoxide, 2-pyrrolidone, oleyl alcohol, glyceryl-3-stearate, cholesterol, myristic acid isopropyl ester, propylene glycol, and combinations thereof.

The regimens of the invention can include the continuous delivery of the compounds of the invention. In another embodiment, the regimens can include the periodic discontinuation of delivery of the compounds of the invention. Such periodic discontinuation can include delivery of a placebo during the period of time where the compounds of the invention are not delivered to the patient. Alternatively, no placebo or active agent is delivered to the patient when the compounds are not being delivered to the patient.

By the term "placebo" or "inactive agent" is meant a reagent having pharmacological properties that are not relevant to the condition being treated, i.e., does not contain an active agent. Typical placebos include sugar as the primary constituent.

By the term "active agent" is meant any reagent which assists in treating a hormone-related condition.

The method of the present invention can be carried out over a cycle of 21 or more days, preferably 21 or more consecutive days, more preferably 21, 28, 30, or 31 days, and most preferably 21 or 28 days. One of skill in the art would readily be able to select and adjust the appropriate period of delivery.

The terminal portion of a cycle can be the last 1 to about 10 days of the cycle, and preferably the last 7 days of the cycle. In one embodiment, the terminal portion of the 28-day cycle can include the last 7 days of the cycle, i.e., days 22 to 28 of the 28-day cycle. The terminal portion of a cycle can include the delivery of an agent other than the compositions of the invention and is preferably a placebo. Alternatively, no agent or placebo is delivered during the terminal portion of the cycle.

The regimen can include delivering a daily dosage of the compound of formula I, which is incorporated into a single daily dosage unit. Delivery of the compounds of formula I can be prior to, simultaneous with, or subsequent to the delivery of other reagents that can be used according to the present invention.

The regimen can further include alternating delivery of the compounds of formula I alone, other reagent(s) that can be used according to the present invention, and a combination of the compound and the other reagent(s).

In one embodiment, a single daily dosage of the compound of formula I can be delivered for the entire 21-day, 28-day, 30-day, or 31-day cycle. Alternatively, a single daily dosage of the compound of formula I can be delivered for the first 21 days of a 28-day, 30-day, or 31-day cycle. A single daily dosage of the compound of formula I can also be delivered for the first 24 days of a 28-day, 30-day, or 31-day cycle.

The regimen can further include co-delivering the compounds of the invention with an estrogen. When included in the compositions of the present invention, the estrogens can include natural estrogens, synthetic estrogens, catechol estrogens, conjugated estrogens, and non-steroidal estrogens, among others, or pharmaceutically acceptable salts or esters thereof. In one embodiment, the estrogen is a natural estrogen including estrone, including the acetate, propionate, sulfate, and sulfate piperazine ester salts; estradiol, including the 3-benzoate, 17b-cypionate, 17-propionate, d-propionate, hemisuccinate, 17-heptanotate, 17-undecanoate, and 17-valerate ester salts; or estriol. In another embodiment, the estrogen is a synthetic estrogen including ethinyl estradiol. In a further embodiment, the estrogen is a conjugated estrogen including conjugated equine estrogens and sodium estrone sulfate and is available in formulations for intravenous, intramuscular, and topical administration (Wyeth). In a further embodiment, the estrogen is a catechol estrogen including 2- or 4-hydroxyestrogens. In yet another embodiment, the nonsteroidal estrogen is diethylstilbestrol. See, Chapter 50 entitled "Hormones" in Remington's Pharmaceutical Sciences, $18^{th}$ Ed., Mack Publishing Company, Easton, Pa., 1990. The desired estrogen may however be selected from a variety of products commercially available. One of skill in the art would readily be able to select the estrogen, as well as dosage, that achieves the desired effect. Preferably, the estrogen is present in the formulation at about 0.01 mg to about 1.0 mg.

One regimen of the invention can include alternating delivery of the compounds of formula I alone, an estrogen alone, and a combination of the compound and the estrogen. The regimen can also include the delivery of another reagent prior to, in conjunction with, or subsequent to the compound of formula I and the estrogen.

In one embodiment, a single combined daily dosage of the compound of formula I and an estrogen can be delivered for the entire 21-day, 28-day, 30-day, or 31-day cycle. Alternatively, a single combined daily dosage of the compound of formula I and an estrogen can be delivered for the first 21 days of a 28-day, 30-day, or 31-day cycle. A single combined daily dosage of the compound of formula I and an estrogen can also be delivered for the first 24 days of a 28-day, 30-day, or 31-day cycle.

In a further embodiment, a daily dosage of the compound of formula I can be delivered by one route of delivery and a daily dosage of an estrogen can be delivered by a second route of delivery for the entire 21-day, 28-day, 30-day, or 31-day cycle. Alternatively, a daily dosage of the compound of formula I can be delivered by one route of delivery and a daily dosage of an estrogen can be delivered by a second route of delivery for the first 21 days of a 28-day, 30-day, or 31-day cycle. Further, a daily dosage of the compound of formula I can be delivered by one route of delivery and a daily dosage of an estrogen can be delivered by a second route of delivery for the first 24 days of a 28-day, 30-day, or 31-day cycle.

In another embodiment, a daily dosage of the compound of formula I can be delivered, followed by a daily dosage of an estrogen for the entire 21-day, 28-day, 30-day, or 31-day cycle. Alternatively, a daily dosage of the compound of formula I can be delivered, followed by a daily dosage of an estrogen for the first 21 days of a 28-day, 30-day, or 31-day cycle. Alternatively, a daily dosage of the compound of formula I can be delivered, followed by a daily dosage of an estrogen for the first 24 days of a 28-day, 30-day, or 31-day cycle.

In a further embodiment, the compounds of formula I are delivered with an estrogen for the first 14 to 24 days of a 28-day cycle, followed by delivery of the estrogen alone for a period of 1 to 11 days beginning on any cycle day between day 14 and 24.

In another embodiment, the compounds of formula I can be delivered for the initial 18 to 21 days of a 28-day cycle, followed by delivery of an estrogen alone for from 1 to 7 days.

In yet a further embodiment, the compounds of formula I can be delivered alone over a 28 day cycle for the first 21 days, followed by delivery of an estrogen alone from day 22 to day 24.

The compounds of the invention can also be delivered to a patient with one or more of a selective estrogen receptor modulator (SERM). Typically, the patient is a female of child-bearing age. The exact SERM utilized is dependent upon the patient being treated, condition being treated, and severity of the condition, among other factors.

A variety of SERMS are known in the art and include, without limitation, EM-800, EM-652, raloxifene hydrochloride, arzoxifene, lasofoxifene, droloxifene, tamoxifene, tamoxifene citrate, 4-hydroxytamoxifen citrate, clomiphene citrate, toremifene citrate, pipendoxifene, idoxifene, levormeloxifene, centchroman, nafoxidene, and bazedoxifene.

The effective dosage of the SERM employed can vary depending on the particular compound employed, the mode of administration and the severity of the condition being treated. However, in general, satisfactory results are obtained when the SERMS are administered at a daily dosage of from about 0.2 to about 100 mg/kg of animal body weight, preferably given in divided doses two to four times a day, or in a sustained release form. Preferably, the amount of SERM utilized according to the present invention is preferably at least 0.2 mg per day, more preferably from about 0.2 mg to about 200 mg per day, and most preferably from about 0.2 mg to about 100 mg per day. Several divided doses can be administered daily or the dose can be proportionally reduced as indicated by the exigencies of the therapeutic situation.

Typically, a composition containing a pharmaceutically effective amount of a compound of formula I and a pharmaceutically effective amount of a SERM is delivered in a regimen to a female of child-bearing age. In one embodiment, the compound of formula I and SERM are delivered in a single composition. In another embodiment, the compound of formula I and the SERM are delivered separately. Desirably, the regimen includes delivering the composition daily for 1 to about 21 days, wherein said regimen is a cycle which is repeated monthly.

Another regimen of the invention can include alternating delivery of the compounds of formula I alone, a SERM alone, and a combination of the compound and the SERM. The regimen can also include the delivery of another reagent prior to, in conjunction with, or subsequent to the compound of formula I and the SERM.

In one embodiment, a single combined daily dosage of the compound of formula I and a SERM can be delivered for the entire 21-day, 28-day, 30-day, or 31-day cycle. Alternatively, a single combined daily dosage of the compound of formula I and a SERM can be delivered for the first 21 days of a 28-day, 30-day, or 31-day cycle. A single combined daily dosage of the compound of formula I and a SERM can also be delivered for the first 24 days of a 28-day, 30-day, or 31-day cycle.

In a further embodiment, a daily dosage of the compound of formula I can be delivered by one route of delivery and a daily dosage of a SERM can be delivered by a second route of delivery for the entire 21-day, 28-day, 30-day, or 31-day cycle. Alternatively, a daily dosage of the compound of formula I can be delivered by one route of delivery and a daily dosage of a SERM can be delivered by a second route of delivery for the first 21 days of a 28-day, 30-day, or 31-day cycle. Further, a daily dosage of the compound of formula I can be delivered by one route of delivery and a daily dosage of a SERM can be delivered by a second route of delivery for the first 24 days of a 28-day, 30-day, or 31-day cycle.

In another embodiment, a daily dosage of the compound of formula I can be delivered, followed by a daily dosage of a SERM for the entire 21-day, 28-day, 30-day, or 31-day cycle. Alternatively, a daily dosage of the compound of formula I can be delivered, followed by a daily dosage of a SERM for the first 21 days of a 28-day, 30-day, or 31-day cycle. Alternatively, a daily dosage of the compound of formula I can be delivered, followed by a daily dosage of a SERM for the first 24 days of a 28-day, 30-day, or 31-day cycle.

In a further embodiment, the compounds of formula I are delivered with a SERM for the first 14 to 24 days of a 28-day cycle, followed by delivery of the SERM alone for a period of 1 to 11 days beginning on any cycle day between day 14 and 24.

In another embodiment, the compounds of formula I can be delivered for the initial 18 to 21 days of a 28-day cycle, followed by delivery of a SERM alone for from 1 to 7 days.

In yet a further embodiment, the compounds of formula I can be delivered alone over a 28 day cycle for the first 21 days, followed by delivery of a SERM alone from day 22 to day 24.

Optionally, progestins can be delivered in combination with the compositions of the present invention. A number of progestins are known in the art and include, without limitation, progesterone, micronized progesterone, levonorgestrel, norgestrel, desogestrel, 3-ketodesogestrel, norethindrone, gestodene, norethindrone acetate, norgestimate, osaterone, cyproterone acetate, trimegestone, dienogest, drospirenone, nomegestrol, and (17-deacetyl)norgestimate, among others. Preferably, the progestins are levonorgestrel, gestodene or trimegestone.

Other reagents can be delivered in combination with the compositions of the present invention. Alternatively, such reagents can be alone administered prior or subsequent to the compositions of the invention. Such reagents can include drying agents including alcohols and benzoyl peroxides; vitamin C and D sources; amino acid reagents; enzyme activators; mineral oil; lanolin; propylene glycol; sodium lauryl sulfate; among others, and combinations thereof. Further, oral reagents include antibiotics; anti-inflammatory agents; herbal extracts including burdock root, yellow dock, horsetail, dandelion root, licorice root, echinacea, kelp, cayenne, sassafras, and elder flowers; xanthan gum; cytokines, androgens, and antiprogestins. Antibiotics can also be applied as in a topical vehicle. Such reagents can also include chemotherapeutic agents, cytokines, androgens, and antiprogestins, among others. Preferably, the chemotherapeutic agents are taxol or cisplatin. In addition, the compositions of the invention can be delivered in conjunction with other cancer treatments, including radiation therapy and/or surgery.

The term "enzyme activator" is meant to describe a reagent which activates fat and glucose metabolism and thereby results in the prevention of future acne occurrences. Preferably, the enzyme activator is a transition metal complex, more preferably is a group 5 or 6 transition metal complex, and most preferably a vanadium or chromium complex.

An isoflavone can alone be delivered or co-delivered with the compositions of the present invention in an amount sufficient to assist in the treatment of carcinomas. A number of isoflavones can be utilized and include, without limitation, genistein, daidzein, biochanin A, formononetin, and naturally occuring glucosides and glucoside conjugates. The amount of isoflavone sufficient to treat the carcinoma is dependent on the particular isoflavone utilized, the amount and activity of the co-delivered active agent, the size of the patient, the route of delivery, and the severity of the carcinoma. The amount of isoflavone sufficient to treat the hormone related condition is preferably at least 1 mg per day, more preferably from about 1 mg to about 1000 mg per day, and most preferably from about 50 mg to about 500 mg per day.

In addition, the compositions of the invention can be delivered in conjunction with other skin treatments, including laser surgery.

The dosage regimens can be adjusted to provide the optimal therapeutic response. For example, several divided doses of each component can be delivered daily or the dose can be proportionally increased or reduced as indicated by the exigencies of the therapeutic situation. In the descriptions herein, reference to a daily dosage unit can also include divided units which are delivered over the course of each day of the cycle contemplated.

V. Pharmaceutical Kits

The present invention provides kits or packages of pharmaceutical formulations designed for use in the regimens described herein. These kits are preferably designed for daily oral delivery over 21-day, 28-day, 30-day, or 31-day cycles, among others, and more preferably for one oral delivery per day. When the compositions are to be delivered continuously, a package or kit can include the composition in each tablet. When the compositions are to be delivered with periodic discontinuation, a package or kit can include placebos on those days when the composition is not delivered.

The kits are also preferably organized to indicate a single oral formulation or combination of oral formulations to be taken on each day of the cycle, preferably including oral tablets to be taken on each of the days specified, and more preferably one oral tablet will contain each of the combined daily dosages indicated.

In one embodiment, a kit can include a single phase of a daily dosage of the compound of formula I over a 21-day, 28-day, 30-day, or 31-day cycle. Alternatively, a kit can include a single phase of a daily dosage of the compound of formula I over the first 21 days of a 28-day, 30-day, or 31-day cycle. A kit can also include a single phase of a daily dosage of the compound of formula I over the first 28 days of a 30-day or 31-day cycle.

Additional components may be co-administered with the compound of formula I and include progestational agents, estrogens, and selective estrogen receptor modulators.

In a further embodiment, a kit can include a single combined phase of a daily dosage of the compound of formula I and a progestational agent over a 21-day, 28-day, 30-day, or 31-day cycle. Alternatively, a kit can include a single combined phase of a daily dosage of the compound of formula I and a progestational agent over the first 21 days of a 28-day, 30-day, or 31-day cycle. A kit can also include a single combined phase of a daily dosage of the compound of formula I and a progestational agent over the first 28 days of a 30-day or 31-day cycle.

In another embodiment, a 28-day kit can include a first phase of from 14 to 28 daily dosage units of the compound of formula I; a second phase of from 1 to 11 daily dosage units of a progestational agent; and, optionally, a third phase of an orally and pharmaceutically acceptable placebo for the remaining days of the cycle.

In yet a further embodiment, a 28-day kit can include a first phase of from 14 to 21 daily dosage units of the compound of formula I; a second phase of from 1 to 11 daily dosage units of a progestational agent; and, optionally, a third phase of an orally and pharmaceutically acceptable placebo for the remaining days of the cycle.

In another embodiment, a 28-day kit can include a first phase of from 18 to 21 daily dosage units of a compound of formula I; a second phase of from 1 to 7 daily dose units of a progestational agent; and, optionally, an orally and pharmaceutically acceptable placebo for each of the remaining 0 to 9 days in the 28-day cycle.

In yet a further embodiment, a 28-day kit can include a first phase of 21 daily dosage units of a compound of formula I; a second phase of 3 daily dosage units for days 22 to 24 of a progestational agent; and, optionally, a third phase of 4 daily units of an orally and pharmaceutically acceptable placebo for each of days 25 to 28.

In another embodiment, a 28-day kit can include a first phase of from 14 to 21 daily dosage units of a progestational agent equal in progestational activity to about 35 to about 150 µg levonorgestrel, a second phase of from 1 to 11 daily dosage units of a compound of formula I, wherein Q is O, at a daily dosage of from about 2 to 50 mg; and optionally, a third phase of an orally and pharmaceutically acceptable placebo for the remaining days of the cycle in which no antiprogestin, progestin or estrogen is administered.

In a further embodiment a 28-day kit can include a first phase of from 14 to 21 daily dosage units of a progestational agent equal in progestational activity to about 35 to about 100 µg levonorgestrel; second phase of from 1 to 11 daily dosage units of a compound of formula I, wherein Q is O, at a daily dosage of from about 2 to 50 mg; and optionally, a third phase of an orally and pharmaceutically acceptable placebo for the remaining days of the cycle in which no antiprogestin, progestin or estrogen is administered.

Preferably, the daily dosage of each pharmaceutically active component of the regimen remains fixed in each particular phase in which it is delivered. It is further preferable that the daily dosage units described are to be delivered in the order described, with the first phase followed in order by the second and third phases. To help facilitate compliance with each regimen, it is also preferred that the kits contain the placebo described for the final days of the cycle.

A number of packages or kits are known in the art for the use in dispensing pharmaceutical agents for oral use. Preferably, the package has indicators for each day of the 28-day cycle, and more preferably is a labeled blister package, dial dispenser package, or bottle.

The compounds of the present invention encompass tautomeric forms of the structures provided herein characterized by the bioactivity of the drawn structures. Further, the compounds of the present invention can be used in the form of salts derived from pharmaceutically or physiologically acceptable acids, bases, alkali metals and alkaline earth metals.

VI. Methods of the Invention

The compounds of the present invention have a variety of uses. Desirably, the compounds of the invention are useful for treating or preventing hormone-related conditions. Specifically, the compounds of the invention are useful in treating or preventing progesterone-related conditions. In one embodiment, the compounds of the invention are useful for binding to the progesterone receptor.

Desirably, the compounds of the invention are useful in contraception. When used for such a purpose, the compounds can be administered to a mammalian subject, and preferably, a female of child-bearing age. Typically, a pharmaceutically acceptable amount of the compound is administered to the mammalian subject.

In another embodiment, the compounds of the invention are useful for treating and preventing other progesterone-related conditions and include hormone replacement therapy.

In a further embodiment, the compounds of the invention are useful for treating uterine fibroids, endometriosis, dysmenorrhea, breast cancer, uterine cancer, ovarian cancer, prostate cancer, and meningioma.

In yet another embodiment, the compounds of the invention are useful for treating skin disorder, including acne and hirsutism, among others.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLES

Example 1

6-[(3-chlorophenyl)amino]-4,4-diethyl-1-methyl-1,4-dihydro-2H-3,1-benzoxazin-2-one A.
4,4-Diethyl-1,4-dihydro-benzo[d][1,3]oxazin-2-one A solution of methyl 2-amino-benzoate (15.1 grams (g), 100 millimoles (mmol)) in dry THF (200 milliliters (mL)) was treated at −78° C. under nitrogen with a solution of ethylmagnesium bromide in ether (3.0 M, 133 mL, 399 mmol). The reaction mixture was slowly warmed to ambient temperature, kept stirring for 2 hours under nitrogen and then poured into a cold 1 N aqueous hydrochloride solution (500 mL). The mixture was neutralized with aqueous 1 N sodium hydroxide solution and ethyl acetate (500 mL) was added. The organic layer was separated and the aqueous layer was extracted with ethyl acetate (3×100 mL). The combined organic layers were washed with brine and dried (MgSO$_4$). After removal of solvent in vacuo, the residue was taken up in anhydrous THF (200 mL) and used in the next step without further purification. To this solution was added 1,1'-carbonyldiimidazole (23.25 g, 150 mmol) under nitrogen. The reaction solution was heated at 50° C. overnight. The solvent was removed in vacuo and the residue was dissolved in ethyl acetate (100 mL). The solution was washed with 1N aqueous hydrochloride solution (2×40 mL), brine (20 mL), and dried with MgSO$_4$. After removal of solvent in vacuo, the residue was triturated with diethyl ether to give the title compounds as white solid (14.8 g, 72%, mp 159-160° C.). $^1$H NMR (CDCl$_3$): δ 8.40 (s, 1H), 7.22 (td, J=7.3, 1.6 Hz, 1H), 7.05 (td, J=7.8, 1.0 Hz, 1H), 7.02 (dd, J=7.7, 1.3 Hz, 1H), 6.80 (d, J=7.7 Hz, 1H), 1.98 (m, 4H), 0.89 (t, J=7.3 Hz, 6H); MS (EI) m/z 205; Anal. calcd for C$_{12}$H$_{15}$NO$_2$: C, 70.22; H, 7.37; N, 6.82. Found: C, 69.88H, 6.99; N, 6.31.

B. 4,4-diethyl-6-nitro-1,4-dihydro-2H-3,1-benzoxazin-2-one

To a stirred suspension of 4,4-diethyl-1,4-dihydro-benzo[d][1,3]oxazin-2-one (6.00 g, 29.20 mmol) in a mixture of glacial acetic acid (25 mL) and concentrated sulfuric acid (25 mL) was slowly added concentrated nitric acid (5 mL). After stirring 10 minutes, the reaction mixture was quenched with a chilled brine solution (100 mL) and ice. A solid precipitated, which was collected on a filter and washed with water. After drying in vacuo, 4,4-diethyl-6-nitro-1,4-dihydro-2H-3,1-benzoxazin-2-one was obtained as a white solid (5.02 g, 69%). $^1$H NMR (DMSO-d$_6$): δ 10.85 (s, 1H), 8.20 (dd, J=8.8, 2.5 Hz, 1H), 8.06 (d, J=2.4 Hz, 1H), 7.06 (d, J=8.8 Hz, 1H), 2.14 (m, 4H), 0.79 (t, J=7.3 Hz, 6H); MS (ESI) m/z 251 ([M+H]+); MS (ESI) m/z 249 ([M–H]–); Anal. calcd for C$_{12}$H$_{14}$N$_2$O$_4$: C, 57.59; H, 5.64; N, 1.19. Found: C, 57.44; H, 5.57; N, 11.16.

C. 4,4-diethyl-1-methyl-6-nitro-1,4-dihydro-2H-3,1-benzoxazin-2-one

To a stirred solution of 4,4-diethyl-6-nitro-1,4-dihydro-2H-3,1-benzoxazin-2-one (5.00 g, 19.98 mmol) in DMF (30 mL) at 0° C. was added sodium hydride (1.20 g-60%, 29.97 mmol). After 20 minutes, methyl iodide (3.8 mL, 61.00 mmol) was added and the reaction was warmed to room temperature. After stirring for one hour, the reaction was quenched with ammonium chloride (sat.) and extracted with ethyl acetate (3×50 mL). The combined organic layers were washed with brine repeatedly and dried over magnesium sulfate. Solvent was removed and the residue was triturated with ether to give 4,4-diethyl-1-methyl-6-nitro-1,4-dihydro-2H-3,1-benzoxazin-2-one as a yellowish-white solid (3.74 g, 71%). $^1$H NMR (DMSO-d$_6$): δ 8.27 (dd, J=9.0, 2.6 Hz, 1H), 8.05 (d, J=2.6 Hz, 1H), 7.34 (d, J=9.0 Hz, 1H), 3.37 (s, 3H), 2.15 (m, 4H), 0.80 (t, J=7.3 Hz, 6H); MS (ESI) m/z 265 ([M+H]+); Anal. calcd for C$_{13}$H$_{16}$N$_2$O$_4$: C, 59.08; H, 6.10; N 10.60. Found: C, 59.62; H, 6.20; N, 10.48.

D. 6-amino-4,4-diethyl-1-methyl-1,4-dihydro-2H-3,1-benzoxazin-2-one

To a stirred suspension of 4,4-diethyl-1-methyl-6-nitro-1,4-dihydro-2H-3,1-benzoxazin-2-one (3.74 g, 14.15 mmol) and 5% palladium on carbon (0.20 g) in methanol (35 mL) at 0° C. was added sodium borohydride (10.70 g, 28.30 mmol) portionwise. After stirring 1 hr at 0° C., the reaction was quenched with ice and ammonium chloride solution (sat.) and extracted with ethyl acetate (3×50 mL). The combined organic layers were washed with brine and dried over magnesium sulfate. Solvent was removed and trituration of the residue with ether gave 6-amino-4,4-diethyl-1-methyl-1,4-dihydro-2H-3,1-benzoxazin-2-one as a yellow solid (2.67 g, 81%). $^1$H NMR (DMSO-d$_6$): δ 6.78 (d, J=8.6 Hz, 1H), 6.56 (m, 1H), 6.40 (d, J=2.4 Hz, 1H), 4.93 (s, 2H), 3.18 (s, 3H), 1.99 (m, 4H), 0.80 (t, J=7.3 Hz, 6H); MS (ESI) m/z 235 ([M+H]+); Anal. calcd for C$_{13}$H$_{18}$N$_2$O$_2$: C, 66.64; H7.74; N 11.96. Found: C, 64.97; H, 7.67; N, 11.62.

E. 6-[(3-chlorophenyl)amino]-4,4-diethyl-1-methyl-1,4-dihydro-2H-3,1-benzoxazin-2-one To a solution of 6-amino-4,4-diethyl-1-methyl-1,4-dihydro-2H-3,1-benzoxazin-2-one (0.13 g, 0.53 mmol) and 3-chlorophenylboronic acid (0.42 g, 2.66 mmol) in methylene chloride (5 mL) was added triethylamine (0.4 mL, 2.87 mmol), and copper (II) acetate (0.19 g, 1.06 mmol) and stirred at room temperature for 2 days. The reaction was partitioned between ammonium chloride solution (sat.) and methylene chloride. The organic layer was washed with sodium bicarbonate solution (sat.), dried over magnesium sulfate, and concentrated. Flash silica gel column separation with 25% ethyl acetate/hexane followed by trituration with an ether/methylene chloride/hexane mixture gave the title compound as a white solid (0.08 g, 43%). $^1$H NMR (DMSO-d$_6$): δ 8.32 (s, 1H), 7.21 (t, J=8.0 Hz, 1H), 7.13 (dd, J=8.6, 2.3 Hz, 1H), 7.05 (d, J=8.7 Hz, 1H), 6.91 (m, 2H), 6.87 (dd, J=7.6, 1.4 Hz, 1H), 6.77 (d, J=7.8 Hz, 1H), 3.27 (s, 3H), 1.97 (m, 4H), 0.82 (t, J=7.3 Hz, 6H). MS (ESI) m/z 345/347 ([M+H]+); MS (ESI) m/z 343/345 ([M–H]–); Anal. calcd for C$_{19}$H$_{21}$ClN$_2$O$_2$: C, 66.18; H, 6.14; N, 8.12. Found: C, 65.70; H, 6.01; N, 7.90.

Example 2

4-(4-chlorophenyl)-6-[(3-chlorophenyl)amino]-1,4-dimethyl-1,4-dihydro-2H-3,1-benzoxazin-2-one A. 4,4-Dimethyl-6-nitro-1,4-dihydro-2H-3,1-benzoxazin-2-one Prepared from 4,4-dimethyl-1,4-dihydro-2H-3,1-benzoxazin-2-one, which was synthesized according to the procedure depicted in example 1, using the nitration procedure described in example 1. $^1$H NMR (DMSO-d$_6$): δ 11.02 (brs, 1H), 8.19 (d, J=2.4 Hz, 1H), 8.16 (m, 1H), 7.05 (dd, J=8.7, 0.5 Hz, 1H), 1.7 (s, 6H); MS (ESI) m/z 223 ([M+H]+); MS (ESI) m/z 221 ([M–H]–); Anal. calcd for C$_{10}$H$_{10}$N$_2$O$_4$: C, 54.06; H, 4.54; N, 12.61. Found: C, 52.78; H, 4.20; N, 12.23.

B. 1,4,4-Trimethyl-6-nitro-1,4-dihydro-2H-3,1-benzoxazin-2-one

Prepared according to the procedure described in example 1. An off-white solid, $^1$H NMR (DMSO-d$_6$): δ 8.28 (dd, J=9.0, 2.5 Hz, 1H), 8.19 (d, J=2.5 Hz, 1H), 7.34 (d, J=9.1 Hz, 1H), 3.38 (s, 3H), 1.71 (s, 6H); MS (ESI) m/z 237 ([M+H]+).

C. 6-Amino-1,4,4-trimethyl-1,4-dihydro-2H-3,1-benzoxazin-2-one

Prepared according to the reduction procedure described in example 1. $^1$H NMR (DMSO-d$_6$): δ 6.79 (d, J=8.4 Hz, 1H), 6.56 (dd, J=8.5, 2.5 Hz, 1H), 6.52 (d, J=2.4 Hz, 1H), 4.97 (s, 2H), 3.22 (s, 3H), 1.53 (s, 6H); MS (ESI) m/z 207 ([M+H]+).

D. 4-(4-chlorophenyl)-6-[(3-chlorophenyl)amino]-1,4-dimethyl-1,4-dihydro-2H-3,1-benzoxazin-2-one To a stirred solution of 6-amino-4-(4-chlorophenyl)-1,4-dimethyl-1,4-dihydro-2H-3,1-benzoxazin-2-one (0.09 g, 0.30 mmol) and 1-chloro-3-iodobenzene (0.2 mL, 1.62 mmol) in THF (2 mL) was added $Pd_2(dba)_3$ (0.03 g, 0.03 mmol), BINAP (0.03 g, 0.05 mmol), sodium t-butoxide (0.07 g, 0.45 mmol), and 18-crown-6 (0.12 g, 0.45 mmol). The reaction mixture was stirred at room temperature for 2 days, quenched with ammonium chloride solution (sat.) and extracted several times with ethyl acetate. The combined organic layers were dried over magnesium sulfate and concentrated. Flash silica gel column separation with 20% ethyl acetate/hexane followed by trituration with hexane gave the title compound as brown solid (0.02 g, 18%). $^1H$ NMR (DMSO-$d_6$): δ 8.43 (s, 1H), 7.46 (dd, J=6.7, 2.0 Hz, 2H), 7.31 (dd, J=6.8, 2.2 Hz, 2H), 7.28 (m, 2H), 7.10 (d, J=10.5 Hz, 1H), 7.09 (s, 1H), 6.94 (m, 2H), 6.80 (m, 1H), 3.17 (s, 3H), 1.92 (s, 3H); MS (ESI) m/z [M+H]+ (413/415); MS (ESI) m/z [M−H]−(411/413); Anal. calcd for $C_{22}H_{18}Cl_2N_2O_2$: C, 63.93; H, 4.39 N, 6.78. Found: C, 62.88; H, 4.72; N, 5.67.

Example 3

6-[(3,4-dichlorophenyl)amino]-4,4-diethyl-1-methyl-1,4-dihydro-2H-3,1-benzoxazin-2-one Prepared from 6-amino-4,4-diethyl-1-methyl-1,4-dihydro-2H-3,1-benzoxazin-2-one and 1,2-dichloro-4-iodobenzene according to the coupling protocol described in example 2. $^1H$ NMR (DMSO-$d_6$): δ 8.43 (s, 1H), 7.40 (d, J=8.7 Hz, 1H), 7.13 (dd, J=8.6, 2.3 Hz, 1H), 7.06 (m, 2H), 6.93 (d, J=2.4 Hz, 1H), 6.89 (dd, J=8.8, 2.7 Hz, 1H), 3.27 (s, 3H), 1.98 (m, 4H), 0.82 (t, J=7.3 Hz, 6H); MS (ESI) m/z 379/381/383 ([M+H]+); MS (ESI) m/z 377/379/381 ([M−H]−).

Example 4

6-[(3,5-dichlorophenyl)amino]-4,4-diethyl-1-methyl-1,4-dihydro-2H-3,1-benzoxazin-2-one Prepared from 6-amino-4,4-diethyl-1-methyl-1,4-dihydro-2H-3,1-benzoxazin-2-one and 3,5-dichlorophenylboronic acid according to the coupling protocol of example 1. $^1H$ NMR (DMSO-$d_6$): δ 8.55 (s, 1H), 7.16 (dd, J=8.7, 2.3 Hz, 1H), 7.09 (d, J=8.7 Hz, 1H), 6.97 (d, J=2.4 Hz, 1H), 6.84 (m, 1H), 6.82 (m, 2H), 3.28 (s, 3H), 2.00 (m, 2H), 1.92 (m, 2H), 0.82 (t, J=7.4 Hz, 6H); MS (ESI) m/z 379/381/383 ([M+H]+); MS (ESI) m/z 377/379/381 ([M−H]−); Anal. calcd for $C_{19}H_{20}Cl_2N_2O_2$: C, 60.17; H, 5.32; N, 7.39. Found: C, 60.10; H, 5.26; N, 7.26.

Example 5

4,4-diethyl-6-[(3-fluoro-5-nitrophenyl)amino]-1-methyl-1,4-dihydro-2H-3,1-benzoxazin-2-one Prepared from 6-amino-4,4-diethyl-1-methyl-1,4-dihydro-2H-3,1-benzoxazin-2-one and 1-fluoro-3-iodo-5-nitrobenzene according to the coupling protocol of example 2. $^1H$ NMR (DMSO-$d_6$): δ 8.92 (s, 1H), 7.53 (t, J=1.8 Hz, 1H), 7.36 (dt, J=8.6, 2.2 Hz, 1H), 7.21 (dd, J=8.7, 2.4 Hz, 1H), 7.12 (d, J=8.7 Hz, 1H), 7.06 (d, J=2.4 Hz, 1H), 7.03 (dt, J=11.1, 2.2 Hz, 1H), 3.29 (s, 3H), 2.01 (m, 4H), 0.82 (t, J=7.3 Hz, 6H); MS (ESI) m/z 374 ([M+H]+); MS (ESI) m/z 372 ([M−H]−); Anal. calcd for $C_{19}H_{20}FN_3O_4$: C, 61.12; H, 5.40; N, 11.25. Found: C, 60.33; H, 5.17; N, 10.51.

Example 6

3-[(4,4-diethyl-1-methyl-2-oxo-1,4-dihydro-2H-3,1-benzoxazin-6-yl)amino]-5-fluorobenzonitrile Prepared from 6-amino-4,4-diethyl-1-methyl-1,4-dihydro-2H-3,1-benzoxazin-2-one and 5-fluoro-3-cyanophenylboronic acid according to the coupling protocol of example 1. $^1H$ NMR (DMSO-$d_6$): δ 8.74 (s, 1H), 7.20 (dd, J=8.6, 2.3 Hz, 1H), 7.09 (m, 2H), 7.02 (m, 1H), 6.99 (d, J=2.4 Hz, 1H), 6.94 (dt, J=11.7, 2.2 Hz, 1H), 3.28 (s, 3H), 2.01 (m, 4H), 0.82 (t, J=8.3 Hz, 6H); MS (ESI) m/z 354 ([M+H]+); MS (ESI) m/z 352 ([M−H]−). Anal. calcd for $C_{20}H_{20}FN_3O_2$: C, 67.97; H, 5.70; N, 11.89. Found: C, 64.95; H, 5.42; N, 11.05.

Example 7

6-[(2,3-dichlorophenyl)amino]-4,4-diethyl-1-methyl-1,4-dihydro-2H-3,1-benzoxazin-2-one Prepared from 6-amino-4,4-diethyl-1-methyl-1,4-dihydro-2H-3,1-benzoxazin-2-one and 1,2-dichloro-3-iodobenzene according to the coupling procedure described in example 2. $^1H$ NMR (DMSO-$d_6$): δ 7.83 (s, 1H), 7.17 (m, 2H), 7.06 (d, J=8.7 Hz, 1H), 7.03 (m, 2H), 6.94 (dd, J=8.3, 1.4 Hz, 1H), 3.28 (s, 3H), 1.97 (m, 4H), 0.81 (t, J=7.3 Hz, 6H); MS (ESI) m/z [M+H]+ (379/381/383); Anal. calcd for $C_{19}H_{20}Cl_2N_2O_2$: C, 60.17; H, 5.32; N, 7.39. Found: C, 59.80; H, 4.96; N, 7.13.

Example 8

6-[(2,5-dichlorophenyl)amino]-4,4-diethyl-1-methyl-1,4-dihydro-2H-3,1-benzoxazin-2-one Prepared from 6-amino-4,4-diethyl-1-methyl-1,4-dihydro-2H-3,1-benzoxazin-2-one and 1,4-dichloro-2-iodobenzene according to the coupling procedure described in example 2. $^1H$ NMR (DMSO-$d_6$): δ 7.85 (s, 1H), 7.41 (d, J=8.5 Hz, 1H), 7.20 (dd, J=8.7, 2.4 Hz, 1H), 7.09 (m, 2H), 6.89 (d, J=2.4 Hz, 1H), 6.83 (dd, J=8.5, 2.4 Hz, 1H), 3.29 (s, 3H), 1.97 (m, 4H), 0.82 (t, J=7.3 Hz, 6H); MS (ESI) m/z [M+H]+ (379/381/383); Anal. calcd for $C_{19}H_{20}Cl_2N_2O_2$: C, 60.17; H, 5.32; N, 7.39. Found: C, 59.11; H, 5.36; N, 6.84.

Example 9

6-[(3,4-difluorophenyl)amino]-4,4-diethyl-1-methyl-1,4-dihydro-2H-3,1-benzoxazin-2-one Prepared from 6-amino-4,4-diethyl-1-methyl-1,4-dihydro-2H-3,1-benzoxazin-2-one and 3,4-difluorophenylboronic acid according to the coupling procedure described in example 1. $^1H$ NMR (DMSO-$d_6$): δ 8.24 (s, 1H), 7.28 (q, J=9.2 Hz, 1H), 7.11 (dd, J=8.7, 2.4 Hz, 1H), 7.02 (d, J=8.7 Hz, 1H), 6.90 (m, 2H), 6.74 (m, 1H), 3.26 (s, 3H), 1.97 (m, 4H), 0.81 (t, J=7.3 Hz, 6H). MS (ESI) m/z [M+H]+ (347); MS (ESI) m/z [M−H]−(345); Anal. calcd for $C_{19}H_{20}F_2N_2O_2$: C, 65.88; H, 5.82 N, 8.09. Found: C, 65.30; H, 5.71; N, 7.79.

Example 10

6-[(3,5-difluorophenyl)amino]-4,4-diethyl-1-methyl-1,4-dihydro-2H-3,1-benzoxazin-2-one Prepared from 6-amino-4,4-diethyl-1-methyl-1,4-dihydro-2H-3,1-benzoxazin-2-one and 3,5-difluorophenylboronic acid according to the coupling procedure described in example 1. $^1$H NMR (DMSO-$d_6$): δ 8.58 (s, 1H), 7.17 (dd, J=8.7, 2.5 Hz, 1H), 7.07 (d, J=8.7 Hz, 1H), 6.95 (d, J=2.3 Hz, 1H), 6.51 (s, 1H), 6.49 (m, 2H), 3.28 (s, 3H), 1.99 (m, 4H), 0.81 (t, J=7.4 Hz, 6H). MS (ESI) m/z 347 ([M+H]+); MS (ESI) m/z 345 ([M−H]−); Anal. calcd for $C_{19}H_{20}F_2N_2O_2$: C, 65.88; H, 5.82; N, 8.09. Found: C, 64.99; H, 5.63; N, 7.89.

Example 11

6-[(3-chloro-4-fluorophenyl)amino]-4,4-diethyl-1-methyl-1,4-dihydro-2H-3,1-benzoxazin-2-one Prepared from 6-amino-4,4-diethyl-1-methyl-1,4-dihydro-2H-3,1-benzoxazin-2-one and 3-chloro-4-fluorophenylboronic acid according to the coupling procedure described in example 1. $^1$H NMR (DMSO-$d_6$): δ 8.22 (s, 1H), 7.26 (t, J=9.1 Hz, 1H), 7.09 (dd, J=8.7, 2.3 Hz, 1H), 7.03 (m, 2H), 6.91 (m, 1H), 6.88 (d, J=2.3 Hz, 1H), 3.26 (s, 3H), 1.97 (m, 4H), 0.82 (t, J=7.2 Hz, 6H); MS (ESI) m/z 363/365 ([M+H]+); MS (ESI) m/z 361/363 ([M−H]−); Anal. calcd for $C_{19}H_{20}ClFN_2O_2$: C, 62.90H, 5.56; N, 7.72. Found: C, 62.65; H, 5.53; N, 7.58.

Example 12

6-[(3-acetylphenyl)amino]-4,4-diethyl-1-methyl-1,4-dihydro-2H-3,1-benzoxazin-2-one Prepared from 6-amino-4,4-diethyl-1-methyl-1,4-dihydro-2H-3,1-benzoxazin-2-one and 3-acetylphenylboronic acid according to the coupling procedure described in example 1. $^1$H NMR (DMSO-$d_6$): δ 8.34 (s, 1H), 7.53 (d, J=1.8 Hz, 1H), 7.39 (m, 2H), 7.19 (dt, J=7.4, 1.9 Hz, 1H), 7.12 (dd, J=8.8, 2.5 Hz, 1H), 7.04 (d, J=8.8 Hz, 1H), 6.94 (d, J=2.5 Hz, 1H), 3.27 (s, 3H), 2.52 (s, 3H), 1.99 (m, 4H), 0.83 (t, J=7.4 Hz, 6H); MS (ESI) m/z 353 ([M+H]+); MS (ESI) m/z 351 ([M−H]−); Anal. calcd for $C_{21}H_{24}N_2O_3$: C, 71.57; H, 6.86; N, 7.95. Found: C, 69.83; H, 6.78; N, 7.86.

Example 13

5-[(4,4-diethyl-1-methyl-2-oxo-1,4-dihydro-2H-3,1-benzoxazin-6-yl)amino]-2-fluorobenzonitrile Prepared from 6-amino-4,4-diethyl-1-methyl-1,4-dihydro-2H-3,1-benzoxazin-2-one and 3-cyano-4-fluorophenylboronic acid according to the coupling procedure described in example 1. $^1$H NMR (DMSO-$d_6$): δ 8.40 (s, 1H), 7.38 (t, J=8.9 Hz, 1H), 7.27 (m, 2H), 7.14 (dd, J=8.6, 2.3 Hz, 1H), 7.04 (d, J=8.8 Hz, 1H), 6.91 (d, J=2.5 Hz, 1H), 3.27 (s, 3H), 1.98 (m, 4H), 0.81 (t, J=7.4 Hz, 6H); MS (ESI) m/z 354 ([M+H]+); MS (ESI) m/z 352 ([M−H]−); Anal. calcd for $C_{20}H_{20}FN_3O_2$: C, 67.97H, 5.70; N, 11.89. Found: C, 65.58; H, 5.65; N, 11.36.

Example 14

6-[(3-acetyl-4-fluorophenyl)amino]-4,4-diethyl-1-methyl-1,4-dihydro-2H-3,1-benzoxazin-2-one Prepared from 6-amino-4,4-diethyl-1-methyl-1,4-dihydro-2H-3,1-benzoxazin-2-one and 3-acetyl-4-fluorophenylboronic acid according to the coupling procedure described in example 1. MS (ESI) m/z 371 ([M+H]+); MS (ESI) m/z 369 ([M−H]−); High Resolution Mass Spectrometry (HRMS): calcd for $C_{21}H_{23}FN_2O_3$, 370.1693; found (ESI+), 371.17619; Anal. calcd for $C_{21}H_{23}FN_2O_3$: C, 68.09; H, 6.26; N, 7.56. Found: C, 67.36; H, 6.45; N, 7.65.

Example 15

6-[(4-bromophenyl)amino]-4,4-diethyl-1-methyl-1,4-dihydro-2H-3,1-benzoxazin-2-one Prepared from 6-amino-4,4-diethyl-1-methyl-1,4-dihydro-2H-3,1-benzoxazin-2-one and 1-bromo-4-iodobenzene according to the procedure described in example 2. $^1$H NMR (DMSO-$d_6$): δ 8.25 (s, 1H), 7.35 (d, J=8.8 Hz, 2H), 7.11 (dd, J=8.7, 2.3 Hz, 1H), 7.02 (d, J=8.8 Hz, 1H), 6.92 (d, J=8.9 Hz, 2H), 6.87 (d, J=2.3 Hz, 1H), 3.26 (s, 3H), 1.95 (m, 4H), 0.82 (t, J=7.3 Hz, 6H); MS (ESI) m/z 389/391 ([M+H]+); MS (ESI) m/z 387/389 ([M−H]−); Anal. calcd for $C_{19}H_{21}BrN_2O_2$: C, 58.62; H, 5.44 N, 7.20. Found: C, 58.59; H, 5.29; N, 7.03.

Example 16

4-[(4,4-diethyl-1-methyl-2-oxo-1,4-dihydro-2H-3,1-benzoxazin-6-yl)amino]-2-fluorobenzonitrile Prepared from 6-amino-4,4-diethyl-1-methyl-1,4-dihydro-2H-3,1-benzoxazin-2-one and 4-bromo-2-fluorobenzonitrile according to the coupling procedure described in example 2. $^1$H NMR (DMSO-$d_6$): δ 9.15 (s, 1H), 7.62 (t, J=7.9 Hz, 1H), 7.24 (dd, J=8.6, 2.3 Hz, 1H), 7.11 (d, J=8.7 Hz, 1H), 7.03 (d, J=2.4 Hz, 1H), 6.76 (m, 2H), 3.29 (s, 3H), 1.99 (m, 4H), 0.81 (t, J=7.3 Hz, 6H); MS (ESI) m/z 354 ([M+H]+); MS (ESI) m/z 352 ([M−H]−); Anal. calcd for $C_{20}H_{20}FN_3O_2$: C, 67.97H, 5.70; N, 11.89. Found: C, 67.09; H, 5.64; N, 11.53.

Example 17

6-[(2,3-dichlorophenyl)amino]-4,4-dimethyl-1,4-dihydro-2H-3,1-benzoxazin-2-one Prepared from 6-amino-1,4,4-trimethyl-1,4-dihydro-2H-3,1-benzoxazin-2-one and 2,3-difluorophenyl boronic acid according to the coupling procedure described in example 1. MS (ESI) m/z 337/339/340 ([M+H]+); MS (ESI) m/z 335/337/339 ([M−H]−); Anal. calcd for $C_{16}H_{14}Cl_2N_2O_2$: C, 56.99; H, 4.18; N, 8.31. Found: C, 57.46H, 4.44; N, 7.88.

Example 18

6-[(2,3-dichlorophenyl)amino]-1,4,4-trimethyl-1,4-dihydro-2H-3,1-benzoxazin-2-one Prepared from 6-amino-1,4,4-trimethyl-1,4-dihydro-2H-3,1-benzoxazin-2-one and 2,3-dichlorophenyl boronic acid according to the coupling procedure described in example 1. MS (ESI) m/z 351/353/355 ([M+H]+); MS (ESI) m/z 349/

351/353 ([M–H]–); Anal. calcd for $C_{17}H_{16}Cl_2N_2O_2$: C, 58.13; H, 4.59; N, 7.98. Found: C, 58.59H, 4.61; N, 7.36.

Example 19

6-[(4-bromophenyl)amino]-1,4,4-trimethyl-1,4-dihydro-2H-3,1-benzoxazin-2-one Prepared from 6-amino-1,4,4-trimethyl-1,4-dihydro-2H-3,1-benzoxazin-2-one and 4-bromophenyl boronic acid according to the coupling procedure described in example 1. MS (ESI) m/z 361/363 ([M+H]+); MS (ESI) m/z 359/361 ([M–H]–); Anal. calcd for $C_{17}H_{17}BrN_2O_2$: C, 56.52; H, 4.74; N, 7.75. Found: C, 56.98; H, 4.34; N, 7.30.

Example 20

1,4,4-trimethyl-6-[(4-nitrophenyl)amino]-1,4-dihydro-2H-3,1-benzoxazin-2-one Prepared from 6-amino-1,4,4-trimethyl-1,4-dihydro-2H-3,1-benzoxazin-2-one and 4-nitrophenyl boronic acid according to the coupling procedure described in example 1. MS (ESI) m/z 328 ([M+H]+); MS (ESI) m/z 326 ([M–H]–); Anal. calcd for $C_{17}H_{17}N_3O_4$: C, 62.38; H, 5.23; N, 12.84. Found: C, 62.03; H, 5.15; N, 11.41.

Example 21

6-[(3-chloro-4-fluorophenyl)amino]-4,4-diethyl-5-fluoro-1-methyl-1,4-dihydro-2H-3,1-benzoxazin-2-one

A. 4,4-diethyl-5-fluoro-1,4-dihydro-2H-3,1-benzoxazin-2-one

To a stirred solution of 2-amino-6-fluorobenzoic acid (15.34 g, 98.90 mmol) in THF (330 mL) at 0° C. was slowly added ethyl magnesium bromide (650 mL, 650.0 mmol) and allowed to warm to room temperature. After 3 days, the reaction was quenched with chilled ammonium chloride solution (sat.) and extracted several times with ethyl acetate. The combined organic layers were dried over magnesium sulfate and concentrated. The crude material was taken up in THF (300 mL) and CDI (14.97 g, 92.30 mmol) was added. The reaction was stirred overnight at room temperature and partitioned between ammonium chloride solution (sat.) and ethyl acetate. The organic layer was washed with 1N HCl and dried over magnesium sulfate. Trituration with ether gave 4,4-diethyl-5-fluoro-1,4-dihydro-2H-3,1-benzoxazin-2-one as an off-white solid (9.57 g, 43%). $^1$H NMR (DMSO-$d_6$): δ 10.33 (s, 1H), 7.31 (m, 1H), 6.86 (m, 1H), 6.73 (d, J=8.0 Hz, 1H), 2.08 (m, 2H), 1.90 (m, 2H), 0.80 (t, J=7.2 Hz, 6H); MS (ESI) m/z 224 ([M+H]+); MS (ESI) m/z 222 ([M–H]–); Anal. calcd for $C_{12}H_{14}FNO_2$: C, 64.56; H, 6.32; N, 6.27. Found: C, 64.64; H, 6.27 N, 6.16.

B. 4,4-diethyl-5-fluoro-1-methyl-6-nitro-1,4-dihydro-2H-3,1-benzoxazin-2-one To a stirred solution of 4,4-diethyl-5-fluoro-1,4-dihydro-2H-3,1-benzoxazin-2-one (9.55 g, 42.80 mmol), prepared according to the procedure described in example 1, in THF (140 mL) at 0° C. was added sodium hydride (3.40 g, 60%, 85.00 mmol) portionwise. After 10 minutes, methyl iodide (8.0 mL, 128 mmol) was added and the reaction was allowed to warm to room temperature. After 2.5 hours the reaction was quenched with ammonium chloride solution (sat) and extracted with ethyl acetate. The organic layer was dried over magnesium sulfate and concentrated. The crude material was added to a mixture of glacial acetic acid (18 mL) and concentrated sulfuric acid (18 mL). Concentrated nitric acid (5 mL) was added slowly. After 10 minutes the reaction was poured into brine (150 mL) and ice. The mixture was extracted several times with ethyl acetate, and the combined organic layers were dried over magnesium sulfate and concentrated. Flash silica gel column separation with 15-30% ethyl acetate/hexane followed by trituration with ether gave 4,4-diethyl-5-fluoro-1-methyl-6-nitro-1,4-dihydro-2H-3,1-benzoxazin-2-one as an off-white solid (3.0 g, 25%). $^1$H NMR (DMSO-$d_6$): δ 8.24 (t, J=8.5 Hz, 1H), 7.16 (dd, J=9.3, 1.0 Hz, 1H), 3.36 (s, 3H), 2.16 (m, 2H), 1.96 (m, 2H), 0.85 (t, J=7.4 Hz, 6H); MS (ESI) m/z 283 ([M+H]+); Anal. calcd for $C_{13}H_{15}FN_2O_4$: C, 55.32; H 5.36; N 9.92. Found: C, 55.29; H, 5.30; N, 9.96.

C. 6-amino-4,4-diethyl-5-fluoro-1-methyl-1,4-dihydro-2H-3,1-benzoxazin-2-one Prepared from 4,4-diethyl-5-fluoro-1-methyl-6-nitro-1,4-dihydro-2H-3,1-benzoxazin-2-one according to reduction procedure described in example 1. $^1$H NMR (DMSO-$d_6$): δ 6.80 (t, J=8.8 Hz, 1H), 6.68 (dd, J=8.7, 1.0 Hz, 1H), 5.00 (s, 2H), 3.20 (s, 3H), 2.08 (m, 2H), 1.86 (m, 2H), 0.83 (t, J=7.3 Hz, 6H); MS (ESI) m/z 253 ([M+H]+); Anal. calcd for $C_{13}H_{17}FN_2O_2$: C, 61.89; H, 6.79; N, 11.10. Found: C, 61.82; H, 6.65; N, 10.96.

D. 6-[(3-chloro-4-fluorophenyl)amino]-4,4-diethyl-5-fluoro-1-methyl-1,4-dihydro-2H-3,1-benzoxazin-2-one Prepared from 6-amino-4,4-diethyl-5-fluoro-1-methyl-1,4-dihydro-2H-3,1-benzoxazin-2-one and 3-chloro-4-fluorophenylboronic acid according to the coupling procedure described in example 1. $^1$H NMR (DMSO-$d_6$): δ 8.03 (s, 1H), 7.32 (t, J=8.8 Hz, 1H), 7.26 (t, J=9.1 Hz, 1H), 6.92 (m, 2H), 6.83 (m, 1H), 3.29 (s, 3H), 2.12 (m, 2H), 1.92 (m, 2H), 0.84 (t, J=7.2 Hz, 6H); MS (ESI) m/z 381/383 ([M+H]+); MS (ESI) m/z 379/381 ([M–H]–); Anal. calcd for $C_{19}H_{19}ClF_2N_2O_2$: C, 59.93; H, 5.03; N, 7.36. Found: C, 59.68; H, 4.92; N, 7.14.

Example 22

6-[(3-chlorophenyl)amino]-4-ethyl-4-thien-2-yl-1,4-dihydro-2H-3,1-benzoxazin-2-one Prepared from 1-[2-amino-5-(3-chlorophenylamino)-phenyl]-1-thiophen-2-yl-propan-1-ol according to the procedures described in example 1. $^1$H NMR (DMSO-$d_6$): δ 10.24 (s, 1H), 8.30 (s, 1H), 7.53 (dd, J=5.1, 1.3 Hz, 1H), 7.19 (t, J=8.1 Hz, 1H), 7.11 (dd, J=8.6, 2.4 Hz, 1H), 7.01 (m, 2H), 6.92 (dd, J=3.6, 1.3 Hz, 1H), 6.89 (m, 2H), 6.83 (m, 1H), 6.75 (m, 1H), 2.43 (m, 2H), 0.96 (t, J=7.2 Hz, 3H); MS (ESI) m/z [M+H]+ (385/387); Anal. calcd for $C_{20}H_{17}ClN_2O_2S$: C, 62.41; H, 4.45; N 7.28. Found: C, 62.56; H, 4.60; N, 7.01.

Example 23

6-[(3-chlorophenyl)amino]-4-ethyl-1-methyl-4-thien-2-yl-1,4-dihydro-2H-3,1-benzoxazin-2-one Prepared from 6-[(3-chlorophenyl)amino]-4-ethyl-4-thien-2-yl-1,4-dihydro-2H-3,1-benzoxazin-2-one according to the alkylation procedure described in example 1. $^1$H NMR (DMSO-$d_6$): δ 8.40 (s, 1H), 7.53 (dd, J=5.0, 1.2 Hz, 1H), 7.22 (m, 2H), 7.11 (d, J=8.8 Hz, 1H), 7.05 (d, J=2.4 Hz, 1H), 7.01 (m, 1H), 6.93 (m, 2H), 6.90 (m, 1H), 6.79 (m, 1H), 3.24 (s, 3H), 2.46 (m, 2H), 0.97 (t, J=7.2 Hz, 3H); MS (ESI) m/z 399/401 ([M+H]+); Anal. calcd for $C_{21}H_{19}ClN_2O_2S$: C, 63.23; H, 4.80; N, 7.02. Found: C, 62.94; H, 4.87; N, 6.83.

Example 24

6-[(3-chloro-4-fluorophenyl)amino]-4-ethyl-4-thien-2-yl-1,4-dihydro-2H-3,1-benzoxazin-2-one A. 2-amino-5-[(3-chloro-4-fluorophenyl)amino]benzonitrile 5-Fluoro-2-nitrobenzonitrile (25.90 g, 156.0 mmol) and 3-chloro-4-fluorophenylamine (45.40 g, 312.0 mmol) were combined in ethanol (500 mL) and heated to reflux. After 7 days, the reaction was cooled to room temperature and filtered. The solid was washed with ethanol. The solid was added to a mixture of water (100 mL) and glacial acetic acid (100 mL) and heated to 90° C. Iron powder (17.80 g, 320 mmol) was added slowly over 10 minutes. After an additional 30 minutes, the reaction was allowed to cool to room temperature and filtered through magnesol. The filtrate was taken up in ethyl acetate and washed with sodium bicarbonate solution (sat) and the organic layer was filtered through magnesol, dried over magnesium sulfate and concentrated. Trituration with ether/hexane gave 2-amino-5-[(3-chloro-4-fluorophenyl)amino]benzonitrile as a brown solid (5.9 g, 14%). $^1$H NMR (DMSO-$d_6$): δ 7.85 (s, 1H), 7.20 (t, J=9.1 Hz, 1H), 7.15 (dd, J=8.8, 2.6 Hz, 1H), 7.08 (d, J=2.6 Hz, 1H), 6.84 (dd, J=6.3, 2.7 Hz, 1H), 6.81 (d, J=8.8 Hz, 1H), 6.76 (m, 1H), 5.80 (s, 2H); MS (ESI) m/z 262/264 ([M+H]+); MS (ESI) m/z 260/262 ([M–H]–); Anal. calcd for $C_{13}H_9ClFN_3$: C, 59.67; H, 3.47; N, 16.06. Found: C, 59.24; H, 3.41 N, 15.87.

B. 1-{2-amino-5-[(3-chloro-4-fluorophenyl)amino]phenyl}propan-1-one

To a stirred solution of 2-amino-5-[(3-chloro-4-fluorophenyl)amino]benzonitrile (5.90 g, 22.5 mmol) in THF (120 mL) at 0° C. was slowly added ethyl magnesium bromide (80 mL, 80.0 mmol). The solution was stirred at room temperature for 2 days and quenched with 1N HCl. The resulting mixture was made alkaline with sodium bicarbonate solution (sat.) and extracted several times with ethyl acetate. The combined organic layers were dried over magnesium sulfate. Flash silica gel column separation using 20% ethyl acetate/hexane followed by trituration with ether gave 1-{2-amino-5-[(3-chloro-4-fluorophenyl)amino]phenyl}propan-1-one as a yellow solid (2.48 g, 38%). $^1$H NMR (DMSO-$d_6$): δ 7.78 (s, 1H), 7.48 (d, J=2.5 Hz, 1H), 7.18 (t, J=9.1 Hz, 1H), 7.12 (dd, J=8.8, 2.6 Hz, 1H), 7.04 (s, 2H), 6.81 (m, 1H), 6.79 (d, J=8.8 Hz, 1H), 6.73 (m, 1H), 2.93 (q, J=7.2 Hz, 2H), 1.07 (t, J=7.1 Hz, 3H); MS (ESI) m/z 293/295 ([M+H]+); MS (ESI) m/z 291/293 ([M–H]–); Anal. calcd for $C_{15}H_{14}ClFN_2O$: C, 61.54H, 4.82; N, 9.57. Found: C, 61.55; H, 4.68; N, 9.47.

To a stirred solution of 1-{2-amino-5-[(3-chloro-4-fluorophenyl)amino]-phenyl}propan-1-one (2.40 g, 8.20 mmol) in THF (80 mL) was added 1.0M thienyllithium (32 mL, 32 mmol) slowly at 0° C. over 20 minutes. The reaction was stirred overnight at room temperature, quenched with ammonium chloride solution (sat.), and extracted with ethyl acetate several times. The organic layer was washed with brine and dried over magnesium sulfate. The concentrated crude material was dissolved in THF (40 mL). CDI (2.66 g, 16.40 mmol) was added and the reaction was stirred overnight at room temperature. The reaction solution was partitioned between ammonium chloride solution (sat.) and ethyl acetate. The organic layer was dried over magnesium sulfate and concentrated. Flash silica gel column separation with 30% ethyl acetate/hexane followed by trituration with methylene chloride/ether gave 6-[(3-chloro-4-fluorophenyl)amino]-4-ethyl-4-thien-2-yl-1,4-dihydro-2H-3,1-benzoxazin-2-one as a white solid (0.19 g, 5%). $^1$H NMR (DMSO-$d_6$): δ 10.22 (s, 1H), 8.20 (s, 1H), 7.53 (dd, J=5.0, 1.3 Hz, 1H), 7.24 (t, J=9.0 Hz, 1H), 7.07 (dd, J=8.5, 2.3 Hz, 1H), 7.0 (m, 3H), 6.92 (dd, J=3.6, 1.3 Hz, 1H), 6.88 (m, 2H), 2.43 (m, 2H), 0.96 (t, J=7.1 Hz, 3H); MS (ESI) m/z 403/405 ([M+H]+); MS (ESI) m/z 401/403 ([M–H]–); HRMS: calcd for $C_{20}H_{16}ClFN_2O_2S$, 402.0605. found (ESI+), 403.06762. Anal. calcd for $C_{20}H_{16}ClFN_2O_2S$: C, 59.63; H, 4.00; N, 6.95. Found: C, 59.79; H, 4.35; N, 6.55.

Example 25

6-[(3-chloro-4-fluorophenyl)amino]-4-ethyl-1-methyl-4-thien-2-yl-1,4-dihydro-2H-3,1-benzoxazin-2-one To a stirred solution of 6-[(3-chloro-4-fluorophenyl)amino]-4-ethyl-4-thien-2-yl-1,4-dihydro-2H-3,1-benzoxazin-2-one (0.16 g, 0.39 mmol) in DMF (4 mL) was added potassium t-butoxide (0.05 g, 0.42 mmol) at room temperature. After 10 minutes, methyl iodide (0.05 mL, 0.80 mmol) was added. After 45 minutes, the reaction solution was quenched with ammonium chloride solution (sat) and extracted with ethyl acetate. The organic layer was washed several times with brine and dried over magnesium sulfate. The solvent was removed to give 6-[(3-chloro-4-fluorophenyl)amino]-4-ethyl-1-methyl-4-thien-2-yl-1,4-dihydro-2H-3,1-benzoxazin-2-one as a red solid (0.12 g, 73%). $^1$H NMR (DMSO-$d_6$): δ 8.31 (s, 1H), 7.53 (m, 1H), 7.27 (t, J=9.1 Hz, 1H), 7.16 (d, J=8.7 Hz, 1H), 7.10 (d, J=8.6 Hz, 1H), 7.05 (m, 1H), 7.0 (m, 2H), 6.93 (m, 2H), 3.24 (s, 3H), 2.43 (m, 2H), 0.96 (t, J=5.9 Hz, 3H); MS (ESI) m/z 417/419 ([M+H]+); MS (ESI) m/z 415/417 ([M–H]–); Anal. calcd for $C_{21}H_{18}ClFN_2O_2S$: C, 60.50; H, 4.35; N, 6.72. Found: C, 60.22; H, 4.34; N, 6.63.

Example 26

5-fluoro-3-[(1-methyl-2-oxo-1,2-dihydrospiro[3,1-benzoxazine-4,1'-cyclopentan]-6-yl)amino]benzonitrile A. spiro[4H-3,1-benzoxazine-4,1'-cyclopentan]-2(1H)-one To a stirred solution of magnesium turnings (19.44 g, 800 mmol) and a catalytic amount of iodine in ether (500 mL) was slowly added 1,4-dibromobutane (24.0 mL, 200 mmol). The reaction was stirred until reflux ceased. The magnesium was decanted and the solution was slowly added to 2-aminobenzoic acid methyl ester (8.0 mL, 61.70 mmol) in THF (600 mL) at 0° C. The solution was stirred overnight at room temperature, quenched with ammonium chloride solution (sat.) and extracted several times with ethyl acetate. The combined organic layers were washed with brine, dried over magnesium sulfate and concentrated. The crude material was taken up in THF (150 mL) and CDI (9.17 g, 56.53 mmol) was added. The reaction mixture was stirred overnight at room temperature and partitioned between ammonium chloride solution (sat) and ethyl acetate. The organic layer was dried over magnesium sulfate and concentrated. Flash silica gel column separation with 20% ethyl acetate/hexane gave spiro[4H-3,1-benzoxazine-4,1'-cyclopentan]-2(1H)-one as a white solid (2.60 g, 27%). $^1$H NMR (DMSO-$d_6$): δ 10.15 (s, 1H), 7.28 (m, 2H), 7.03 (t, J=7.6 Hz, 1H), 6.89 (dd, J=7.9, 0.8 Hz, 1H), 2.15 (m, 2H), 2.07 (m, 2H), 1.90 (m, 4H); MS (ESI) m/z 204 ([M+H]+); Anal. calcd for $C_{12}H_{13}NO_2$: C, 70.92; H, 6.45 N, 6.89. Found: C, 70.84; H, 6.42; N, 6.77.

B. 6-Nitrospiro [1-methyl-4H-3,1-benzoxazine-4,1'-cyclopentan]-2(1H)-one

Prepared from spiro[4H-3,1-benzoxazine-4,1'-cyclopentan]-2(1H)-one, using the nitration protocol described in example 1. $^1$H NMR (DMSO-$d_6$): δ 8.27 (dd, J=9.0, 2.6 Hz, 1H), 8.17 (d, J=2.5 Hz, 1H), 7.34 (d, J=9.0 Hz, 1H), 3.42 (s, 3H), 2.20 (m, 4H), 1.94 (m, 4H); MS (ESI) m/z 263 ([M+H]+); Anal. calcd for $C_{13}H_{14}N_2O_4$: C, 59.54; H, 5.38; N, 10.68. Found: C, 58.58; H, 5.18; N, 10.55.

To a stirred suspension of 6-nitrospiro[1-methyl-4H-3,1-benzoxazine-4,1'-cyclopentan]-2(1H)-one (1.90 g, 7.24 mmol) and 10% palladium on carbon (0.03 g) in methanol at 0° C. was added sodium borohydride (0.55 g, 14.49 mmol) portionwise. After stirring for 30 minutes, the reaction mixture was quenched with ammonium chloride solution (sat.) and extracted several times with ethyl acetate. The combined organic layers were dried over magnesium sulfate and concentrated. The crude material was taken up in methylene chloride (10 mL). 5-Fluoro-3-cyanophenylboronic acid (0.49 g, 2.97 mmol), pyridine (0.25 mL, 3.09 mmol), and copper (II) acetate (0.36 g, 1.98 mmol) were added. The reaction mixture was stirred at room temperature for 2 days and partitioned between ammonium chloride solution (sat) and methylene chloride. The organic layer was washed with 1N sodium hydroxide solution twice, dried over magnesium sulfate and concentrated. Flash silica gel column separation with 30% ethyl acetate/hexane gave 5-fluoro-3-[(1-methyl-2-oxo-1,2-dihydrospiro[3,1-benzoxazine-4,1'-cyclopentan]-6-yl)amino]benzonitrile as yellow solid (0.10 g, 4%). $^1$H NMR (DMSO-$d_6$): δ 8.75 (s, 1H), 7.23 (dd, J=8.7, 2.3 Hz, 1H), 7.09 (m, 4H), 6.98 (dt, J=11.6, 2.2 Hz, 1H), 3.29 (s, 3H), 2.15 (m, 2H), 1.9 (m, 2H); MS (ESI) m/z 352 ([M+H]+); MS (ESI) m/z 350 ([M−H]−); HRMS: calcd for $C_{20}H_{18}FN_3O_2$, 351.1383. found (ESI+), 352.14616; Anal. calcd for $C_{20}H_{18}FN_3O_2$: C, 68.36; H, 5.16; N, 11.96. Found: C, 67.10; H, 5.20; N, 11.56.

Example 27

6-[(4-bromophenyl)amino]-4-(4-chlorophenyl)-1,4-dimethyl-1,4-dihydro-2H-3,1-benzoxazin-2-one A. 4-(4-chlorophenyl)-4-methyl-1,4-dihydro-2H-3,1-benzoxazin-2-one To a stirred solution of 1-(2-aminophenyl)-ethanone (8.00 g, 59.20 mmol) in THF (200 mL) at 0° C. was slowly added 4-chlorophenyl magnesium bromide (1.0 M, 178 mL, 178 mmol) in ether. The reaction was allowed to warm to room temperature. After 3 hours, the reaction mixture was quenched with ammonium chloride solution (sat.) and extracted several times with ethyl acetate. The combined organic layers were dried over magnesium sulfate and concentrated. The crude solid was taken up in THF (200 mL) and CDI (10.56 g, 65.10 mmol) was added. The reaction solution was stirred overnight at room temperature, poured into 1N HCl, and extracted several times with ethyl acetate. The combined organic layers were dried over magnesium sulfate and trituration with ether gave 4-(4-chlorophenyl)-4-methyl-1,4-dihydro-2H-3,1-benzoxazin-2-one as a tan solid (5.19 g, 32%). $^1$H NMR (DMSO-$d_6$): δ 10.30 (s, 1H), 7.46 (m, 3H), 7.36 (td, J=7.7, 1.0 Hz, 1H), 7.25 (d, J=8.6 Hz, 2H), 7.15 (t, J=7.6 Hz, 1H), 6.92 (d, J=7.7 Hz, 1H), 1.94 (s, 3H); MS (ESI) m/z [M+H]+=(274/276); MS (ESI) m/z [M−H]−=(272/274); Anal. calcd for $C_{15}H_{12}ClNO_2$: C, 65.82; H, 4.42; N, 5.12. Found: C, 65.38; H, 4.58; N, 5.00.

B. 4-(4-chlorophenyl)-4-methyl-6-nitro-1,4-dihydro-2H-3,1-benzoxazin-2-one

To a stirred suspension of 4-(4-chlorophenyl)-4-methyl-1,4-dihydro-2H-3,1-benzoxazin-2-one (5.15 g, 18.80 mmol) in a mixture of glacial acetic acid (15 mL) and concentrated sulfuric acid (15 mL) was slowly added concentrated nitric acid (3 mL). After 10 minutes the reaction was poured over ice and brine (100 mL) and filtered. Trituration of the solid with ethyl acetate/ether gave 4-(4-chlorophenyl)-4-methyl-6-nitro-1,4-dihydro-2H-3,1-benzoxazin-2-one as a tan solid (1.92 g, 32%). $^1$H NMR (DMSO-$d_6$): δ 11.04 (s, 1H), 8.29 (m, 2H), 7.47 (dd, J=6.6, 2.0 Hz, 2H), 7.32 (dd, J=6.7, 2.1 Hz, 2H), 7.13 (d, J=9.5 Hz, 1H), 2.06 (s, 3H); MS (ESI) m/z [M+H]+(319/321); MS (ESI) m/z [M−H]− (317/319); Anal. calcd for $C_{15}H_{11}ClN_2O_4$: C, 56.53; H, 3.48; N, 8.79. Found: C, 55.43; H, 3.37; N, 8.78.

C. 4-(4-chlorophenyl)-1,4-dimethyl-6-nitro-1,4-dihydro-2H-3,1-benzoxazin-2-one

Prepared from 4-(4-chlorophenyl)-4-methyl-6-nitro-1,4-dihydro-2H-3,1-benzoxazin-2-one according to the alkylation procedure described in example 1. $^1$H NMR (DMSO-$d_6$): δ 8.37 (dd, J=8.9, 2.6 Hz, 1H), 8.30 (d, J=2.5 Hz, 1H), 7.47 (m, 2H), 7.39 (d, J=9.0 Hz, 1H), 7.31 (m, 2H), 3.26 (s, 3H), 2.06 (s, 3H); MS (ESI) m/z 333 ([M+H]+); Anal. calcd for $C_{16}H_{13}ClN_2O_4$: C, 57.76; H, 3.94; N 8.42. Found: C, 57.85; H, 3.89; N, 8.23.

D. 6-amino-4-(4-chlorophenyl)-1,4-dimethyl-1,4-dihydro-2H-3,1-benzoxazin-2-one

Prepared from 4-(4-chlorophenyl)-1,4-dimethyl-6-nitro-1,4-dihydro-2H-3,1-benzoxazin-2-one according to the reduction procedure described in example 1. $^1$H NMR (DMSO-$d_6$): δ 7.44 (dd, J=6.6, 1.9 Hz, 2H), 7.25 (dd, J=6.7, 2.0 Hz, 2H), 6.83 (d, J=9.3 Hz, 1H), 6.63 (m, 2H), 5.01 (s, 2H), 3.07 (s, 3H), 1.84 (s, 3H); MS (ESI) m/z 303/305 ([M+H]+); Anal. calcd for $C_{16}H_{15}ClN_2O_2$: C, 63.47; H, 4.99 N, 9.25. Found: C, 63.39; H, 5.11; N, 8.96.

E. 6-[(4-bromophenyl)amino]-4-(4-chlorophenyl)-1,4-dimethyl-1,4-dihydro-2H-3,1-benzoxazin-2-one Prepared from 6-amino-4-(4-chlorophenyl)-1,4-dimethyl-1,4-dihydro-2H-3,1-benzoxazin-2-one and 4-bromophenyl boronic acid according to the coupling procedure described in example 1. MS (ESI) m/z [M+H]+ (457/459/461); MS (ESI) m/z [M−H]−(455/457/459); Anal. calcd for $C_{22}H_{18}BrClN_2O_2$: C, 57.73; H,3.96; N6.12. Found: C, 56.88; H, 3.90; N, 5.70.

Example 28

6-[(4-bromophenyl)amino]-4-ethyl-1-methyl-4-thien-2-yl-1,4-dihydro-2H-3,1-benzoxazin-2-one Prepared 6-amino-4-ethyl-1-methyl-4-thien-2-yl-1,4-dihydro-2H-3,1-benzoxazin-2-one and 4-bromophenyl boronic acid according to the coupling procedure described in Example 1. MS (ESI) m/z 443/445 ([M+H]+); MS (ESI) m/z 441/443 ([M−H]−); Anal. calcd for $C_{21}H_{19}BrN_2O_2S$: C, 56.89; H 4.32; N 6.32. Found: C, 56.65; H, 4.09; N, 6.18.

Example 29

6-[(3,4-difluorophenyl)amino]-4,4-diethyl-1-methyl-1,4-dihydro-2H-3,1-benzoxazine-2-thione To a stirred solution of 6-[(3,4-difluorophenyl)amino]-4,4-diethyl-1-methyl-1,4-dihydro-2H-3,1-benzoxazin-2-one (0.10 g, 0.29 mmol) in toluene (5 mL) was added Lawesson's reagent (0.09 g, 0.23 mmol). The reaction mixture was heated to reflux overnight and partitioned between ammonium chloride solution (sat.) and ethyl acetate. The organic layer was dried over magnesium sulfate and concentrated. Flash silica gel column separation using 20% ethyl acetate/hexane followed by trituration with ether gave 6-[(3,4-difluorophenyl)amino]-4,4-diethyl-1-methyl-1,4-dihydro-2H-3,1-benzoxazine-2-thione as a white solid (0.03 g, 31%). $^1$H NMR (DMSO-$d_6$): δ 8.44 (s, 1H), 7.32 (q, J=9.1 Hz, 1H), 7.19 (d, J=8.8 Hz, 1H), 7.12 (dd, J=8.8, 2.4 Hz, 1H), 6.97 (m, 1H), 6.88 (d, J=2.4 Hz, 1H), 6.81 (m, 1H), 3.75 (s, 3H), 1.99 (m, 4H), 0.85 (t, J=7.3 Hz, 6H); MS (ESI) m/z 363 ([M+H]+); MS (ESI) m/z 361 ([M−H]−); Anal. calcd for $C_{19}H_{20}F_2N_2OS$: C, 62.96; H, 5.56; N, 7.73. Found: C, 62.15; H, 5.65 N, 7.39.

Example 30

6-[(4-bromophenyl)amino]-1,4,4-trimethyl-1,4-dihydro-2H-3,1-benzoxazine-2-thione Prepared from 6-[(4-bromophenyl)amino]-1,4,4-trimethyl-1,4-dihydro-2H-3,1-benzoxazin-2-one using the similar procedure described in example 29. $^1$H NMR (DMSO-$d_6$): δ 8.49 (s, 1H), 7.39 (d, J=8.8 Hz, 2H), 7.19 (d, J=8.8 Hz, 1H), 7.12 (dd, J=8.8, 2.3 Hz, 1H), 7.00 (m, 3H), 3.75 (s, 3H), 1.60 (s, 6H); MS (ESI) m/z 377/379 ([M+H]+); MS (ESI) m/z 375/377 ([M−H]−); Anal. calcd for $C_{17}H_{17}BrN_2OS$: C, 54.12; H, 4.54; N, 7.42. Found: C, 53.61; H, 4.36; N, 7.22.

Examples 31 to 60 were prepared according to the procedures described in example 1 or example 2.

Example 31

4-[(1,4,4-trimethyl-2-oxo-1,4-dihydro-2H-3,1-benzoxazin-6-yl)amino]benzonitrile MS (ESI) m/z [M+H]+ (308); MS (ESI) m/z [M−H]− (306); Anal. calcd for $C_{18}H_{17}N_3O_2$: C, 70.34; H, 5.58; N, 13.67. Found: C, 69.88; H, 5.43; N, 13.18.

Example 32

6-[(2,4-dichlorophenyl)amino]-1,4,4-trimethyl-1,4-dihydro-2H-3,1-benzoxazin-2-one MS (ESI) m/z 351/353/355 ([M+H]+); MS (ESI) m/z 349/351/353 ([M−H]−); Anal. calcd for $C_{17}H_{16}Cl_2N_2O_2$: C, 58.13; H, 4.59; N, 7.98. Found: C, 57.86; H, 4.60 N, 7.69.

Example 33

1,4,4-trimethyl-6-(1-naphthylamino)-1,4-dihydro-2H-3,1-benzoxazin-2-one

MS (ESI) m/z 333 ([M+H]+); MS (ESI) m/z 331 ([M−H]−); Anal. calcd for $C_{21}H_{20}N_2O_2$: C, 75.88; H, 6.06; N, 8.43. Found: C, 74.64; H, 5.94; N, 8.03.

Example 34

6-[(4-bromophenyl)amino]-1,4-dimethyl-4-thien-2-yl-1,4-dihydro-2H-3,1-benzoxazin-2-one MS (ESI) m/z 427/429 ([M−H]−).

Example 35

6-[(3,4-dichlorophenyl)amino]-1,4,4-trimethyl-1,4-dihydro-2H-3,1-benzoxazin-2-one MS (ESI) m/z 351/353/355 ([M+H]+); MS (ESI) m/z 349/351/353 ([M−H]−); Anal. calcd for $C_{17}H_{16}Cl_2N_2O_2$: C, 58.13; H, 4.59; N, 7.98. Found: C, 58.11; H, 4.68; N, 7.68.

Example 36

6-[(2-chloro-4-nitrophenyl)amino]-1,4,4-trimethyl-1,4-dihydro-2H-3,1-benzoxazin-2-one MS (ESI) m/z 362/364 ([M+H]+); MS (ESI) m/z 360/362 ([M−H]−); Anal. calcd for $C_{17}H_{16}ClN_3O_4$: C, 56.44; H, 4.46; N, 11.61. Found: C, 54.92; H, 4.40 N, 10.69.

Example 37

6-[(2-methoxyphenyl)amino]-1,4,4-trimethyl-1,4-dihydro-2H-3,1-benzoxazin-2-one MS (ESI) m/z 313 ([M+H]+); Anal. calcd for $C_{18}H_{20}N_2O_3$: C, 69.21; H, 6.45 N, 8.97. Found: C, 67.78; H, 6.45; N, 8.95.

Example 38

1,4,4-trimethyl-6-[(2-methylphenyl)amino]-1,4-dihydro-2H-3,1-benzoxazin-2-one MS (ESI) m/z 297 ([M+H]+); MS (ESI) m/z 295 ([M−H]−); Anal. calcd for $C_{18}H_{20}N_2O_2$: C, 72.95; H, 6.80; N, 9.45. Found: C, 72.69; H, 6.90; N, 9.41.

Example 39

6-[(2-bromophenyl)amino]-1,4,4-trimethyl-1,4-dihydro-2H-3,1-benzoxazin-2-one MS (ESI) m/z 361/363 ([M+H]+); MS (ESI) m/z 359/361 ([M−H]−).

Example 40

4-(4-chlorophenyl)-6-[(4-chlorophenyl)amino]-1,4-dimethyl-1,4-dihydro-2H-3,1-benzoxazin-2-one MS (ESI) m/z 413/415/417 ([M+H]+); MS (ESI) m/z 411/413/415 ([M−H]−); Anal. calcd for $C_{22}H_{18}Cl_2N_2O_2$: C, 63.93; H, 4.39; N, 6.78. Found: C, 62.32; H, 4.44; N, 5.95.

Example 41

6-[(4-bromo-2-chlorophenyl)amino]-1,4,4-trimethyl-1,4-dihydro-2H-3,1-benzoxazin-2-one MS (ESI) m/z 395/397/399 ([M+H]+); MS (ESI) m/z 393/395/397 ([M−H]−).

Example 42

6-[(4-ethoxyphenyl)amino]-1,4,4-trimethyl-1,4-dihydro-2H-3,1-benzoxazin-2-one

MS (ESI) m/z [M+H]+ (327); Anal. calcd for $C_{19}H_{22}N_2O_3$: C, 69.92; H, 6.79 N, 8.58. Found: C, 69.37; H, 6.62; N, 8.07.

Example 43

6-[(4-bromophenyl)amino]-1-ethyl-4,4-dimethyl-1,4-dihydro-2H-3,1-benzoxazin-2-one MS (ESI) m/z 375/377 ([M+H]+); MS (ESI) m/z 373/375 ([M−H]−).

Example 44

6-[(2-ethylphenyl)amino]-1,4,4-trimethyl-1,4-dihydro-2H-3,1-benzoxazin-2-one

MS (ESI) m/z [M+H]+ (311); MS (ESI) m/z [M−H]− (309); Anal. calcd for $C_{19}H_{22}N_2O_2$: C, 73.52; H, 7.14; N, 9.02. Found: C, 72.96; H, 7.20; N, 8.55.

Example 45

1,4,4-Trimethyl-6-(4-phenoxy-phenylamino)-1,4-dihydro-benzo[d][1,3]oxazin-2-one

MS (ESI) m/z 389 ([M+H]+); Anal. calcd for $C_{24}H_{24}N_2O_3$: C, 74.21; H, 6.23 N, 7.21. Found: C, 74.01; H, 6.17; N, 6.43.

Example 46

6-(4-Hydroxy-phenylamino)-1,4,4-trimethyl-1,4-dihydro-benzo[d][1,3]oxazin-2-one

MS (ESI) m/z 299 ([M+H]+); MS (ESI) m/z 297 ([M−H]−); Anal. calcd for $C_{17}H_{18}N_2O_3$: C, 68.44; H, 6.08; N, 9.39. Found: C, 66.84; H, 5.91; N, 8.94.

Example 47

6-[(4-bromophenyl)amino]-4,4-bis(4-chlorophenyl)-1-methyl-1,4-dihydro-2H-3,1-benzoxazin-2-one MS (ESI) m/z 553/555/557 ([M+H]+); MS (ESI) m/z 551/553/555 ([M−H]−); Anal. calcd for $C_{27}H_{19}BrCl_2N_2O_2$: C, 58.51; H, 3.46; N, 5.05. Found: C, 55.00; H, 3.33 N, 4.49.

Example 48

4,4-bis(4-chlorophenyl)-6-[(3-chlorophenyl)amino]-1-methyl-1,4-dihydro-2H-3,1-benzoxazin-2-one MS (ESI) m/z 509/511/513 ([M+H]+); MS (ESI) m/z 507/509/511 ([M−H]−); Anal. calcd for $C_{27}H_{19}Cl_3N_2O_2$: C, 63.61; H, 3.76; N, 5.49. Found: C, 62.98; H, 3.80; N, 5.00.

Example 49

4-benzyl-6-[(4-bromophenyl)amino]-1,4-dimethyl-1,4-dihydro-2H-3,1-benzoxazin-2-one MS (ESI) m/z 437/439 ([M+H]+); MS (ESI) m/z 435/437 ([M−H]−); Anal. calcd for $C_{23}H_{21}BrN_2O_2$: C, 63.17; H, 4.84; N, 6.41. Found: C, 63.02; H, 4.94; N, 6.04.

Example 50

4-benzyl-6-[(2-chlorophenyl)amino]-1,4-dimethyl-1,4-dihydro-2H-3,1-benzoxazin-2-one MS (ESI) m/z 393/395 ([M+H]+); MS (ESI) m/z 391/393 ([M−H]−); Anal. calcd for $C_{23}H_{21}ClN_2O_2$: C, 70.31; H, 5.39; N, 7.13. Found: C, 68.77; H, 5.32; N, 6.61.

Example 51

4-benzyl-6-[(3-chlorophenyl)amino]-1,4-dimethyl-1,4-dihydro-2H-3,1-benzoxazin-2-one MS (ESI) m/z 393/395 ([M+H]+); MS (ESI) m/z 391/393 ([M−H]−); Anal. calcd for $C_{23}H_{21}ClN_2O_2$: C, 70.31; H, 5.39; N, 7.13. Found: C, 65.97; H, 5.08; N, 6.53.

Example 52

6-[(4-bromophenyl)amino]-1-isopropyl-4,4-dimethyl-1,4-dihydro-2H-3,1-benzoxazin-2-one MS (ESI) m/z 389/391 ([M+H]+); MS (ESI) m/z 387/389 ([M−H]−).

Example 53

6-[(4-chlorophenyl)amino]-8-methoxy-1,4,4-trimethyl-1,4-dihydro-2H-3,1-benzoxazin-2-one MS (ESI) m/z 347/349 ([M+H]+); MS (ESI) m/z 345/347 ([M−H]−).

Example 54

4-(4-chlorophenyl)-8-methoxy-4-methyl-6-nitro-1,4-dihydro-2H-3,1-benzoxazin-2-one MS (ESI) m/z 347/349 ([M−H]−); Anal. calcd for $C_{16}H_{13}ClN_2O_5$: C, 55.11H, 3.76; N, 8.03. Found: C, 54.77; H, 3.87; N, 7.82.

Example 55

4-(4-chlorophenyl)-6-[(3-chlorophenyl)amino]-4-ethyl-1,4-dihydro-2H-3,1-benzoxazin-2-one MS (ESI) m/z 411/413/415 ([M–H]–); Anal. calcd for $C_{22}H_{18}Cl_2N_2O_2$: C, 63.93H, 4.39; N, 6.78. Found: C, 63.24; H, 4.43; N, 6.50.

Example 56

4-(4-chlorophenyl)-6-[(3-chlorophenyl)amino]-4-ethyl-1-methyl-1,4-dihydro-2H-3,1-benzoxazin-2-one MS (ESI) m/z 427/429/431 ([M+H]+); MS (ESI) m/z 425/427/429 ([M–H]–).

Example 57

4-(4-chlorophenyl)-6-[(3-chlorophenyl)amino]-1,4,8-trimethyl-1,4-dihydro-2H-3,1-benzoxazin-2-one MS (ESI) m/z 427/429/432 ([M+H]+); MS (ESI) m/z 425/427/429 ([M–H]–); Anal. calcd for $C_{23}H_{20}Cl_2N_2O_2$: C, 64.65; H, 4.72; N, 6.56. Found: C, 64.34; H, 4.74; N, 6.39.

Example 58

6-[(3-chlorophenyl)amino]-4-ethyl-4-phenyl-1,4-dihydro-2H-3,1-benzoxazin-2-one

MS (ESI) m/z [M+H]+ (379/381); Anal. calcd for $C_{22}H_{19}ClN_2O_2$: C, 69.75H, 5.05; N, 7.39. Found: C, 69.15; H, 4.75; N, 7.11.

Example 59

6-[(3-chlorophenyl)amino]-4-ethyl-1-methyl-4-phenyl-1,4-dihydro-2H-3,1-benzoxazin-2-one MS (ESI) m/z 393/395 ([M+H]+).

Example 60

4-(4-chlorophenyl)-6-[(3-chlorophenyl)amino]-8-methoxy-1,4-dimethyl-1,4-dihydro-2H-3,1-benzoxazin-2-one MS (ESI) m/z [M+H]+(443/445/447); Anal. calcd for $C_{23}H_{20}C_{12}N_2O_3$: C, 62.31; H, 4.55; N, 6.32. Found: C, 62.01; H, 4.56; N, 5.93.

Examples 61-68

The compounds in the following examples were prepared from 6-Amino-1,4,4-trimethyl-1,4-dihydro-2H-3,1-benzoxazin-2-one and the corresponding aryl boronic acid according to the procedure described in example 1.

The compounds were purified using high performance liquid chromatography (HPLC) using a YMC™ combi pro C18 Column (5 micron, 12 nanometers (nm), 50×4.4 millimeters (mm)). Mobile Phase A: acetonitrile with 0.1% TFA. Mobile Phase B: Water with 0.1% TFA Conditions: 1 mL/min., 10% A to 100% A 10 minute linear gradient, 100% A for 3 minutes. UV detection was at 220 and 254 nm.

| Compounds | Retention Time | MS (ES) m/z |
|---|---|---|
| 6-(3-Chloro-phenylamino)-1,4,4-trimethyl-1,4-dihydro-benzo[d][1,3]oxazin-2-one | 8.43 | 316 |
| 6-(4-Fluoro-phenylamino)-1,4,4-trimethyl-1,4-dihydro-benzo[d][1,3]oxazin-2-one | 7.34 | 300 |
| 6-(4-Methoxy-phenylamino)-1,4,4-trimethyl-1,4-dihydro-benzo[d][1,3]oxazin-2-one | 7.03 | 312 |
| 1,4,4-Trimethyl-6-p-tolylamino-1,4-dihydro-benzo[d][1,3]oxazin-2-one | 7.90 | 296 |
| 6-(4-Bromo-phenylamino)-1,4,4-trimethyl-1,4-dihydro-benzo[d][1,3]oxazin-2-one | 8.33 | 360 |
| 6-(3,4-Difluoro-phenylamino)-1,4,4-trimethyl-1,4-dihydro-benzo[d][1,3]oxazin-2-one | 7.69 | 318 |
| 6-(3,5-Difluoro-phenylamino)-1,4,4-trimethyl-1,4-dihydro-benzo[d][1,3]oxazin-2-one | 7.88 | 318 |
| 6-(2-Fluoro-3-methoxy-phenylamino)-1,4,4-trimethyl-1,4-dihydro-benzo[d][1,3]oxazin-2-one | 7.19 | 330 |

Example 69

6-(3-chloro-4-fluorophenoxy)-4,4-diethyl-1-methyl-1,4-dihydro-benzo[d][1,3]oxazin-2-one A. 4,4-diethyl-1-methyl-2-oxo-1,4-dihydro-2H-3,1-benzoxazin-6-ylboronic acid To a stirred solution of 4,4-diethyl-2-oxo-1,4-dihydro-2H-3,1-benzoxazin-6-ylboronic acid (4.85 g, 19.50 mmol) in THF (100 mL) at 0° C. was added sodium hydride (3.12 g-60%, 78 mmol). After 10 minutes, methyl iodide (9.7 mL, 156.0 mmol) was added and the reaction was allowed to warm to room temperature After one week the reaction was quenched with ammonium chloride solution (sat.) and extracted with ethyl acetate several times. The organic layers were washed with brine, dried over magnesium sulfate and concentrated. Trituration with ether gave 4,4-diethyl-1-methyl-2-oxo-1,4-dihydro-2H-3,1-benzoxazin-6-ylboronic acid as a yellow solid (3.97 g, 77%). $^1$H NMR (DMSO-$d_6$): δ 8.03 (s, 2H), 7.78 (dd, J=8.2, 1.3 Hz, 1H), 7.60 (d, J=1.3 Hz, 1H), 7.05 (d, J=8.3 Hz, 1H), 3.28 (s, 3H), 1.99 (m, 4H), 0.78 (t, J=7.4 Hz, 6H). MS (ESI) m/z 264 ([M+H]+); MS (ESI) m/z 262 ([M–H]–); Anal. calcd for $C_{13}H_{18}BNO_4$: C, 59.35; H, 6.90; N, 5.32. Found: C, 58.97; H, 6.98; N, 4.73.

B. 4,4-diethyl-6-hydroxy-1-methyl-1,4-dihydro-2H-3,1-benzoxazin-2-one

To a stirred suspension of 4,4-diethyl-1-methyl-2-oxo-1,4-dihydro-2H-3,1-benzoxazin-6-yl boronic acid (3.97 g, 15.09 mmol) in a 15% acetone and 85% water mixture solution (80 mL) was added sodium bicarbonate (3.80 g, 45.27 mmol). The resulting suspension was cooled to 0° C. and Oxone (9.09 g, 14.80 mmol) was added portionwise over 20 minutes. After 45 minutes, sodium bisulfite (4.25 g, 4.10 mmol) was added. The solution was stirred for an additional 10 minutes, diluted with water and extracted several times with ethyl acetate. The organic layers were dried over magnesium sulfate and concentrated. Trituration with ether gave 4,4-diethyl-6-hydroxy-1-methyl-1,4-dihydro-2H-3,1-benzoxazin-2-one as a white solid (2.45 g, 69%). ¹H NMR (DMSO-d$_6$): δ 9.32 (s, 2H), 6.90 (d, J=8.8 Hz, 1H), 6.75 (dd, J=8.7, 2.6 Hz, 1H), 6.58 (d, J=2.7 Hz, 1H), 3.22 (s, 3H), 1.99 (m, 4H), 0.79 (t, J=7.3 Hz, 6H). MS (ESI) m/z 236 ([M+H]+); MS (ESI) m/z 234 ([M−H]−); Anal. calcd for C$_{13}$H$_{17}$NO$_3$: C, 66.36; H, 7.28; N, 5.95. Found: C, 66.02; H, 7.34; N, 5.74.

C. 6-(3-chloro-4-fluorophenoxy)-4,4-diethyl-1-methyl-1,4-dihydro-benzo[d][1,3]oxazin-2-one To a stirred solution of 4,4-diethyl-6-hydroxy-1-methyl-1,4-dihydro-2H-3,1-benzoxazin-2-one (0.30 g, 1.28 mmol) and 3-chloro-4-fluorophenylboronic acid (0.67 g, 3.83 mmol) in methylene chloride (15 mL) was added triethylamine (0.6 mL, 4.3 mmol) and copper (II) acetate (0.46 g, 2.56 mmol). The reaction mixture was stirred at room temperature for 6 days and partitioned between ammonium chloride solution (sat.) and methylene chloride. The organic layer was washed with 1N sodium hydroxide solution, dried over magnesium sulfate and concentrated to give 6-(3-chloro-4-fluorophenoxy)-4,4-diethyl-1-methyl-1,4-dihydro-benzo[d][1,3]oxazin-2-one as a yellow oil (0.04 g, 9%). ¹H NMR (DMSO-d$_6$): δ 7.45 (t, J=9.1 Hz, 1H), 7.21 (dd, J=6.2, 3.0 Hz, 1H), 7.13 (d, J=8.7 Hz, 1H), 7.08 (m, 2H), 6.99 (m, 1H), 3.29 (s, 3H), 2.01 (m, 2H), 1.88 (m, 2H), 0.79 (t, J=7.3 Hz, 6H). MS (ESI) m/z 364/366 ([M+H]+); HRMS: calcd for C$_{19}$H$_{19}$ClFNO$_3$, 363.1037. found (ESI+), 364.1106.

Example 70

3-(4,4-diethyl-1-methyl-2-oxo-1,4-dihydro-2H-benzo[d][1,3]oxazin-6-yloxy)-5-fluoro-benzonitrile Prepared from 4,4-diethyl-6-hydroxy-1-methyl-1,4-dihydro-2H-3,1-benzoxazin-2-one and 3-cyano-5-fluorobenzeneboronic acid according to the coupling procedure described in example 69. A white solid, ¹H NMR (DMSO-d$_6$): δ 7.61 (m, 1H), 7.29 (s, 1H), 7.23 (dt, J=10.3, 2.3 Hz, 1H), 7.17 (m, 2H), 7.13 (m, 1H), 3.30 (s, 3H), 2.02 (m, 2H), 1.89 (m, 2H), 0.79 (t, J=7.2 Hz, 6H). MS (ESI) m/z 355 ([M+H]+); HRMS: calcd for C$_{20}$H$_{19}$FN$_2$O$_3$, 354.1380. found (ESI+), 355.14578.

Example 71

(4,4-dimethyl-2-oxo-1,4-dihydro-2H-3,1-benzoxazin-6-yl)-2,3-dichlorobenzenesulfonate To a stirred solution of 6-hydroxy-4,4-dimethyl-1,4-dihydro-2H-3,1-benzoxazin-2-one (1.00 g, 5.17 mmol), prepared according to the procedure in example 69, in methylene chloride (25 mL) at 0° C. was added triethylamine (0.9 mL, 6.45 mmol). After 10 minutes, 2,3-dichlorobenzenesulfonyl chloride (1.27 g, 5.17 mmol) was added. The solution was stirred for one hour, then partitioned between ammonium chloride solution (sat.) and methylene chloride. The organic layer was dried over magnesium sulfate and concentrated. Trituration with ether gave (4,4-dimethyl-2-oxo-1,4-dihydro-2H-3,1-benzoxazin-6-yl)-2,3-dichlorobenzenesulfonate as a white solid (1.55 g, 75%). ¹H NMR (DMSO-d$_6$): δ 10.37 (s, 1H), 8.13 (dd, J=8.2, 1.6 Hz, 1H), 7.90 (dd, J=7.9, 1.5 Hz, 1H), 7.60 (t, J=8.05 Hz, 1H), 7.02 (dd, J=8.7, 2.6 Hz, 1H), 6.96 (d, J=2.7 Hz, 1H), 6.87 (d, J=8.7 Hz, 1H), 1.48 (s, 6H). MS (ESI) m/z 400/402/404 ([M−H]−); Anal. calcd for C$_{16}$H$_{13}$Cl$_2$NO$_5$S: C, 47.78; H, 3.26 N, 3.48. Found: C, 47.14; H, 3.46; N, 3.49.

Example 72

(1,4,4-trimethyl-2-oxo-1,4-dihydro-2H-3,1-benzoxazin-6-yl)-2,3-dichlorobenzenesulfonate To a stirred solution of (4,4-dimethyl-2-oxo-1,4-dihydro-2H-3,1-benzoxazin-6-yl)-2,3-dichlorobenzenesulfonate (0.50 g, 1.24 mmol) in dimethylformamide (DMF) (6 mL) with potassium carbonate (0.51 g, 3.72 mmol) was added methyl iodide (0.1 mL, 1.60 mmol). After stirring overnight at room temperature, the solution was then quenched with ammonium chloride solution (sat.) and extracted several times with ethyl acetate. The combined organic layers were washed with brine, dried over magnesium sulfate and concentrated. Trituration with ether gave (1,4,4-trimethyl-2-oxo-1,4-dihydro-2H-3,1-benzoxazin-6-yl)-2,3-dichlorobenzenesulfonate as a white solid (0.30 g, 59%). ¹H NMR (DMSO-d$_6$): δ 8.14 (dd, J=8.1, 1.5 Hz, 1H), 7.92 (dd, J=8.1, 1.5 Hz, 1H), 7.61 (t, J=8.1 Hz, 1H), 7.12 (s, 2H), 7.00 (m, 1H), 3.25 (s, 3H), 1.49 (s, 6H). MS (ESI) m/z 416/418/420 ([M+H]+); Anal. calcd for C$_{17}$H$_{15}$Cl$_2$NO$_5$S: C, 49.05; H, 3.63; N, 3.36. Found: C, 49.01; H, 3.44; N, 3.15.

Example 73

2,3-dichloro-N-(4,4-dimethyl-2-oxo-1,4-dihydro-2H-3,1-benzoxazin-6-yl)benzenesulfonamide To a stirred solution of 6-amino-4,4-dimethyl-1,4-dihydro-2H-3,1-benzoxazin-2-one (0.05 g, 0.24 mmol) in methylene chloride (2 mL) at 0° C. was added triethylamine (0.05 mL, 0.36 mmol). After 10 minutes, 2,3-dichlorobenzenesulfonyl chloride (0.06 g, 0.24 mmol) was added. The solution was stirred for 2 hours, then partitioned between ammonium chloride solution (sat.) and methylene chloride. The organic layer was dried over magnesium sulfate and concentrated. Flash silica gel column separation with 50% ethyl acetate/hexane followed by trituration with ether gave 2,3-dichloro-N-(4,4-dimethyl-2-oxo-1,4-dihydro-2H-3,1-benzoxazin-6-yl)benzenesulfonamide as a white solid (0.008 g, 8%). ¹H NMR (DMSO-d$_6$): δ 10.57 (s, 1H), 10.16 (s, 1H), 7.97 (dd, J=7.9, 1.3 Hz, 1H), 7.92 (dd, J=8.0, 1.3 Hz, 1H), 7.53 (t, J=8.0 Hz, 1H), 6.93 (m, 2H), 6.74 (d, J=8.4 Hz, 1H), 1.46 (s, 6H). MS (ESI) m/z 401/403/405 ([M+H]+); MS (ESI) m/z 399/401/403 ([M−H]−).

Example 74

2,3-dichloro-N-(1,4,4-trimethyl-2-oxo-1,4-dihydro-2H-3,1-benzoxazin-6-yl)benzenesulfonamide To a stirred solution of 6-amino-1,4,4-trimethyl-1,4-dihydro-2H-3,1-benzoxazin-2-one (0.15 g, 0.73 mmol) in methylene chloride (5 mL) at 0° C. was added triethylamine (0.15 mL, 1.07 mmol). After 10 minutes, 2,3-dichlorobenzenesulfonyl chloride (0.27 g, 1.10 mmol) was added. The solution was stirred for 5 hours, then partitioned between ammonium chloride solution (sat.) and methylene chloride. The organic layer was dried over magnesium sulfate and concentrated. Flash silica gel column separation with 30% ethyl acetate/hexane followed by trituration with ether gave 2,3-dichloro-N-(1,4,4-trimethyl-2-oxo-1,4-dihydro-2H-3,1-benzoxazin-6-yl)benzenesulfonamide as an off-white solid (0.015 g, 5%). ¹H NMR (DMSO-d$_6$): δ 10.17 (s, 1H), 8.02 (dd, J=7.9, 1.4 Hz, 1H), 7.93 (dd, J=8.1, 1.4 Hz, 1H), 7.56 (t, J=8.0 Hz, 1H), 7.03 (m, 3H), 3.20 (s, 3H), 1.48 (s, 6H). MS (ESI) m/z 415/417/419 ([M+H]+); MS (ESI) m/z 413/415/417 ([M−H]−).

Example 75

6-{[4-(dimethylamino)phenyl]amino}-1,4,4-trimethyl-1,4-dihydro-2H-3,1-benzoxazin-2-one Prepared from 6-amino-1,4,4-trimethyl-1,4-dihydro-2H-3,1-benzoxazin-2-one and 4-dimethylaminophenyl boronic acid according to the coupling procedure described in example 1. MS (ESI) m/z [M+H]+(326).

Example 76

6-[(4-chlorophenyl)amino]-1,4,4-trimethyl-1,4-dihydro-2H-3,1-benzoxazin-2-one

Prepared from 6-amino-1,4,4-trimethyl-1,4-dihydro-2H-3,1-benzoxazin-2-one and 4-chlorophenyl boronic acid according to the coupling procedure described in example 1. MS (ESI) m/z [M+H]+ (317/319); MS (ESI) m/z [M–H]– (315/317); Anal. calcd for $C_{17}H_{17}ClN_2O_2$: C, 64.46; H, 5.41; N, 8.84. Found: C, 63.40; H, 5.46; N, 7.97.

Example 77

6-[(2-chlorophenyl)amino]-1,4,4-trimethyl-1,4-dihydro-2H-3,1-benzoxazin-2-one

Prepared from 6-amino-1,4,4-trimethyl-1,4-dihydro-2H-3,1-benzoxazin-2-one and 2-chlorophenyl boronic acid according to the coupling procedure described in example 1. MS (ESI) m/z [M+H]+ (317/319); MS (ESI) m/z [M–H]– (315/317); Anal. calcd for $C_{17}H_{17}ClN_2O_2$: C, 64.46; H, 5.41; N8.84. Found: C, 64.42; H, 5.29; N8.76.

Example 78

Pharmacology

The compounds of this invention are tested in the relevant assay as described below and will have a potency in the range of 0.01 nM to 5 μM in the in vitro assays and 0.001 to 300 mg/kg in the in vivo assays. Table 1 provides the potency of selected examples of the invention, as determined in the assays described below.

TABLE 1

| Compound | R | $R_1$ | $R_2$ | Alk. Phos. $IC_{50}$ (nM) |
|---|---|---|---|---|
| 1 | 3'-CN, 4'-F | Et | Et | 10.4 |
| 2 | 3'-F, 5'-NO₂ | Et | Et | 10.8 |
| 3 | 3'-Cl, 4'-Cl | Me | Me | 100.0 |
| 4 | 2'-Br | Me | Me | 82.8 |
| 5 | 3'-Cl | Et | Et | 11.4 |
| 6 | 4'-OMe | Me | Me | 100.1 |
| 7 | 4'-Me | Me | Me | 98.4 |
| 8 | 3'-F, 5'-F | Et | Et | 12.0 |
| 9 | 3'-F, 4'-Cl | Et | Et | 12.0 |
| 10 | 3'-CN, 5'-F | Et | Et | 12.5 |
| 11 | 2'-Cl, 3'-Cl | Me | Me | 56.1 |
| 12 | 4'-F | Me | Me | 391.5 |
| 13 | 4'-Br | Me | Me | 54.4 |
| 14 | 3'-F, 4'-F | Me | Me | 205.7 |
| 15 | 3'-CN | Me | Me | 1000.0 |
| 16 | 4'-NO₂ | Me | Me | 309.1 |
| 17 | 4'-Cl | Me | Me | 203.7 |
| 18 | 2'-Cl | Me | Me | 70.3 |
| 19 | 4'-CN | Me | Me | 600.0 |
| 20 | 4'-Br | 4-chloro-phenyl | Me | 66.3 |
| 21 | 2'-Cl, 4'-Cl | Me | Me | 88.9 |
| 22 | 4'-Br | Thien-2-yl | Et | 75.3 |
| 23 | 4'-Br | Thien-2-yl | Me | 156.6 |
| 24 | 4'-Br | Et | Et | 45.3 |
| 25 | 2'-Cl, 4'-NO₂ | Me | Me | 165.1 |
| 26 | 2'-Me | Me | Me | 130.9 |
| 27 | 2'-Cl, 4'-Br | Me | Me | 166.3 |
| 28 | 3'-Cl | 4-chloro-phenyl | Me | 35.8 |
| 29 | 2'-Et | Me | Me | 300.0 |

A. T47D Cell Proliferation Assay

1. Objective:

Determination of progestational and antiprogestational potency was preformed by using a cell proliferation assay in T47D cells. A compound's effect an DNA synthesis in T47D cells was measured.

2. Methods:

a. Reagents:

Growth medium: DMEM:F12 (1:1) (GIBCO, BRL) supplemented with 10% (v/v) fetal bovine serum (not heat-inactivated), 100 U/mL penicillin, 100 mg/mL streptomycin, and 2 mM GlutaMax (GIBCO, BRL).

Treatment medium: Minimum Essential Medium (MEM) (#51200-038GIBCO, BRL) phenol red-free supplemented with 0.5% charcoal stripped fetal bovine serum, 100 U/mL penicillin, 200 mg/mL streptomycin, and 2 mM GlutaMax (GIBCO, BRL).

b. Cell Culture:

Stock T47 D cells were maintained in growth medium. For BrdU incorporation assay, cells were plated in 96-well plates (Falcon, Becton Dickinson Labware) at 10,000 cells/well in growth medium. After overnight incubation, the medium was changed to treatment medium and cells were cultured for an additional 24 hours before treatment. Stock compounds were dissolved in appropriate vehicle (100% ethanol or 50% ethanol/50% DMSO), subsequently diluted in treatment medium and added to the cells. Progestin and antiprogestin reference compounds were run in full dose-response curves. The final concentration of vehicle was 0.1%. In control wells, cells receive vehicle only. Antiprogestins were tested in the presence of 0.03 nM trimegestone, the reference progestin agonist. Twenty-four hours after treatment, the medium was discarded and cells were labeled with 10 mM BrdU (Amersham Life Science, Arlington Heights, Ill.) in treatment medium for 4 hours.

c. Cell Proliferation Assay:

At the end of BrdU labeling, the medium was removed and BrdU incorporation was measured using a cell proliferation ELISA kit (#RPN 250, Amersham Life Science) according to manufacturer's instructions. Briefly, cells were fixed in ethanol containing fixative for 30 minutes, followed by incubation in a blocking buffer for 30 minutes to reduce background. Peroxidase-labeled anti-BrdU antibody was added to the wells and incubated for 60 minutes. The cells were rinsed three times with PBS and incubated with 3,3',5,5'-tetramethylbenzidine (TMB) substrate for 10-20 minutes depending upon the potency of tested compounds. Then 25 μL of 1 M sulfuric acid was added to each well to stop color reaction and optical density read in a plate reader at 450 nm within 5 minutes.

3. Analysis of Results:

Square root-transformed data were used for analysis of variance and nonlinear dose response curve fitting for both agonist and antagonist modes. Huber weighting was used to downweight the effects of outliers. $EC_{50}$ or $IC_{50}$ values were calculated from the retransformed values. JMP software (SAS Institute, Inc.) was used for both one-way analysis of variance and non-linear dose response analyses in both single dose and dose response studies.

4. Reference Compounds:

Trimegestone and medroxyprogesterone acetate (MPA) were reference progestins and RU486 was the reference antiprogestin. All reference compounds were run in full dose-response curves and the $EC_{50}$ or $IC_{50}$ values were calculated.

TABLE 2

Estimated $EC_{50}$, standard error (SE), and 95% confidence intervals (CI) for individual studies

| Compound | Exp | $EC_{50}$ (nM) | SE | 95% CI lower | 95% CI upper |
|---|---|---|---|---|---|
| Trimegestone | 1 | 0.017 | 0.003 | 0.007 | 0.040 |
| | 2 | 0.014 | 0.001 | 0.011 | 0.017 |
| | 3 | 0.019 | 0.001 | 0.016 | 0.024 |
| MPA | 1 | 0.019 | 0.001 | 0.013 | 0.027 |
| | 2 | 0.017 | 0.001 | 0.011 | 0.024 |

TABLE 3

Estimated $IC_{50}$, standard error, and 95% confident interval for the antiprogestin, RU486

| Compound | Exp | $IC_{50}$ (nM) | SE | 95% CI lower | 95% CI upper |
|---|---|---|---|---|---|
| RU486 | 1 | 0.011 | 0.001 | 0.008 | 0.014 |
| | 2 | 0.016 | 0.001 | 0.014 | 0.020 |
| | 3 | 0.018 | 0.001 | 0.014 | 0.022 |

$EC_{50}$: Concentration of a compound that gives half-maximal increase in BrdU incorporation with SE; $IC_{50}$: Concentration of a compound that gives half-maximal decrease in 0.1 trimegestone induced BrdU incorporation with SE.

B. Rat Decidualization Assay

1. Objective:

This procedure was used to evaluate the effect of progestins and antiprogestins on rat uterine decidualization and compare the relative potencies of various test compounds.

2. Methods:

a. Reagents

Test compounds were dissolved in 100% ethanol and mixed with corn oil (vehicle). Stock solutions of the test compounds in oil (Mazola™) were then prepared by heating (~80° C.) the mixture to evaporate the ethanol. Test compounds were subsequently diluted with 100% corn oil or 10% ethanol in corn oil prior to the treatment of animals. No difference in decidual response was found when these two vehicles were compared.

b. Animals (RACUC Protocol#5002)

Ovariectomized mature female Sprague-Dawley rats (~60-day old and 230 g) were obtained from Taconic (Taconic Farms, N.Y.) following surgery. Ovariectomy was performed at least 10 days prior to treatment to reduce circulating sex steroids. Animals were housed under 12 hr light/dark cycle and given standard rat chow and water ad libitum.

c. Treatment

Rats were weighed and randomly assigned to groups of 4 or 5 before treatment. Test compounds in 0.2 mL vehicle were administered by subcutaneous injection in the nape of the neck or by gavage using 0.5 mL. The animals were treated once daily for seven days. For testing antiprogestins, animals were given the test compounds and an $EC_{50}$ dose of progesterone (5.6 mg/kg) during the first three days of treatment. Following decidual stimulation, animals continued to receive progesterone until necropsy four days later.

d. Dosing

Doses were prepared based upon mg/kg mean group body weight. In all studies, a control group receiving vehicle was included. Determination of dose-response curves was carried out using doses with half log increases (e.g. 0.1, 0.3, 1.0, 3.0 mg/kg).

e. Decidual Induction

Approximately 24 hours after the third injection, decidualization was induced in one of the uterine horns by scratching the antimesometrial luminal epithelium with a blunt 21 G needle. The contralateral horn was not scratched and served as an unstimulated control. Approximately 24 hours following the final treatment, rats were sacrificed by $CO_2$ asphyxiation and body weight measured. Uteri were removed and trimmed of fat. Decidualized (D-horn) and control (C-horn) uterine horns were weighed separately.

3. Analysis of Results:

The increase in weight of the decidualized uterine horn was calculated by D-horn/C-horn and logarithmic transformation was used to maximize normality and homogeneity of variance. The Huber M-estimator was used to down weight the outlying transformed observations for both dose-response curve fitting and one-way analysis of variance. JMP software (SAS Institute, Inc.) was used for both one-way ANOVA and non-linear dose-response analyses.

4. Reference Compounds:

All progestin reference compounds were run in full dose-response curves and the $EC_{50}$ for uterine wet weight was calculated.

TABLE 4

Estimated $EC_{50}$, standard error (SE), and 95% confidence intervals for individual studies

| Compound | Exp | $EC_{50}$ (mg/kg, s.c.) | SE | 95% CI lower | 95% CI upper |
|---|---|---|---|---|---|
| Progesterone | 1 | 5.50 | 0.77 | 4.21 | 7.20 |
| | 2 | 6.21 | 1.12 | 4.41 | 8.76 |
| 3-Ketodesogestrel | 1 | 0.11 | 0.02 | 0.07 | 0.16 |
| | 2 | 0.10 | 0.05 | 0.11 | 0.25 |
| | 3 | 0.06 | 0.03 | 0.03 | 0.14 |
| Levonorgestrel | 1 | 0.08 | 0.03 | 0.04 | 0.16 |
| | 2 | 0.12 | 0.02 | 0.09 | 0.17 |
| | 3 | 0.09 | 0.02 | 0.06 | 0.13 |
| | 4 | 0.09 | 0.02 | 0.06 | 0.14 |
| MPA | 1 | 0.42 | 0.03 | 0.29 | 0.60 |
| | 2 | 0.39 | 0.05 | 0.22 | 0.67 |
| | 3 | 0.39 | 0.04 | 0.25 | 0.61 |

TABLE 5

Estimated average EC$_{50}$, standard error, and 95% confidence intervals for dose-response curves of 3 reference compounds

| Compound | EC$_{50}$ (mg/kg, s.c.) | SE | 95% CI lower | 95% CI upper |
|---|---|---|---|---|
| Progesterone | 5.62 | 0.62 | 4.55 | 7.00 |
| 3-Ketodesogestrel | 0.10 | 0.02 | 0.07 | 0.14 |
| Levonorgestrel | 0.10 | 0.01 | 0.08 | 0.12 |

TABLE 6

Estimated IC$_{50}$, standard error, and 95% confident interval for the antiprogestin, RU 486

| Compound | Exp. | IC$_{50}$ (mg/kg, p.o.) | SE | 95% CI lower | 95% CI upper |
|---|---|---|---|---|---|
| RU 486 | 1 | 0.21 | 0.07 | 0.05 | 0.96 |
|  | 2 | 0.14 | 0.02 | 0.08 | 0.27 |

Concentration: Compound concentration in assay (default-mg/kg body weight)

Route of administration: Route the compound is administered to the animals

Body weight: Mean total animal body weight (default-kg)

D-horn: Wet weight of decidualized uterine horn (default-mg)

C-horn: Wet weight of control uterine horn (default-mg)

Decidual response: [(D−C)/C]×100%

Progestational activity: Compounds that induce decidualization significantly (p<0.05) compared to vehicle control are considered active Antiprogestational activity: Compounds that decrease EC$_{50}$ progesterone induced decidualization significantly (p<0.05)

EC$_{50}$ for uterine weight: Concentration of compound that gives half-maximal increase in decidual response (default-mg/kg)

IC$_{50}$ for uterine weight: Concentration of compound that gives half-maximal decrease in EC$_{50}$ progesterone induced decidual response (default-mg/kg).

C. PRE-Luciferase Assay in CV-1 cells

1. Objective:

To determine a compound's progestational or antiprogestational potency based on its effect on PRE-luciferase reporter activity in CV-1 cells co-transfected with human PR and PRE-luciferase plasmids.

2. Methods:

a. Reagents:

Growth medium: DMEM (Bio Whittaker) containing 10% (v/v) fetal bovine serum (heat inactivated), 0.1 mM MEM non-essential amino acids, 100 U/mL penicillin, 100 mg/mL streptomycin, and 2 mM GlutaMax (GIBCO, BRL).

Experimental medium: DMEM (Bio Whittaker), phenol red-free, containing 10% (v/v) charcoal-stripped fetal bovine serum (heat-inactivated), 0.1 mM MEM non-essential amino acids, 100 U/mL penicillin, 100 mg/mL streptomycin, and 2 mM GlutaMax (GIBCO, BRL).

b. Cell Culture, Transfection, Treatment, and Luciferase Assay

Stock CV-1 cells were maintained in growth medium. Co-transfection was performed using 1.2×10$^7$ cells, 5 mg pLEM plasmid with hPR-B inserted at Sph1 and BamH1 sites, 10 mg pGL3 plasmid with two PREs upstream of the luciferase sequence, and 50 mg sonicated calf thymus DNA as carrier DNA in 250 mL. Electroporation was carried out at 260 V and 1,000 mF in a Biorad Gene Pulser II. After electroporation, cells were resuspended in growth medium and plated in 96-well plate at 40,000 cells/well in 200 μL. Following overnight incubation, the medium was changed to experimental medium. Cells were then treated with reference or test compounds in experimental medium. Compounds were tested for antiprogestational activity in the presence of 3 nM progesterone. Twenty-four hours after treatment, the medium was discarded, cells were washed three times with D-PBS (GIBCO, BRL). Fifty mL of cell lysis buffer (Promega, Madison, Wis.) was added to each well and the plates were shaken for 15 minutes in a Titer Plate Shaker (Lab Line Instrument, Inc.). Luciferase activity was measured using luciferase reagents from Promega.

c. Analysis of Results:

Each treatment consisted of at least 4 replicates. Log transformed data were used for analysis of variance and nonlinear dose response curve fitting for both agonist and antagonist modes. Huber weighting was used to downweight the effects of outliers. EC$_{50}$ or IC$_{50}$ values were calculated from the retransformed values. JMP software (SAS Institute, Inc.) was used for both one-way analysis of variance and non-linear response analyses.

d. Reference Compounds:

Progesterone and trimegestone were reference progestins and RU486 was the reference antiprogestin. All reference compounds were run in full dose-response curves and the EC$_{50}$ or IC$_{50}$ values were calculated.

TABLE 6

Estimated EC$_{50}$, standard error (SE), and 95% confidence intervals (CI) for reference progestins from three individual studies

| Compound | Exp. | EC$_{50}$ (nM) | SE | 95% CI lower | 95% CI upper |
|---|---|---|---|---|---|
| Progesterone | 1 | 0.616 | 0.026 | 0.509 | 0.746 |
|  | 2 | 0.402 | 0.019 | 0.323 | 0.501 |
|  | 3 | 0.486 | 0.028 | 0.371 | 0.637 |
| Trimegestone | 1 | 0.0075 | 0.0002 | 0.0066 | 0.0085 |
|  | 2 | 0.0081 | 0.0003 | 0.0070 | 0.0094 |
|  | 3 | 0.0067 | 0.0003 | 0.0055 | 0.0082 |

TABLE 7

Estimated IC$_{50}$, standard error (SE), and 95% confident interval (CI) for the antiprogestin, RU486 from three individual studies

| Compound | Exp. | IC$_{50}$ (nM) | SE | 95% CI lower | 95% CI upper |
|---|---|---|---|---|---|
| RU486 | 1 | 0.028 | 0.002 | 0.019 | 0.042 |
|  | 2 | 0.037 | 0.002 | 0.029 | 0.048 |
|  | 3 | 0.019 | 0.001 | 0.013 | 0.027 |

Progestational activity: Compounds that increase PRE-luciferase activity significantly (p<0.05) compared to vehicle control are considered active.

Antiprogestational activity: Compounds that decrease 3 nM progesterone induced PRE-luciferase activity significantly (p<0.05)

EC$_{50}$: Concentration of a compound that gives half-maximal increase PRE-luciferase activity (default-nM) with SE.

IC$_{50}$: Concentration of a compound that gives half-maximal decrease in 3 nM progesterone induced PRE-luciferase activity (default-nM) with SE.

D. T47D Cell Alkaline Phosphatase Assay

1. Purpose:

To identify progestins or antiprogestins by determining a compound's effect on alkaline phosphatase activity in T47D cells.

2. Methods:

a. Reagents:

Culture medium: DMEM:F12 (1:1) (GIBCO, BRL) supplemented with 5% (v/v) charcoal stripped fetal bovine serum (not heat-inactivated), 100 U/mL penicillin, 100 mg/mL streptomycin, and 2 mM GlutaMax (GIBCO, BRL).

Alkaline phosphatase assay buffer:

I. 0.1 M Tris-HCl, pH 9.8, containing 0.2% Triton X-100

II. 0.1 M Tris-HCl, pH 9.8 containing 4 mM p-nitrophenyl phosphate (Sigma).

b. Cell Culture and Treatment:

Frozen T47D cells were thawed in a 37° C. water bath and diluted to 280,000 cells/mL in culture medium. To each well in a 96-well plate (Falcon, Becton Dickinson Labware), 180 µL of diluted cell suspension was added. Twenty µL of reference or test compounds diluted in the culture medium was then added to each well. When testing for progestin antagonist activity, reference antiprogestins or test compounds were added in the presence of 1 nM progesterone. The cells were incubated at 37° C. in a 5% $CO_2$/humidified atmosphere for 24 hours. Note: For high throughput screening, one concentration of each compound was tested at 0.3 mg/mL. Based on an average molecular weight of 300 g/mol for the compounds in the library, the concentration was approximately 1 mM. Subsequently, active compounds were tested in dose response assays to determine $EC_{50}$ or $IC_{50}$ c. Alkaline Phosphatase Enzyme Assay:

At the end of treatment, the medium was removed from the plate. Fifty µL of assay buffer I was added to each well. The plates were shaken in a titer plate shaker for 15 minutes. Then 150 µL of assay buffer II was added to each well. Optical density measurements were taken at 5 minute intervals for 30 minutes at a test wavelength of 405 nM.

d. Analysis of Results:

Analysis of Dose-Response Data

For reference and test compounds, a dose response curve was generated for dose (X-axis) vs. the rate of enzyme reaction (slope) (Y-axis). Square root-transformed data were used for analysis of variance and nonlinear dose response curve fitting for both agonist and antagonist modes. Huber weighting was used to downweight the effects of outliers. $EC_{50}$ or $IC_{50}$ values were calculated from the retransformed values. JMP software (SAS Institute, Inc.) was used for both one-way analysis of variance and non-linear dose response analyses in both single dose and dose response studies.

Reference Compounds: Progesterone and trimegestone were reference progestins and RU486 was the reference antiprogestin. All reference compounds were run in full dose response curves and the $EC_{50}$ or $IC_{50}$ values were calculated.

TABLE 8

Estimated $EC_{50}$, standard error (SE), and 95% confidence intervals (CI) for reference progestins from three independent experiments

| Compound | Exp. | $EC_{50}$ (nM) | SE | 95% CI lower | upper |
| --- | --- | --- | --- | --- | --- |
| Progesterone | 1 | 0.839 | 0.030 | 0.706 | 0.996 |
|  | 2 | 0.639 | 0.006 | 0.611 | 0.669 |
|  | 3 | 1.286 | 0.029 | 1.158 | 1.429 |
| Trimegestone | 1 | 0.084 | 0.002 | 0.076 | 0.091 |
|  | 2 | 0.076 | 0.001 | 0.072 | 0.080 |
|  | 3 | 0.160 | 0.004 | 0.141 | 0.181 |

TABLE 9

Estimated $IC_{50}$, standard error, and 95% confident interval for the reference antiprogestin RU486 from three independent experiments

| Compound | Exp. | $IC_{50}$ (nM) | SE | 95% CI lower | upper |
| --- | --- | --- | --- | --- | --- |
| RU486 | 1 | 0.103 | 0.002 | 0.092 | 0.115 |
|  | 2 | 0.120 | 0.001 | 0.115 | 0.126 |
|  | 3 | 0.094 | 0.007 | 0.066 | 0.134 |

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

What is claimed is:

1. A progesterone receptor modulator having the formula:

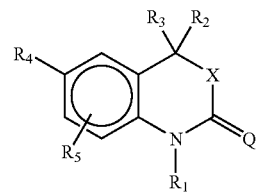

wherein:
- $R_1$ is H, OH, $C_1$ to $C_3$ alkyl, substituted $C_1$ to $C_3$ alkyl, $C_1$ to $C_3$ perfluoroalkyl, or $COR_6$;
- $R_6$ is H, $C_1$ to $C_4$ alkyl, substituted $C_1$ to $C_4$ alkyl, aryl, substituted aryl, $C_1$ to $C_4$ alkoxy, substituted $C_1$ to $C_4$ alkoxy, $C_1$ to $C_3$ aminoalkyl, or substituted $C_1$ to $C_3$ aminoalkyl;
- $R_2$ and $R_3$ are independently selected from the group consisting of H, $C_1$ to $C_6$ alkyl, substituted $C_1$ to $C_6$ alkyl, $C_1$ to $C_6$ perfluoroalkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_6$ cycloalkyl, substituted $C_3$ to $C_6$ cycloalkyl, aryl, substituted aryl, heterocyclic, and substituted heterocyclic;
- or $R_2$ and $R_3$ are fused to form:
  (i) 3 to 8 membered saturated spirocyclic ring;
  (ii) 3 to 8 membered spirocyclic ring having in its backbone one or more carbon-carbon double bonds; or
  (iii) 3 to 8 membered saturated spirocyclic ring having in its backbone one to three heteroatoms selected from the group consisting of O, S, and N;
- $R_4$ is $NHR_7$, $OR_7$, $NHSO_2R_7$, $OSO_2R_7$, $NCH_3R_7$ or $NCH_3SO_2R_7$;
- $R_7$ is selected from the group consisting of (a) and (b):
  (a) an aryl ring which is optionally substituted with one to three independent substituents selected from the group consisting of H, halogen, OH, CN, $C_1$ to $C_3$ alkyl, substituted $C_1$ to $C_3$ alkyl, $C_2$ to $C_3$ alkenyl, substituted $C_2$ to $C_3$ alkenyl, $C_2$ to $C_3$ alkynyl, substituted $C_2$ to $C_3$ alkynyl, $C_1$ to $C_3$ alkoxy, substituted $C_1$ to $C_3$ alkoxy, $C_5$ to $C_8$ aryloxy, substituted $C_5$ to $C_8$ aryloxy, $C_1$ to $C_3$ thioalkoxy, substituted $C_1$ to $C_3$ thioalkoxy, amino, $C_1$ to $C_3$ aminoalkyl, substituted $C_1$ to $C_3$ aminoalkyl, $NO_2$, $C_1$ to $C_3$ perfluoroalkyl, $COR_B$, $CR_B=NOR_C$, $OCOR_B$, $NR_CCOR_B$, and 5 or 6 membered heterocyclic ring containing in its backbone 1 to 3 heteroatoms selected from the group consisting of N, O, and S; and (b) a 5 or 6 membered heterocyclic ring containing in its backbone 1 to 3 heteroatoms selected from the group consisting of O, S, SO, $SO_2$ and N and optionally substituted with one to three independent substituents selected from the group consisting of H, halogen, OH, CN, $C_1$ to $C_3$ alkyl, substituted $C_1$ to $C_3$ alkyl, $C_2$ to $C_3$ alkenyl, substituted $C_2$ to $C_3$ alkenyl, $C_2$ to $C_3$ alkynyl, substituted $C_2$ to $C_3$ alkynyl, $C_1$ to $C_3$ alkoxy, substituted $C_1$ to $C_3$ alkoxy, $C_1$ to $C_3$ thioalkoxy, substituted $C_1$ to $C_3$ thioalkoxy, amino, $C_1$ to $C_3$ aminoalkyl, substituted $C_1$ to $C_3$ aminoalkyl, $NO_2$, $C_1$ to $C_3$ perfluoroalkyl, $COR_B$, $CR_B=NOR_C$, $OCOR_B$, $NR_CCOR_B$, and 5 or 6 membered heterocyclic ring having in its backbone 1 to 3 heteroatoms selected from the group consisting of N, O, and S;

$R_B$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R_C$ is H, $C_1$ to $C_3$ alkyl, or substituted $C_1$ to $C_3$ alkyl;

$R_5$ is H, OH, halogen, CN, $NO_2$, $C_1$ to $C_6$ alkyl, substituted $C_1$ to $C_6$ alkyl, $C_2$ to $C_6$ alkynyl, substituted $C_2$ to $C_6$ alkynyl, $C_1$ to $C_6$ alkoxy, substituted $C_1$ to $C_6$ alkoxy, amino, $C_1$ to $C_6$ aminoalkyl, or substituted $C_1$ to $C_6$ aminoalkyl;

Q is O, S, $NR_8$, or $CR_9R_{10}$;

$R_8$ is selected from the group consisting of CN, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $SO_2CF_3$, $OR_{11}$, and $NR_{11}R_{12}$;

$R_9$ and $R_{10}$ are independent substituents selected from the group consisting of H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $NO_2$, CN, and $CO_2R_{11}$;

or $CR_9R_{10}$ is a six membered ring as shown by the structure below:

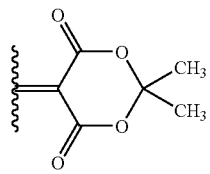

$R_{11}$ and $R_{12}$ are independently selected from the group consisting of H, $C_1$ to $C_6$ alkyl, substituted $C_1$ to $C_6$ alkyl, aryl, substituted aryl, heterocyclic, substituted heterocyclic, acyl, and sulfonyl;

X is O;

or a pharmaceutically acceptable salt, or tautomer thereof;

wherein:

said substituted alkyl, substituted alkenyl, and substituted alkynyl is an alkyl, alkenyl, and alkynyl, respectively, comprising one or more substituents selected from the group consisting of halogen, CN, OH, $NO_2$, amino, aryl, heterocyche, aryl, alkoxy, aryloxy, alkyloxy, alkylcarbonyl, alkylcarboxy, amino, and arylthio;

said substituted aryl is an aryl comprising one or more substituents selected from the group consisting of halogen, CN, OH, $NO_2$, amino, alkyl, cycloalkyl, alkenyl, alkynyl, alkoxy, aryloxy, alkyloxy, alkylcarbonyl, alkylcarboxy, alkylamino, and aryithio;

said substituted cycloalkyl is a cycloalkyl comprising one or more substituents selected from the group consisting of halogen, CN, OH, $NO_2$, amino, aryl, heterocyclic, aryl, alkoxy, aryloxy, alkyloxy, alkylcarbonyl, alkylcarboxy, amino, and aryithio;

said substituted alkoxy is an alkoxy comprising one or more substituents selected from the group consisting of halogen, CN, OH, $NO_2$, amino, aryl, heterocyclic, aryl, alkoxy, aryloxy, alkyloxy, alkylcarbonyl, alkylcarboxy, amino, and arylthio;

said substituted aminoalkyl is an aminoalkyl comprising one or more substituents selected from the group consisting of halogen, CN, OH, $NO_2$, amino, aryl, heterocyclic, aryl, alkoxy, aryloxy, alkyloxy, alkylcarbonyl, alkylcarboxy, amino, and arylthio;

said substituted heterocyclic is a heterocycle comprising one or more substituents selected from the group consisting of halogen, CN, OH, $NO_2$, amino, alkyl, cycloalkyl, alkenyl, alkynyl, alkoxy, aryloxy, alkyloxy, alkylcarbonyl, alkylcarboxy, alkylamino, and arylthio;

said substituted aryloxy is an aryloxy comprising one or more substituents selected from the group consisting of halogen, CN, OH, $NO_2$, amino, aryl, heterocyclic, aryl, alkoxy, aryloxy, alkyloxy, alkylcarbonyl, alkylcarboxy, amino, and arylthio;

said substituted thioalkoxy is a thioalkoxy comprising one or more substituents selected from the group consisting of halogen, CN, OH, $NO_2$, amino, aryl, heterocyclic, aryl, alkoxy, aryloxy, alkyloxy, alkylcarbonyl, alkylcarboxy, amino, and arylthio.

2. The progesterone receptor modulator according to claim 1, wherein in formula I:

$R_1$ is selected from the group consisting of H, $C_1$ to $C_3$ alkyl, substituted $C_1$ to $C_3$ alkyl, and $C_1$ to $C_3$ perfluoroalkyl;

$R_2$ and $R_3$ are independently selected from the group consisting of H, $C_1$ to $C_6$ alkyl, substituted $C_1$ to $C_6$ alkyl, $C_1$ to $C_6$ perfluoroalkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_6$ cycloalkyl, substituted $C_3$ to $C_6$ cycloalkyl, aryl, substituted aryl, heterocyclic, and substituted heterocyclic;

or $R_2$ and $R_3$ are fused to form the 3 to 8 membered saturated spirocyclic ring;

$R_4$ is selected from the group consisting of $NHR_7$, $OR_7$, $NHSO_2R_7$, and $SO_2R_7$;

$R_7$ is selected from the group consisting of (a) and (b):

(a) said aryl ring which is optionally substituted with one to three substituents independently selected from the group consisting of H, halogen, OH, CN, $C_1$ to $C_3$ alkyl, substituted $C_1$ to $C_3$ alkyl, $NO_2$, $C_1$ to $C_3$ perfluoroalkyl, $COR_B$, $CR_B=NOR_C$, $OCOR_B$, and $NR_CCOR_B$; and (b) said 5 or 6 membered heterocyclic ring containing in its backbone 1 to 3 heteroatoms selected from the group consisting of O, S, SO, $SO_2$ and N, wherein said heterocyclic ring is optionally substituted with one or more substituents independently selected from the group consisting of H, halogen, OH, CN, $C_1$ to $C_3$ alkyl, substituted $C_1$ to $C_3$ alkyl, $NO_2$, $C_1$ to $C_3$ perfluoroalkyl, $COR_B$, $CR_B=NOR_C$, $OCOR_B$, and $NR_CCOR_B$;

$R_B$ is selected from the group consisting of H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, and substituted $C_1$ to $C_3$ aminoalkyl;

$R_C$ is selected from the group consisting of H, $C_1$ to $C_3$ alkyl, and substituted $C_1$ to $C_3$ alkyl;

$R_5$ is H, OH, halogen, CN, or $NO_2$;

or a pharmaceutically acceptable salt, or tautomer thereof.

3. The progesterone receptor modulator according to claim 1, wherein in formula I:

$R_4$ is $NHR_7$;

$R_8$ is selected from the group consisting of CN, $C_1$ to $C_3$ alkyl, substituted $C_1$ to $C_3$ alkyl, $SO_2CF_3$, and $OR_{11}$;

$R_9$ and $R_{10}$ are independently selected from the group consisting of $C_1$ to $C_3$ alkyl, substituted $C_1$ to $C_3$ alkyl, $NO_2$, CN, and $CO_2R_{11}$;

$R_{11}$ and $R_{12}$ are independently selected from the group consisting of H, $C_1$ to $C_3$ alkyl, substituted $C_1$ to $C_3$ alkyl, acyl and sulfonyl;

or a pharmaceutically acceptable salt, or tautomer, thereof.

4. The progesterone receptor modulator according to claim 1, wherein in formula I:

$R_1$ is Me or $CF_3$ $R_2$ and $R_3$ are independently selected from the group consisting of $C_1$ to $C_4$ alkyl, substituted $C_1$ to $C_4$ alkyl, $C_2$ to $C_4$ alkenyl, substituted $C_2$ to $C_4$ alkenyl, $C_2$ to $C_4$ alkynyl, substituted $C_2$ to $C_4$ alkynyl, $C_3$ to $C_5$ cycloalkyl, substituted $C_3$ to $C_5$ cycloalkyl, aryl, substituted aryl, heterocyclic, and substituted heterocyclic;

or $R_2$ and $R_3$ are fused to form the 3 to 6 membered saturated spirocyclic ring;

$R_5$ is H, OH, halogen, CN, or $NO_2$;

Q is O or S;

X is O;

or a pharmaceutically acceptable salt, or tautomer thereof.

5. The progesterone receptor modulator according to claim 1 selected from the group consisting of:

6-[(3-chlorophenyl)amino]-4,4-diethyl-1-methyl-1,4-dihydro-2H-3,1-benzoxazin-2-one;

4-(4-chlorophenyl)-6-[(3-chlorophenyl)amino]-1,4-dimethyl-1,4-dihydro-2H-3,1-benzoxazin-2-one;

6-[(3,4-dichlorophenyl)amino]-4,4-diethyl-1-methyl-1,4-dihydro-2H-3,1-benzoxazin-2-one;

6-[(3,5-dichlorophenyl)amino]-4,4-diethyl-1-methyl-1,4-dihydro-2H-3,1-benzoxazin-2-one;

4,4-diethyl-6-[(3-fluoro-5-nitrophenyl)amino]-1-methyl-1,4-dihydro-2H-3,1-benzoxazin-2-one;

3-[(4,4-diethyl-1-methyl-2-oxo-1,4-dihydro-2H-3,1-benzoxazin-6-yl)amino]-5-fluorobenzonitrile;

6-[(2,3-dichlorophenyl)amino]-4,4-diethyl-1-methyl-1,4-dihydro-2H-3,1-benzoxazin-2-one;

6-[(2,5-dichlorophenyl)amino]-4,4-diethyl-1-methyl-1,4-dihydro-2H-3,1-benzoxazin-2-one;

6-[(3,4-difluorophenyl)amino]-4,4-diethyl-1-methyl-1,4-dihydro-2H-3,1-benzoxazin-2-one;

6-[(3,5-difluorophenyl)amino]-4,4-diethyl-1-methyl-1,4-dihydro-2H-3,1-benzoxazin-2-one;

6-[(3-chloro-4-fluorophenyl)amino]-4,4-diethyl-1-methyl-1,4-dihydro-2H-3,1-benzoxazin-2-one;

6-[(3-acetylphenyl)amino]-4,4-diethyl-1-methyl-1,4-dihydro-2H-3,1-benzoxazin-2-one;

5-[(4,4-diethyl-1-methyl-2-oxo-1,4-dihydro-2H-3,1-benzoxazin-6-yl)amino]-2-fluorobenzonitrile;

6-[(3-acetyl-4-fluorophenyl)amino]-4,4-diethyl-1-methyl-1,4-dihydro-2H-3,1-benzoxazin-2-one;

6-[(4-bromophenyl)amino]-4,4-diethyl-1-methyl-1,4-dihydro-2H-3,1-benzoxazin-2-one;

4-[(4,4-diethyl-1-methyl-2-oxo-1,4-dihydro-2H-3,1-benzoxazin-6-yl)amino]-2-fluorobenzonitrile;

6-[(2,3-dichlorophenyl)amino]-4,4-dimethyl-1,4-dihydro-2H-3,1-benzoxazin-2-one;

6-[(2,3-dichlorophenyl)amino]-1,4,4-trimethyl-1,4-dihydro-2H-3,1-benzoxazin-2-one;

6-[(4-bromophenyl)amino]-1,4,4-trimethyl-1,4-dihydro-2H-3,1-benzoxazin-2-one;

1,4,4-trimethyl-6-[(4-nitrophenyl)amino]-1,4-dihydro-2H-3,1-benzoxazin-2-one;

6-[(3-chloro-4-fluorophenyl)amino]-4,4-diethyl-5-fluoro-1-methyl-1,4-dihydro-2H-3,1-benzoxazin-2-one;

6-[(3-chlorophenyl)amino]-4-ethyl-4-thien-2-yl-1,4-dihydro-2H-3,1-benzoxazin-2-one;

6-[(3-chlorophenyl)amino]-4-ethyl-1-methyl-4-thien-2-yl-1,4-dihydro-2H-3,1-benzoxazin-2-one;

6-[(3-chloro-4-fluorophenyl)amino]-4-ethyl-4-thien-2-yl-1,4-dihydro-2H-3,1-benzoxazin-2-one;

6-[(3-chloro-4-fluorophenyl)amino]-4-ethyl-1-methyl-4-thien-2-yl-1,4-dihydro-2H-3,1-benzoxazin-2-one;

5-fluoro-3-[(1-methyl-2-oxo-1,2-dihydrospiro[3,1-benzoxazine-4,1'-cyclopentan]-6-yl)amino]benzonitrile 6-[(4-bromophenyl)amino]-4-(4-chlorophenyl)-1,4-dimethyl-1,4-dihydro-2H-3,1-benzoxazin-2-one;

6-[(4-bromophenyl)amino]-4-ethyl-1-methyl-4-thien-2-yl-1,4-dihydro-2H-3,1-benzoxazin-2-one;

4-[(1,4,4-trimethyl-2-oxo-1,4-dihydro-2H-3,1-benzoxazin-6-yl)amino]benzonitrile;

4-[(1,4,4-trimethyl-2-oxo-1,4-dihydro-2H-3,1-benzoxazin-6-yl)amino]benzonitrile;

6-[(2,4-dichlorophenyl)amino]-1,4,4-trimethyl-1,4-dihydro-2H-3,1-benzoxazin-2-one;

1,4,4-trimethyl-6-(1-naphthylamino)-1,4-dihydro-2H-3,1-benzoxazin-2-one;

6-[(4-bromophenyl)amino]-1,4-dimethyl-4-thien-2-yl-1,4-dihydro-2H-3,1-benzoxazin-2-one;

6-[(3,4-dichlorophenyl)amino]-1,4,4-trimethyl-1,4-dihydro-2H-3,1-benzoxazin-2-one;

6-[(2-chloro-4-nitrophenyl)amino]-1,4,4-trimethyl-1,4-dihydro-2H-3,1-benzoxazin-2-one;

6-[(2-methoxyphenyl)amino]-1,4,4-trimethyl-1,4-dihydro-2H-3,1-benzoxazin-2-one;

1,4,4-trimethyl-6-[(2-methylphenyl)amino]-1,4-dihydro-2H-3,1-benzoxazin-2-one;

6-[(2-bromophenyl)amino]-1,4,4-trimethyl-1,4-dihydro-2H-3,1-benzoxazin-2-one;

4-(4-chlorophenyl)-6-[(4-chlorophenyl)amino]-1,4-dimethyl-1,4-dihydro-2H-3,1-benzoxazin-2-one;

6-[(4-bromo-2-chlorophenyl)amino]-1,4,4-trimethyl-1,4-dihydro-2H-3,1-benzoxazin-2-one;

6-[(4-ethoxyphenyl)amino]-1,4,4-trimethyl-1,4-dihydro-2H-3,1-benzoxazin-2-one;

6-[(4-bromophenyl)amino]-1-ethyl-4,4-dimethyl-1,4-dihydro-2H-3,1-benzoxazin-2-one;

6-[(2-ethylphenyl)amino]-1,4,4-trimethyl-1,4-dihydro-2H-3,1-benzoxazin-2-one;

1,4,4-Trimethyl-6-(4-phenoxy-phenylamino)-1,4-dihydro-benzo[d][1,3]oxazin-2-one;

6-(4-Hydroxy-phenylamino)-1,4,4-trimethyl-1,4-dihydro-benzo[d][1,3]oxazin-2-one;

6-[(4-bromophenyl)amino]-4,4-bis(4-chlorophenyl)-1-methyl-1,4-dihydro-2H-3,1-benzoxazin-2-one;

4,4-bis(4-chlorophenyl)-6-[(3-chlorophenyl)amino]-1-methyl-1,4-dihydro-2H-3,1-benzoxazin-2-one;

4-benzyl-6-[(4-bromophenyl)amino]-1,4-dimethyl-1,4-dihydro-2H-3,1-benzoxazin-2-one;

4-benzyl-6-[(2-chlorophenyl)amino]-1,4-dimethyl-1,4-dihydro-2H-3,1-benzoxazin-2-one;
4-benzyl-6-[(3-chlorophenyl)amino]-1,4-dimethyl-1,4-dihydro-2H-3,1-benzoxazin-2-one;
6-[(4-bromophenyl)amino]-1-isopropyl-4,4-dimethyl-1,4-dihydro-2H-3,1-benzoxazin-2-one;
6-[(4-chlorophenyl)amino]-8-methoxy-1,4,4-trimethyl-1,4-dihydro-2H-3,1-benzoxazin-2-one;
4-(4-chlorophenyl)-6-[(3-chlorophenyl)amino]-4-ethyl-1,4-dihydro-2H-3,1-benzoxazin-2-one;
4-(4-chlorophenyl)-6-[(3-chlorophenyl)amino]-4-ethyl-1-methyl-1,4-dihydro-2H-3,1-benzoxazin-2-one;
4-(4-chlorophenyl)-6-[(3-chlorophenyl)amino]-1,4,8-trimethyl-1,4-dihydro-2H-3,1-benzoxazin-2-one;
6-[(3-chlorophenyl)amino]-4-ethyl-4-phenyl-1,4-dihydro-2H-3,1-benzoxazin-2-one;
6-[(3-chlorophenyl)amino]-4-ethyl-1-methyl-4-phenyl-1,4-dihydro-2H-3,1-benzoxazin-2-one;
4-(4-chlorophenyl)-6-[(3-chlorophenyl)amino]-8-methoxy-1,4-dimethyl-1,4-dihydro-2H-3,1-benzoxazin-2-one;
6-(3-Chloro-phenylamino)-1,4,4-trimethyl-1,4-dihydro-benzo[d][1,3]oxazin-2-one;
6-(4-Fluoro-phenylamino)-1,4,4-trimethyl-1,4-dihydro-benzo[d][1,3]oxazin-2-one;
6-(4-Methoxy-phenylamino)-1,4,4-trimethyl-1,4-dihydro-benzo[d][1,3]oxazin-2-one;
1,4,4-Trimethyl-6-p-tolylamino-1,4-dihydro-benzo[d][1,3]oxazin-2-one;
6-(4-Bromo-phenylamino)-1,4,4-trimethyl-1,4-dihydro-benzo[d][1,3]oxazin-2-one;
6-(3,4-Difluoro-phenylamino)-1,4,4-trimethyl-1,4-dihydro-benzo[d][1,3]oxazin-2-one;
6-(3,5-Difluoro-phenylamino)-1,4,4-trimethyl-1,4-dihydro-benzo[d][1,3]oxazin-2-one;
6-(2-Fluoro-3-methoxy-phenylamino)-1,4,4-trimethyl-1,4-dihydro-benzo[d][1,3]oxazin-2-one;
(4,4-dimethyl-2-oxo-1,4-dihydro-2H-3,1-benzoxazin-6-yl)-2,3-dichlorobenzenesulfonate;
(1,4,4-trimethyl-2-oxo-1,4-dihydro-2H-3,1-benzoxazin-6-yl)-2,3-dichlorobenzenesulfonate;
2,3-dichloro-N-(4,4-dimethyl-2-oxo-1,4-dihydro-2H-3,1-benzoxazin-6-yl)benzenesulfonamide;
2,3-dichloro-N-(1,4,4-trimethyl-2-oxo-1,4-dihydro-2H-3,1-benzoxazin-6-yl)benzenesulfonamide;
6-{[4-(dimethylamino)phenyl]amino}-1,4,4-trimethyl-1,4-dihydro-2H-3,1-benzoxazin-2-one;
6-[(4-chlorophenyl)amino]-1,4,4-trimethyl-1,4-dihydro-2H-3,1-benzoxazin-2-one; and
6-[(2-chlorophenyl)amino]-1,4,4-trimethyl-1,4-dihydro-2H-3,1-benzoxazin-2-one;
or a pharmaceutically acceptable salt, or tautomer thereof.

6. The compound according to claim 1, wherein said compound is selected from the group consisting of:
6-[(3,4-difluorophenyl)amino]-4,4-diethyl-1-methyl-1,4-dihydro-2H-3,1-benzoxazine-2-thione; and
6-[(4-bromophenyl)amino]-1,4,4-trimethyl-1,4-dihydro-2H-3,1-benzoxazine-2-thione;
or a pharmaceutically acceptable salt, or tautomer thereof.

7. The compound according to claim 1, wherein said compound is selected from the group consisting of 6-(3-chloro-4-fluorophenoxy)-4,4-diethyl-1-methyl-1,4-dihydro-benzo[d][1,3]oxazin-2-one and 3-(4,4-diethyl-1-methyl-2-oxo-1,4-dihydro-2H-benzo[d][1,3]oxazin-6-yloxy)-5-fluoro-benzonitrile; or a pharmaceutically acceptable salt, or tautomer thereof.

8. A pharmaceutical composition comprising a compound according to claim 1 and a physiologically compatible carrier.

9. A method for contraception comprising administering to a female of child-bearing age a progesterone receptor modulator having the formula:

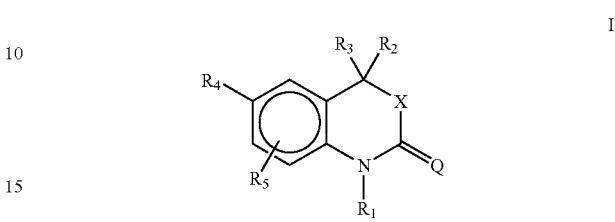

wherein:
$R_1$ is H, OH, $C_1$ to $C_3$ alkyl, substituted $C_1$ to $C_3$ alkyl, $C_1$ to $C_3$ perfluoroalkyl, or $COR_6$;
$R_6$ is H, $C_1$ to $C_4$ alkyl, substituted $C_1$ to $C_4$ alkyl, aryl, substituted aryl, $C_1$ to $C_4$ alkoxy, substituted $C_1$ to $C_4$ alkoxy, $C_1$ to $C_3$ aminoalkyl, or substituted $C_1$ to $C_3$ aminoalkyl;
$R_2$ and $R_3$ are independently selected from the group consisting of H, $C_1$ to $C_6$ alkyl, substituted $C_1$ to $C_6$ alkyl, $C_1$ to $C_6$ perfluoroalkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_6$ cycloalkyl, substituted $C_3$ to $C_6$ cycloalkyl, aryl, substituted aryl, heterocyclic, and substituted heterocyclic;
or $R_2$ and $R_3$ are fused to form:
(i) 3 to 8 membered saturated spirocyclic ring;
(ii) 3 to 8 membered spirocyclic ring having in its backbone one or more carbon-carbon double bonds; or
(iii) 3 to 8 membered saturated spirocyclic ring having in its backbone one to three heteroatoms selected from the group consisting of O, S, and N;
$R_4$ is $NHR_7$, $OR_7$, $NHSO_2R_7$, $OSO_2R_7$, $NCH_3R_7$ or $NCH_3SO_2R_7$;
$R_7$ is selected from the group consisting of (a) and (b):
(a) an aryl ring which is optionally substituted with one to three independent substituents selected from the group consisting of H, halogen, OH, CN, $C_1$ to $C_3$ alkyl, substituted $C_1$ to $C_3$ alkyl, $C_2$ to $C_3$ alkenyl, substituted $C_2$ to $C_3$ alkenyl, $C_2$ to $C_3$ alkynyl, substituted $C_2$ to $C_3$ alkynyl, $C_1$ to $C_3$ alkoxy, substituted $C_1$ to $C_3$ alkoxy, $C_5$ to $C_8$ aryloxy, substituted $C_5$ to $C_8$ aryloxy, $C_1$ to $C_3$ thioalkoxy, substituted $C_1$ to $C_3$ thioalkoxy, amino, $C_1$ to $C_3$ aminoalkyl, substituted $C_1$ to $C_3$ aminoalkyl, $NO_2$, $C_1$ to $C_3$ perfluoroalkyl, $COR_B$, $CR_B$=$NOR_C$, $OCOR_B$, $NR_CCOR_B$, 5 or 6 membered heterocyclic ring containing in its backbone 1 to 3 heteroatoms selected from the group consisting of N, O, and S; and
(b) a 5 or 6 membered heterocyclic ring containing in its backbone 1 to 3 heteroatoms selected from the group consisting of O, S, SO, $SO_2$ and N and optionally substituted with one to three independent substituents selected from the group consisting of H, halogen, OH, CN, $C_1$ to $C_3$ alkyl, substituted $C_1$ to $C_3$ alkyl, $C_2$ to $C_3$ alkenyl, substituted $C_2$ to $C_3$ alkenyl, $C_2$ to $C_3$ alkynyl, substituted $C_2$ to $C_3$ alkynyl, $C_1$ to $C_3$ alkoxy, substituted $C_1$ to $C_3$ alkoxy, $C_1$ to $C_3$ thioalkoxy, substituted $C_1$ to $C_3$ thioalkoxy, amino, $C_1$ to $C_3$ aminoalkyl, substituted $C_1$ to $C_3$ aminoalkyl, $NO_2$, $C_1$ to $C_3$ perfluoroalkyl, $COR_B$, $CR_B\!=\!NOR_C$, $OCOR_B$, $NR_CCOR_B$, and 5 or 6 membered heterocyclic ring having in its backbone 1 to 3 heteroatoms selected from the group consisting of N, O, and S;

$R_B$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R_C$ is H, $C_1$ to $C_3$ alkyl, or substituted $C_1$ to $C_3$ alkyl;

$R_5$ is H, OH, halogen, CN, $NO_2$, $C_1$ to $C_6$ alkyl, substituted $C_1$ to $C_6$ alkyl, $C_2$ to $C_6$ alkynyl, substituted $C_2$ to $C_6$ alkynyl, $C_1$ to $C_6$ alkoxy, substituted $C_1$ to $C_6$ alkoxy, amino, $C_1$ to $C_6$ aminoalkyl, or substituted $C_1$ to $C_6$ aminoalkyl;

Q is O, S, $NR_8$, or $CR_9R_{10}$;

$R_8$ is selected from the group consisting of CN, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $SO_2CF_3$, $OR_{11}$, and $NR_{11}R_{12}$;

$R_9$ and $R_{10}$ are independent substituents selected from the group consisting of H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $NO_2$, CN, and $CO_2R_{11}$;

or $CR_9R_{10}$ is a six membered ring as shown by the structure below:

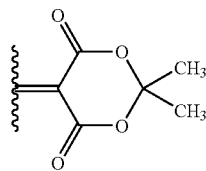

$R_{11}$ and $R_{12}$ are independently selected from the group consisting of H, $C_1$ to $C_6$ alkyl, substituted $C_1$ to $C_6$ alkyl, aryl, substituted aryl, heterocyclic, substituted heterocyclic, acyl, and sulfonyl;

X is O;

or a pharmaceutically acceptable salt, or tautomer thereof; wherein:

said substituted alkyl, substituted alkenyl, and substituted alkynyl is an alkyl, alkenyl, and alkynyl, respectively, comprising one or more substituents selected from the group consisting of halogen, CN, OH, $NO_2$, amino, aryl, heterocyhe, aryl, alkoxy, aryloxy, alkyloxy, alkylcarbonyl, alkylcarboxy, amino, and arylthio;

said substituted aryl is an aryl comprising one or more substituents selected from the group consisting of halogen, CN, OH, $NO_2$, amino, alkyl, cycloalkyl, alkenyl, alkynyl, alkoxy, aryloxy, alkyloxy, alkylcarbonyl, alkylcarboxy, alkylamino, and aryithio;

said substituted cycloalkyl is a cycloalkyl comprising one or more substituents selected from the group consisting of halogen, CN, OH, $NO_2$, amino, aryl, heterocyclic, aryl, alkoxy, aryloxy, alkyloxy, alkylcarbonyl, alkylcarboxy, amino, and aryithio;

said substituted alkoxy is an alkoxy comprising one or more substituents selected from the group consisting of halogen, CN, OH, $NO_2$, amino, aryl, heterocyclic, aryl, alkoxy, aryloxy, alkyloxy, alkylcarbonyl, alkylcarboxy, amino, and arylthio;

said substituted aminoalkyl is an aminoalkyl comprising one or more substituents selected from the group consisting of halogen, CN, OH, $NO_2$, amino, aryl, heterocyclic, aryl, alkoxy, aryloxy, alkyloxy, alkylcarbonyl, alkylcarboxy, amino, and arylthio;

said substituted heterocyclic is a heterocycle comprising one or more substituents selected from the group consisting of halogen, CN, OH, $NO_2$, amino, alkyl, cycloalkyl, alkenyl, alkynyl, alkoxy, aryloxy, alkyloxy, alkylcarbonyl, alkylcarboxy, alkylamino, and arylthio;

said substituted aryloxy is an aryloxy comprising one or more substituents selected from the group consisting of halogen, CN, OH, $NO_2$, amino, aryl, heterocyclic, aryl, alkoxy, aryloxy, alkyloxy, alkylcarbonyl, alkylcarboxy, amino, and arylthio;

said substituted thioalkoxy is a thioalkoxy comprising one or more substituents selected from the group consisting of halogen, CN, OH, $NO_2$, amino, aryl, heterocyclic, aryl, alkoxy, aryloxy, alkyloxy, alkylcarbonyl, alkylcarboxy, amino, and arylthio.

10. The method for contraception according to claim 9, which comprises administering to a female of child bearing age for 28 consecutive days:

a) a first phase of from 14 to 24 daily dosage units of a progestational agent equal in progestational activity to about 35 to about 100 µg levonorgestrel;

b) a second phase of from 1 to 11 daily dosage units, at a daily dosage of from about 2 to 50 mg of an antiprogestin compound of formula I; and c) optionally, a third phase of daily dosage units of an orally and pharmaceutically acceptable placebo for the remaining days of the 28 consecutive days in which no antiprogestin, progestin or estrogen is administered; wherein the total daily dosage units of the first, second and third phases equals 28.

11. A method for treating uterine fibroids comprising administering to a patient in need thereof a compound according to claim 1.

12. A method for treating endometriosis comprising administering to a patient in need thereof a compound according to claim 1.

13. A method for treating dysmenorrhea comprising administering to a patient in need thereof a compound according to claim 1.

14. A method for treating breast cancer comprising administering to a patient in need thereof a compound according to claim 1.

15. A method for treating uterine cancer comprising administering to a patient in need thereof a compound according to claim 1.

* * * * *

UNITED STATES PATENT AND TRADEMARK OFFICE
CERTIFICATE OF CORRECTION

PATENT NO. : 7,247,625 B2
APPLICATION NO. : 10/946476
DATED : July 24, 2007
INVENTOR(S) : Zhang et al.

It is certified that error appears in the above-identified patent and that said Letters Patent is hereby corrected as shown below:

Col. 29, line 37, replace "1.19." with -- 11.19. --.

Col. 31, line 53, replace "$C_{12}$" with -- $Cl_2$ --.

Col. 45, line 52, replace "$C_{12}$" with -- $Cl_2$ --.

Col. 57, line 64, replace "heterocyche," with -- heterocyclic, --.

Col. 58, line 3, replace "aryithio" with -- arylthio --.

Col. 58, line 8, replace "aryithio" with -- arylthio --.

Col. 63, line 49, replace "heterocyche," with -- heterocyclic, --.

Col. 63, line 55, replace "aryithio" with -- arylthio --.

Col. 63, line 60, replace "aryithio" with -- arylthio --.

Col. 64, lines 35-36, delete "an antiprogestin" and insert -- a progesterone receptor modulator --.

UNITED STATES PATENT AND TRADEMARK OFFICE
CERTIFICATE OF CORRECTION

PATENT NO. : 7,247,625 B2
APPLICATION NO. : 10/946476
DATED : July 24, 2007
INVENTOR(S) : Zhang et al.

It is certified that error appears in the above-identified patent and that said Letters Patent is hereby corrected as shown below:

Col. 64, lines 53-58, delete claims 14 and 15 and insert the following claims 14 and 15.

-- 14. A method for treating acne comprising administering to a patient in need thereof a compound according to claim 1.

15. A method for treating hirsutism comprising administering to a patient in need thereof a compound according to claim 1. --.

Signed and Sealed this

Eleventh Day of March, 2008

JON W. DUDAS
*Director of the United States Patent and Trademark Office*